US007087687B2

(12) United States Patent
Goodall et al.

(10) Patent No.: US 7,087,687 B2
(45) Date of Patent: Aug. 8, 2006

(54) CATALYTIC COMPOSITION AND ITS PREPARATION AND USE FOR PREPARING POLYMERS FROM ETHYLENICALLY UNSATURATED MONOMERS

(75) Inventors: Brian Leslie Goodall, Amber, PA (US); Jennifer Lynn Petoff, Yardley, PA (US); Han Shen, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 110 days.

(21) Appl. No.: 10/857,330

(22) Filed: May 28, 2004

(65) Prior Publication Data

US 2005/0043494 A1 Feb. 24, 2005

Related U.S. Application Data

(60) Provisional application No. 60/496,873, filed on Aug. 21, 2003, provisional application No. 60/559,243, filed on Apr. 2, 2004.

(51) Int. Cl.
C08F 4/80 (2006.01)
C08F 4/70 (2006.01)

(52) U.S. Cl. ............... 526/117; 526/113; 526/171; 526/172; 502/113; 502/162; 502/167; 556/35; 556/37; 556/110; 556/136; 556/137; 556/138

(58) Field of Classification Search ........... 502/113, 502/162, 167; 526/113, 117, 171, 172; 556/37, 556/35, 110, 136, 137, 138
See application file for complete search history.

(56) References Cited

U.S. PATENT DOCUMENTS

| 3,821,181 | A | | 6/1974 | Jufa et al. |
| 5,442,020 | A | * | 8/1995 | Davis ............... 526/127 |
| 5,929,181 | A | | 7/1999 | Makovetsky et al. |
| 6,037,297 | A | | 3/2000 | Stibrany et al. |
| 6,242,622 | B1 | * | 6/2001 | Oda et al. ............. 556/11 |
| 6,265,506 | B1 | | 7/2001 | Goodall et al. |
| 6,300,440 | B1 | | 10/2001 | Sen et al. |
| 6,303,724 | B1 | | 10/2001 | Goodall et al. |
| 6,350,832 | B1 | | 2/2002 | Bell et al. |
| 6,417,303 | B1 | | 7/2002 | Stibrany et al. |
| 6,455,650 | B1 | | 9/2002 | Lipian et al. |
| 6,506,861 | B1 | | 1/2003 | Wang et al. |
| 6,541,585 | B1 | | 4/2003 | Johnson et al. |
| 6,544,919 | B1 | | 4/2003 | Tagge et al. |
| 6,593,440 | B1 | | 7/2003 | Sen et al. |
| 6,677,419 | B1 | | 1/2004 | Brock et al. |
| 6,723,486 | B1 | | 4/2004 | Goodall et al. |
| 2002/0040115 | A1 | | 4/2002 | Sen et al. |
| 2003/0144441 | A1 | | 7/2003 | Sen et al. |
| 2003/0171209 | A1 | | 9/2003 | Wang et al. |
| 2004/0054207 | A1 | | 3/2004 | Kim et al. |
| 2004/0063885 | A1 | | 4/2004 | Rhodes et al. |

FOREIGN PATENT DOCUMENTS

| EP | 0589527 B1 | 7/1999 |
| WO | WO0006615 | 10/2000 |
| WO | WO0192354 | 6/2001 |
| WO | WO 03/102038 A | 12/2003 |

OTHER PUBLICATIONS

Christine Elia, et al., "Palladium-Based System for the Polymerization of Acrylates.", Organometallics 2002, 21, pp. 4229-4256, Jun. 3, 2002.
John Lipian, et al., Addition Polymerization of Norbornene-Type Monomers. High Activity Cationic Allyl Palladium Catalysts, Macromolecules 2002, 35. pp. 8969-8977. Sep. 3, 2002.
George M. Benedikt, "Copolymerization of Ethene with Norbornene Derivatives Using Neutral Nickel Catalysts", Macromolecules 2002, 35. pp. 8978-8988. Sep. 17, 2002.
Dennis A. Barnes, et al., "Addition Polymerization of Norbornene-Type Monomers Using Neutral Nickel Complexes Containing Fluorinated Aryl Ligands", Macromolecules 2003, 36. pp. 2623-2632. Feb. 11, 2003.
Elite Drent, et al. "Palladium Catalysed Copolymerization of Ethene with Alkylacrylates: Polar Comonomer Built into the Linear Polymer Chain", ChemComm www.rsc.org/chemcomm Dec. 10, 2001.
Ilia A. Guzei, et al., "Benzenedicarbonyl and Benzenetricarbonyl Linker Pyrazolyl Complexes of Palladium(II): Synthesis, X-ray Structures and Evaluation as Ethylene Polymerisation Catalyst", Dalto www.rsc.org/dalton Aug. 28, 2002.
(XP-002309203) Britovsek, George J.P. et al., "Cationic Methylpalladium(II) Complexes Containing Bidentate N-O and P-O Ligands and a Tridentate P-O-N Ligand: Synthesis, Carbonylation and Catalytic Applications in the Copolymerisation of Carbon Monoxide and Ethene", *Journal of Organometallic Chemistry*, 533, 201-212, (1997).

(Continued)

Primary Examiner—Caixia Lu
(74) Attorney, Agent, or Firm—Richard R. Clikeman

(57) ABSTRACT

A catalytic composition, including a cationic metal-pair complex, is disclosed, along with a method for its preparation. A method for the polymerization of ethylenically unsaturated monomers using the catalytic composition, and the addition polymers produced thereby are also disclosed.

11 Claims, No Drawings

OTHER PUBLICATIONS (XP-002309202) Thomas, Rüether et al., "Novel Methylpalladium (II) Complexes Bearing Tridententate Imidazole-Based Chelate Ligands: Synthesis Structural Characterization, and Reactivity", *Organometallics*, 20, 5522-5531 (2001).

(XP-002253038) Pickel, Marco et al. "Facile Preparation and Activation of High Productivity Single-Site Nickel Catalysts for Highly Linear Polyethylene", *Helvetica Chimica Acta, Verlag Helvetica Chimica Acta* 85, 4337-4352, (2002).

* cited by examiner

US 7,087,687 B2

CATALYTIC COMPOSITION AND ITS PREPARATION AND USE FOR PREPARING POLYMERS FROM ETHYLENICALLY UNSATURATED MONOMERS

This patent application derives priority from: U.S. patent application Ser. No. 60/496,873, filed Aug. 21, 2003; and a U.S. patent application Ser. No. 60/559,243, filed Apr. 2, 2004.

The present invention relates to a catalytic composition and a method of preparing that catalytic composition. The present invention further relates to a method for polymerizing ethylenically unsaturated monomers, including non-polar olefinic monomers, polar olefinic monomers, and combinations thereof, in the presence of the catalytic composition, and to the polymers produced thereby.

Both polyolefins and polyacrylates find their origins in the 1930's. At their inception, both families of polymers were made using free radical chemistry, and seventy years later acrylic polymers continue to be made predominately using free radical chemistry carried out predominately in batch mode. Ethylene polymerization, on the other hand, has enjoyed a number of breakthroughs so that today the preponderance of polyethylene produced (>80%) is prepared by continuous processes using transition metal catalysts. The use of transition metal catalysts has significantly improved economics (low energy, low pressure processes), greatly improved product properties (e.g., the strength of ultra-thin plastic bags), resulted in new products (new grades of polyethylene, elastomers, medical packaging) and even brand new polymers (e.g., polypropylene) by virtue of the molecular level control of polymer architecture endowed by these catalysts.

The evolution of olefin polymerization catalysis since Karl Ziegler's Nobel Prize-winning discovery of the transition metal catalyzed polymerization of ethylene in 1953 has involved a prolific coupling of polymer science with organometallic chemistry. Successes include the development of catalysts that rival the activities of enzymes, and of systems that yield polyolefins with controlled molecular weights and tacticities. In stark contrast, despite nearly 50 years of intense activity and progress spurred on by the predicted enormous profits associated with the new commercial products that would become accessible, there are no commercially viable catalysts for the polymerization of acrylates or the controlled copolymerization of simple olefins with polar functional monomers.

Currently, commercial processes for the copolymerization of ethylene with polar monomers such as acrylates, methacrylates, and vinyl acetate employ free radical processes in which the incorporation of the polar functionality is relatively random. The use of free radical initiators across the entire acrylic polymer market gives little or no control over polymer architecture (tacticity or crystallinity, blockiness, molecular weight, and molecular weight distribution) and thus limits the accessible range of materials performance properties. Because these free radical processes require extreme pressures, they are associated with high capital investment and manufacturing costs, and, of course, increased safety hazards.

Industry-wide, a need exists for new molecular catalysts capable of polymerizing polar monomers in a controlled fashion and for copolymerizing the same monomers with olefins (e.g. ethylene, propylene, styrene, octene, norbornene) under mild reaction conditions and in a stereoregular ("tactic") fashion. Of the many approaches to modifying the properties of a polymer that are available, the incorporation of functional groups into an otherwise non-polar material is of paramount importance. Polar groups exercise control over important polymer properties such as toughness, adhesion, barrier properties, and surface properties. These polymer properties manifest themselves in the properties of materials incorporating the polymer, such as solvent resistance, miscibility with other polymers, and rheological properties, leading to product performance such as paintability, printability, gloss, hardness, and mar resistance. By incorporating polar groups into hydrocarbon polymers such as polyethylene, polypropylene and polystyrene, not only would the important properties related to crystallinity (modulus, strength, solvent resistance, etc.) be maintained, but new properties would also be expressed.

In recent years, late transition metal catalysts have attracted attention not only for the polymerization of $\alpha$-olefins, but more importantly for the copolymerization of hydrocarbon monomers with readily available polar monomers such as acrylates and vinyl acetate. Only very recently have these single metal centered catalysts provided the very first examples of the transition-metal catalyzed incorporation of acrylate monomers into linear polyethylene been demonstrated. Unfortunately, all of these reports describe catalysts with poor performance; low productivity, low molecular weight copolymers and low levels of polar monomer incorporation.

The total focus on single metal centered catalysts is apparent from myriad papers and reviews of the area. For example, Rolf Muelhaupt in "Catalytic Polymerization and Post Polymerization Catalysis Fifty Years After the Discovery of Ziegler's Catalysts", *Macromol. Chem. Phys.* 2003, 204, 289–327 elegantly and comprehensively reviews fifty years of developments and again we highlight that exclusively single metal or monometallic catalysts are described and reviewed—regardless of whether the catalysts are based on early transition metals such as titanium or zirconium, or late transition metals such as nickel and palladium, or whether the catalysts were studied in the 1950's, 60's, 70's, 80's, 90's or the present day. FIGS. 12 and 13 on page 298 of the Muelhaupt reference (vide supra) clearly summarize this concentration on single metal centers rather than the metal atom pair containing complexes of the present invention.

U.S. Pat. No. 6,303,724 discloses the use of specific monometallic cationic Pd complexes to polymerize mixtures of norbornene and acrylate monomers to make norbornene/ acrylate compositions. Unfortunately, the method of U.S. Pat. No. 6,303,724 produces mixtures, the copolymer content of which is low (see Comparative Examples herein), so low, in fact, that these mixtures of polymers are ineffectual in uses for which a pure copolymer could be employed with advantageous result. In fact, in the presence of both norbornene and acrylate monomers, those monometallic cationic Pd complexes give only homopolymers of norbornene with no acrylate incorporation or, at most, homopolymers having a single acrylate monomer incorporated as an end group.

We have surprisingly discovered a catalytic composition including a new family of cationic metal-pair complexes which are very active in the homo- and co-polymerization of ethylenically unsaturated monomers. The ethylenically unsaturated monomers polymerizable by catalysis using the catalytic composition of the present invention include non-polar olefinic monomers, polar olefinic monomers, and combinations thereof. This new family of catalytic compositions includes cationic metal-pair complexes wherein the cationic metal-pair complex includes at least one metal atom pair, and each metal of the metal atom pair has four (4) occupied coordination sites.

One aspect of the present invention is directed to a catalytic composition comprising at least one cationic metal-pair complex, wherein:
  said cationic metal-pair complex comprises at least one metal atom pair, said pair comprising a first metal atom, $M^1$, and a second metal atom, $M^2$;
  said first metal atom and said second metal atom of said pair have a through-space internuclear distance of at least 1.5 Angstroms and no more than 20 Angstroms; and
  said cationic metal-pair complex is a complex according to formula I,

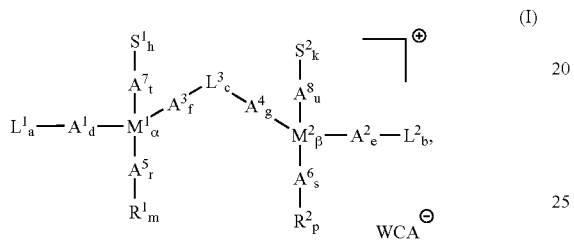

wherein:
  $M^1$ represents a first metal atom selected from the group consisting of: nickel, palladium, platinum, copper, silver, gold, iron, cobalt, rhodium, chromium, and manganese;
  $M^2$ represents a second metal atom selected from the group consisting of: nickel, palladium, platinum, copper, silver, gold, iron, cobalt, rhodium, chromium, and manganese;
  $L^1$ represents a set of first ligands;
  $L^2$ represents a set of second ligands;
  $L^3$ represents a set of third ligands;
  $R^1$ represents a set of first anionic hydrocarbyl containing radicals;
  $R^2$ represents a set of second anionic hydrocarbyl containing radicals;
  $S^1$ represents a set of first labile ligands;
  $S^2$ represents a set of second labile ligands;
  $A^1$–$A^8$ each represent a set of coordination bonds;
  WCA represents a weakly coordinating anion;
  a, b, h, k, m, and p are selected from 0 or 1;
  $\alpha$, $\beta$, and c each equal 1;
  d, e, r, s, t, and u are selected from 0, 1, 2, or 3; and
  f and g are selected from 1, 2, 3, or 4; and
  wherein: $0 \leq d+e \leq 5$; $1 \leq m+p \leq 2$; $1 \leq r+s \leq 5$; $0 \leq t+u \leq 5$; $2 \leq f+g \leq 7$; the sum $d+f+r+t=4$; and the sum $e+g+s+u=4$.

A second aspect of the present invention is directed to a polymerization system comprising a catalytic composition of claim 1 and at least one ethylenically unsaturated monomer, wherein said first metal atom and said second metal atom exhibit cooperativity during catalysis of the polymerization of ethylenically unsaturated monomers.

A third aspect of the present invention is directed to a method for preparing said catalytic composition of claim 1, comprising the steps of:
  (i) providing at least one precursor complex according to formula II

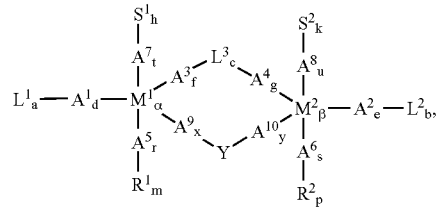

wherein:
  $M^1$ represents a first metal atom selected from the group consisting of: nickel, palladium, platinum, copper, silver, gold, iron, cobalt, rhodium, chromium, and manganese;
  $M^2$ represents a second metal atom selected from the group consisting of: nickel, palladium, platinum, copper, silver, gold, iron, cobalt, rhodium, chromium, and manganese;
  $L^1$ represents a set of first ligands;
  $L^2$ represents a set of second ligands;
  $L^3$ represents a set of third ligands;
  $R^1$ represents a set of first anionic hydrocarbyl containing radicals;
  $R^2$ represents a set of second anionic hydrocarbyl containing radicals;
  $S^1$ represents a set of first labile ligands;
  $S^2$ represents a set of second labile ligands;
  $A^1$–$A^{10}$ each represent a set of coordination bonds;
  WCA represents a weakly coordinating anion; and
  Y represents a leaving group;
  (ii) combining said precursor complex with at least one activator component;
  (iii) removing said leaving group Y from said precursor complex; and
  (iv) replacing said leaving group Y with at least one replacement moiety.

A fourth aspect of the method for preparing at least one addition polymer comprising the steps of:
  (a) combining:
    (i) at least one catalytic composition according to claim 1; and
    (ii) at least one ethylenically unsaturated monomer; and
  (b) polymerizing said ethylenically unsaturated monomer in the presence of said catalytic composition to form an addition polymer.

Used herein, the following terms have these definitions:
  "Range". Disclosures of ranges herein take the form of lower and upper limits. There may be one or more lower limits and, independently, one or more upper limits. A given range is defined by selecting one lower limit and one upper limit. The selected lower and upper limits then define the boundaries of that particular range. All ranges that can be defined in this way are inclusive and combinable, meaning that any lower limit may be combined with any upper limit to delineate a range.

A "catalytic composition" is a composition including at least one "cationic metal-pair complex", wherein the cationic metal-pair complex includes at least one "metal atom pair". Each metal atom pair includes a single "first metal atom" represented by the symbol "$M^1$" ("metal atom $M^1$") and a single "second metal atom" represented by the symbol "$M^2$" ("metal atom $M^2$").

The "through-space internuclear metal atom pair distance" (referred to interchangeably, herein, as "through-space internuclear distance") for a metal atom pair of a cationic metal-pair complex is the distance between the nucleus of the first metal atom $M^1$ of a metal atom pair and the nucleus of the second metal atom $M^2$ of that pair. This through-space internuclear distance is equal to or less than the "through-bond internuclear distance", which is the distance traced along connecting bonds. For example, if a metal-metal bond exists between $M^1$ and $M^2$ of a metal atom pair, the through-space internuclear distance and the metal-metal through-bond distance are the same. If this metal atom pair also had a third ligand as a bridging moiety between $M^1$ and $M^2$, the distance from $M^1$ to $M^2$ along the bonds of that third ligand would be greater than the through-space distance.

The "through-space internuclear metal atom pair distance" for a metal pair of a cationic metal-pair complex may be determined using quantum chemical calculation methods known to those of ordinary skill in the art of computational chemistry. For example, a quantum chemical calculation method suitable for use with the present invention includes density functional methods such as Jaguar™ software, Version 5.0. For a given cationic metal-pair complex, one of ordinary skill in the art of computational chemistry can utilize accepted rules of chemical connectivity, the "LACVP basis set", and the "B3LYP functional" to calculate the interatomic metal-metal distance (i.e., the through-space internuclear metal atom pair distance) for a metal pair of that cationic metal-pair complex. Using Jaguar™ software, Version 5.0, the structure of the cationic metal-pair complex is geometry optimized, using as a starting point a structure having the proper atomic connectivity. The metal-metal interatomic distance for a metal pair of that complex (i.e., the "through-space internuclear metal pair distance") can then be determined from the atomic Cartesian coordinates of the geometry optimized structure. Jaguar™ software, Version 5.0. and the Jaguar 5.0 Operating Manual, January 2003, are available from Schrömdinger, L. L. C., 120 West $45^{th}$ Street, $32^{nd}$ Floor, New York, N.Y. 10036.

The first metal atom and the second metal atom of a metal atom pair may further exhibit "cooperativity" during the polymerization of ethylenically unsaturated monomers, wherein cooperativity means that the first metal atom will positively influence the ability of the second metal atom to polymerize ethylenically unsaturated monomer, or the second metal atom will positively influence the ability of the first metal atom to polymerize ethylenically unsaturated monomer, or both. In such embodiments, therefore include a polymerization system including the catalytic composition of the present invention and at least one ethylenically unsaturated monomer, wherein the first metal atom and the second metal atom exhibit cooperativity during catalysis of the polymerization of ethylenically unsaturated monomers. Not wishing to be bound by any particular theory, it is thought that, when the two metals of a metal atom pair exhibit cooperativity, that cooperativity may, for example, take the form wherein a metal of the pair favorably modifies the electronic, steric, or other spatial environment of the other metal of the pair, or of the inserting ethylenically unsaturated monomer, or of the portion of any polymer chain growing from, or otherwise associated with, the metal atom pair. In certain embodiments, a single ethylenically unsaturated monomer may become attached to, or otherwise associated with, each of the members of a metal atom pair, either sequentially or simultaneously, during its incorporation into a polymer by insertion polymerization catalyzed by that metal atom pair.

A "coordination bond" can be a bond between a "coordination site" of a first metal atom, $M^1$, and any one of the following: first ligand; bridging moiety; first anionic hydrocarbyl radical; first labile ligand; or metal atom $M^2$. A "coordination bond" can also be a bond between a "coordination site" of a second metal atom, $M^2$, and any one of the following: second ligand; bridging moiety; second anionic hydrocarbyl radical; second labile ligand; or metal atom $M^1$. A set of coordination bonds is represented by the symbol "A", having a superscript denoting the position of that bond in the "cationic metal-pair complex formula" (vide infra) and a subscript denoting the number of coordination bonds.

The term "ligand" has its usual meaning in organometallic chemistry. A "ligand" is a moiety bearing one or more "donor sites", wherein a "donor site" is an electron rich site (e.g., lone electron pair) capable of forming a "coordination bond" with a metal atom by donating electron density to an unoccupied (i.e., electron deficient) "coordination site" on that metal atom. The ligand is said to be "occupying that coordination site" on that metal atom. Alternatively, the ligand is said to be "coordinately bound" to the metal atom. When one or more coordination bonds exist between a ligand and a metal atom, both that ligand and that metal atom are said to be "participating" in each of those coordination bonds.

A "neutral electron donor ligand" is any ligand which, when removed from a metal atom (i.e., one or more coordination bonds are broken) in its closed shell electron configuration, has a neutral charge. For example, triphenylphosphine is a neutral electron donor ligand.

A "monodentate ligand" is a ligand bearing a single "donor site". For example, triphenylphosphine is a monodentate ligand, the phosphorus lone electron pair of which is a donor site capable of coordinating to (i.e., occupying a coordination site of) a metal atom.

A "bidentate ligand" is a ligand bearing two donor sites. For example, 1,2-bis(diphenylphosphino)ethane is a bidentate ligand. Each of the two donor sites of a bidentate ligand may be able to form a coordination bond to the same metal atom. Alternatively, one donor site of a bidentate ligand may form a coordination bond to one metal atom, while the other donor site of the same bidentate ligand may form a coordination bond to a different metal atom.

A "multi-dentate ligand" bears two or more donor sites, each of which is capable of coordinating to a metal atom. For example, pentamethyldiethylenetriamine is a multi-dentate ligand having three such donor sites. Provided that such considerations as steric and electronic factors allow it, each of the donor sites of a multi-dentate ligand may be able to form a coordination bond to the same metal atom. Alternatively, at least one donor site of a multi-dentate ligand may form a coordination bond to one metal atom, while at least one other donor site of the same multi-dentate ligand may form a coordination bond to a different metal atom, and each of those two metal atom could be in the same metal-atom pair, or in two different metal-atom pairs of the complex that contains one or more metal-atom pairs. A "bidentate ligand" is a special case of a "multi-dentate ligand".

It is further possible that fewer than all of the donor sites of a ligand may actually participate in coordination bonds. Therefore, for any ligand, the "effective number of donor sites" of that ligand is equal to the number of donor sites actually participating in coordination bonds. It follows that an "effectively monodentate ligand" is a ligand having a total of one donor site participating in a coordination bond. Similarly, for example, "effectively bidentate", "effectively tridentate", "effectively tetradentate", "effectively pentadentate", and "effectively hexadentate" ligands have, respectively, two, three, four, five, and six donor sites participating in coordination bonds. As a further example, pentamethyldiethylenetriamine has three amine lone electron pairs as donor sites, and is therefore a tridentate ligand. If only two of the amine lone electron pairs of this triamine were participating in coordination bonds with one metal, or two metals of a metal atom pair, the triamine would be effectively bidentate with respect to that metal atom pair. If only one of those electron pairs were participating in a coordination bond with a metal, the triamine would be effectively monodentate. As a further example, the allyl anion is effectively monodentate in its $\eta^1$-allyl form, but effectively bidentate in its $\eta^3$-allyl form.

A "first ligand" may be any ligand capable of participating in one or more coordination bonds with metal atom $M^1$ of a metal atom pair, while not simultaneously participating in a coordination bond with metal atom $M^2$ of that same metal atom pair.

A "second ligand" may be any ligand capable of participating in one or more coordination bonds with metal atom $M^2$ of a metal atom pair, while not simultaneously participating in a coordination bond with metal atom $M^1$ of that same metal atom pair.

A "third ligand" of the present invention may be any ligand capable of participating, simultaneously, in at least one coordination bond with each of metal atom $M^1$ and metal atom $M^2$, of the same metal atom pair.

A "labile neutral electron donor ligand" is any neutral electron donor ligand which is not strongly bound to a metal atom (e.g., $M^1$ or $M^2$), and is easily displaced therefrom. The terms "labile neutral electron donor ligand" and "labile ligand" are used interchangeably herein.

A "first labile ligand" is a labile ligand capable of participating in a coordination bond with metal atom $M^1$, while not simultaneously participating in a coordination bond with metal atom $M^2$.

A "second labile ligand" is a labile ligand capable of participating in a coordination bond with metal atom $M^2$, while not simultaneously participating in a coordination bond with metal atom $M^1$.

An anionic ligand, is any ligand which, when removed from a metal atom (e.g., $M^1$ or $M^2$) in its closed shell electron configuration, has a negative charge.

A "multi-(metal pair) coupling moiety", referred to herein, interchangeably, as a "pair-coupling moiety" is any multi-dentate moiety capable of participating, simultaneously, in at least one coordination bond with each of at least two metal atom pairs of a single complex. A "pair-coupling moiety" includes multiple donor sites having constraints (for example, steric constraints, electronic constraints, or both) allowing one or more of those donor sites to participate in coordination bonds with one metal pair while, simultaneously, one or more of its other donor sites is participating in coordination bonds with another metal pair. Though not wishing to be bound by any particular theory, it is believed that the number of metal pairs that can simultaneously participate in one or more coordination bonds with the same pair-coupling moiety is governed by such considerations as, for example: steric constraints of the pair-coupling moiety; electronic constraints of the donor sites of the pair-coupling moiety; electronic and spatial characteristics of metal atoms $M^1$ and $M^2$ within and, where there are multiple metal-atom pairs in the same complex, between metal atom pairs; steric and electronic characteristics of any other first ligand, second ligand, bridging moiety, first anionic hydrocarbyl containing radical, second anionic hydrocarbyl containing radical, first labile ligand, second labile ligand, or leaving group that is simultaneously participating in a coordination bond, or bonds, with either metal atom $M^1$ or $M^2$ of each metal atom pair; the mole ratios of the pair-coupling moiety to the metal pairs; and the accessibility of donor sites (e.g., a pair-coupling moiety may be a porous polymeric structure, wherein some donor sites may be inaccessible to metal atom pairs). Further, the maximum number of metal atom pairs that may possibly be coordinately bound to a single pair-coupling moiety is equal to the number of donor sites on that pair-coupling moiety. However, one or more of the constraints listed supra may intervene to limit the number of metal atom pairs that are actually bound to a single pair-coupling moiety to a number less than that maximum value. It may also be the case that a single pair-coupling moiety may participate in multiple coordination bonds with one or both of metal atoms $M^1$ and $M^2$ of a single metal pair. There is no particular limit on the size of the pair-coupling moiety. For example, the pair-coupling moiety may be a macroreticular resin bearing donor sites (vide infra), a crown ether, or other macrostructure bearing multiple donor sites.

A "pair-coupling moiety" is a moiety capable of participating in coordination bonds with two or more metal atom pairs of a complex of the present invention, provided, of course, that the complex has at least two metal atom pairs and that constraints such as those just enumerated allow coordination bonds to multiple metal atom pairs. The following complexes of the present invention may contain one or more pair-coupling moieties: cationic metal-pair complex; and precursor complexes, including full-(metal pair) precursor complex; first semi-(metal pair) precursor complex; and second semi-(metal pair) precursor complex. When two or more metal atom pairs are present in a complex of the present invention: all of metal atoms $M^1$ may be identical (e.g., all might be Ni); all of metal atoms $M^2$ may be identical; metal atom $M^1$ may differ from pair to pair (e.g., one might be Ni, while another would be Pd); and metal atom $M^2$ may differ from pair to pair. In the case of first and second semi-(metal pair) complexes, either metal atom $M^1$ or $M^2$, but not both, will be present in each pair of the semi-(metal pair) complex. A "pair-coupling moiety" may be any of the following: first ligand, second ligand, third ligand, first labile ligand, second labile ligand, first hydrocarbyl radical, second hydrocarbyl radical, or combinations thereof.

A "weakly coordinating anion" ("WCA") is an anion which is only weakly associated with the cationic metal-pair complex. The WCA is sufficiently labile to be displaced by a neutral Lewis base, solvent or monomer. More specifically, the WCA functions as a stabilizing anion to the cationic metal-pair complex and does not transfer sufficient electron density to the cationic metal-pair complex to form a neutral product. The WCA is relatively inert in that it is non-oxidative, non-reducing, and non-nucleophilic.

A "cationic metal-pair complex" is a complex represented by the following "cationic metal-pair complex formula" ("formula I"):

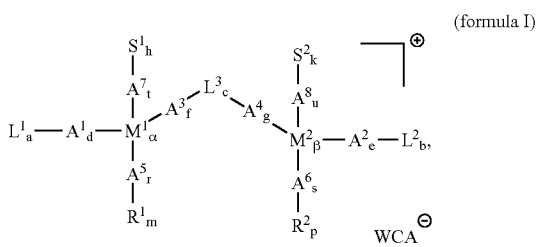

(formula I)

and the following symbols and subscripts have these meanings in the cationic metal-pair complex formula:

The symbols "$M^1$" and "$M^2$" represent, respectively, a first metal atom of a metal atom pair and a second metal atom of a metal atom pair. The cationic metal-pair formula subscript "α" on the symbol "$M^1_\alpha$", indicates whether metal atom $M^1$ is present in (α=1) or absent from (α=0) a metal atom pair of a cationic metal-pair complex. The cationic metal-pair formula subscript "β" on the symbol "$M^2_\beta$", indicates whether metal atom $M^2$ is present in (β=1) or absent from (β=0) a metal atom pair of a cationic metal-pair complex. Because both of metal atoms $M^1$ and $M^2$ must be present in any metal atom pair of a cationic metal-pair complex, the following relationship exists: α=β=1.

The symbol "$L^1$" represents a "set of first ligands", wherein a "first ligand" is a ligand coordinately bound to metal atom $M^1$, but not coordinately bound to metal atom $M^2$. This set of first ligands may, interchangeably, be referred to as "set $L^1$". The cationic metal pair-complex formula subscript "a", of "$L^1_a$", equals either the integer 0 or 1. When "a=1, set $L^1$ includes one or more first ligands. When "a"=0, set $L^1$ is "empty". When a ligand set is empty, that ligand set contains no ligands. For example, when "a"=0, set $L^1$ contains no first ligands.

The symbol "$L^2$" represents a "set of second ligands", wherein a "second ligand" is a ligand coordinately bound to metal atom $M^2$, but not coordinately bound to metal atom $M^1$. This set of second ligands may, interchangeably, be referred to as "set $L^2$". The cationic metal pair-complex formula subscript "b", of "$L^2_b$", equals either 0 or 1. When "b"=1, set $L^2$ includes one or more second ligands. When "b"=0, set $L^2$ is empty.

The symbol "$L^3$" represents a "set of bridging moieties". A "bridging moiety" is a moiety coordinately bound to both metal atom $M^1$ and metal atom $M^2$ of the same metal atom pair. A metal-metal bond is a special case of a bridging moiety wherein the moiety is the bond itself, and involves no other atoms beyond the two metal atoms of the metal-metal bond. This set of bridging moieties may, interchangeably, be referred to as "set $L^3$". The cationic metal pair-complex formula subscript "c", of "$L^3_c$", equals 1 in the cationic metal-pair complex formula, indicating that set $L^3$ includes one or more bridging moieties.

The symbol "$R^1$" represents a "set of first anionic hydrocarbyl containing radicals" coordinately bound to metal atom $M^1$, but not to metal atom $M^2$. This set of first anionic hydrocarbyl containing radicals may, interchangeably, be referred to as "set $R^1$". Herein, the term "first hydrocarbyl radical" is used interchangeably with the term "first anionic hydrocarbyl containing radical". The cationic metal pair-complex formula subscript "m", of "$R^1_m$", equals either 0 or 1. When "m"=1, set $R^1$ includes one or more first hydrocarbyl radicals. When "m"=0, set $R^1$ is empty.

The symbol "$R^2$" represents a "set of second anionic hydrocarbyl containing radicals" coordinately bound to metal atom $M^2$, but not to metal atom $M^1$. This set of second anionic hydrocarbyl containing radicals may, interchangeably, be referred to as "set $R^2$". Herein, the term "second hydrocarbyl radical" is used interchangeably with the term "second anionic hydrocarbyl containing radical". The subscript "p", of "$R^2_p$", equals either the integer 0 or 1. When subscript "p"=1, set $R^2$ includes one or more second hydrocarbyl radicals. When subscript "p"=0, set $R^2$ is empty. The relationship that, if one of the sets $R^1$ and $R^2$ is empty, then the other set must contain at least one hydrocarbyl radical is represented by the following relationship: $1 \leq m+p \leq 2$.

It is also possible for a hydrocarbyl radical to simultaneously participate in at least one coordination bond of each of first metal atom, $M^1$, and second metal atom, $M^2$, of the same metal atom pair. This case is described herein as a "third anionic hydrocarbyl containing radical", alternatively "third hydrocarbyl radical". A "third hydrocarbyl radical" is a special case of a "bridging moiety", $L^3$.

An "anionic hydrocarbyl containing radical" (interchangeably, "hydrocarbyl radical") is any hydrocarbyl radical which, when removed from a metal atom (e.g., $M^1$ or $M^2$) in its closed shell electron configuration, has a negative charge. In any complex of the present invention in which they both are present, a first hydrocarbyl radical and a second hydrocarbyl radical may be the same or different. When a set $R^1$ contains more than one first hydrocarbyl radical, those first hydrocarbyl radicals may all be the same, or one or more may be different from at least one other first hydrocarbyl radical of that set $R^1$. When a set $R^2$ contains more than one second hydrocarbyl radical, those second hydrocarbyl radicals may all be the same, or one or more may be different from at least one other second hydrocarbyl radical of that set $R^2$.

The symbol "$S^1$" represents a "set of first labile ligands", wherein a "first labile ligand" is a labile ligand coordinately bound to metal atom $M^1$, but not coordinately bound to metal atom $M^2$. This set of first labile ligands may, interchangeably, be referred to as "set S'". The cationic metal pair-complex formula subscript "h", of "$S^1_h$", equals either 0 or 1. When "h"=1, set $S^1$ includes one or more first labile ligands. When "h"=0, set $S^1$ is "empty". When a labile ligand set is empty, that labile ligand set contains no ligands. For example, when "h"=0, set $S^1$ is empty. When set $S^1$ contains more than one first labile ligand, those first labile ligands may all be the same, or one or more may be different from at least one other first labile ligand of that set $S^1$.

The symbol "$S^2$" represents a "set of second labile ligands", wherein a "second labile ligand" is a labile ligand coordinately bound to metal atom $M^2$, but not coordinately bound to metal atom $M^1$. This set of second labile ligands may, interchangeably, be referred to as "set $S^2$". The cationic metal pair-complex formula subscript "k", of "$S^2_k$", equals either 0 or 1. When "k"=1, set $S^2$ includes one or more second labile ligands. When "k"=0, set $S^2$ is empty. When a set $S^2$ contains more than one second labile ligand, those second labile ligands may be all be the same, or one or more may be different from at least one other second labile ligand of that set $S^2$. In any cationic metal-pair complex of the present invention in which they both are present, a first labile ligand and a second labile ligand may be the same or different.

It is also possible for a labile ligand to simultaneously participate in at least one coordination bond of each of first metal atom, $M^2$, and second metal atom, $M^2$, of the same metal atom pair. This case is described herein as a "third labile ligand". A "third labile ligand" is a special case of a "bridging moiety", $L^3$.

The symbol "$A^1$" represents a set of coordination bonds between any first ligands of set $L^1$ and first metal atom, $M^1$ of a metal atom pair of the cationic metal-pair complex.

The symbol "$A^2$" represents a set of coordination bonds between any second ligands of set $L^2$ and second metal atom, $M^2$ of a metal atom pair of the cationic metal-pair complex.

The symbol "$A^3$" represents a set of coordination bonds between any bridging moieties of set $L^3$ and first metal atom, $M^1$ of a metal atom pair of the cationic metal-pair complex.

The symbol "$A^4$" represents a set of coordination bonds between any bridging moieties of set $L^3$ and second metal atom, $M^2$ of a metal atom pair of the cationic metal-pair complex.

The symbol "$A^5$" represents a set of coordination bonds between any first hydrocarbyl radicals of set $R^1$ and first metal atom, $M^1$ of a metal atom pair of the cationic metal-pair complex.

The symbol "$A^6$" represents a set of coordination bonds between any second hydrocarbyl radicals of set $R^2$ and second metal atom, $M^2$ of a metal atom pair of the cationic metal-pair complex The symbol "$A^7$" represents a set of coordination bonds between any first labile ligands of set $S^1$ and first metal atom, $M^1$ of a metal atom pair of the cationic metal-pair complex.

The symbol "$A^8$" represents a set of coordination bonds between any second labile ligands of set $S^2$ and second metal atom $M^2$ of a metal atom pair of the cationic metal-pair complex.

Any of the sets of coordination bonds represented by the symbol "A" may, interchangeably, be referred to as "set A". For example, the set of coordination bonds represented by the symbol "$A^1$" may, interchangeably, be referred to as "set $A^1$".

If any of sets $L^1$, $L^2$, $R^1$, $R^2$, $S^1$, and $S^2$ is empty, the cation formula subscript of any symbol "A" representing any coordination bonds directly associated with that set will equal 0. For example, if set $L^1$ is empty, "a" of "$L^1_a$" equals 0, and "d" of "$A^1_d$", also equals 0. It follows that, if any of cationic metal pair-complex formula subscripts "a", "b", "h", "k", "m", and "p" equal 0, then the corresponding cationic metal pair-complex formula subscripts "d", "e", "t", "u", "r", and "s" will, respectively, equal 0. These relationships also exist among the precursor formula subscripts of the "precursor complex formula" (vide infra).

If any of sets $L^1$, $L^2$, $L^3$, $R^1$, $R^2$, $S^1$, and $S^2$ is occupied, i.e., contains at least one member of its set, the cationic metal pair-complex formula subscript of any symbol "A", representing any coordination bonds directly associated with a member of that set, will equal at least 1. That is, for any of sets $L^1$, $L^2$, $L^3$, $R^1$, $R^2$, $S^1$, and $S^2$ that are occupied, the corresponding cationic metal pair-complex formula subscripts d, e, f, g, r, s, t, or u will, respectively, equal at least 1. For example, if set $L^1$ of a "cationic metal-pair complex" is occupied, "a" of "$L^1_a$," equals 1, and "d" of "$A^1_d$", equals at least 1. Further, if any of sets $L^1$, $L^2$, $L^3$, $R^1$, $R^2$, $S^1$, and $S^2$ is occupied, and the cationic metal pair-complex formula subscript of a symbol "A" representing coordination bonds directly associated with a member, or members, of that set equals at least 2, the plural coordination bonds indicated by that subscript may all emanate from a single member of that set, or, alternatively, emanate from more than one member of that set. For example, if "e", of "$A^2_e$", equals the integer 3, then set $L^2$ may contain one, two, or three second ligands.

In this example, set $L^2$ may contain any of these combinations: three effectively monodentate second ligands (vide supra); one effectively monodentate second ligand and one effectively bidentate second ligand; or one effectively tridentate second ligand.

When a "metal-metal bond" exists between first metal atom, $M^1$, and second metal atom, $M^2$, of a metal atom pair of a cationic metal-pair complex, the presence of that metal-metal bond is indicated in the cationic metal-pair complex formula by incrementing both of subscripts "f, and "g" by 1. In this specific case of a metal-metal bond, the combination of an $A^3$ bond and an $A^4$ bond represents one single bond because there exist no atoms in the bridging moiety, that is, the electron cloud of the bond between metal atom $M^1$ and metal atom $M^2$ is the bridging moiety. This same formalism, wherein both subscripts "f" and "g" are incremented by 1 to indicate a metal-metal bond, holds when a metal-metal bond exists between a first metal atom, $M^1$, and a second metal atom, $M^2$, of a "precursor complex" of the present invention (i.e., when the precursor complex is a full-(metal pair) precursor complex).

The "cationic metal pair-complex formula subscripts" have these values which are either positive integers or zero: a, b, h, k, m, and p are selected from 0 or 1; $\alpha$, $\beta$, and c each equal 1; d, e, r, s, t, and u are selected from 0, 1, 2, or 3; f and g are selected from 1, 2, 3, or 4; $0 \leq d+e \leq 5$; $1 \leq m+p \leq 2$; $1 \leq r+s \leq 5$; $0 \leq t+u \leq 5$; $2 \leq f+g \leq 7$; the sum d+f+r+t=4; and the sum e+g+s+u=4.

A "precursor complex" is a complex according to the following "precursor complex formula" ("formula II"):

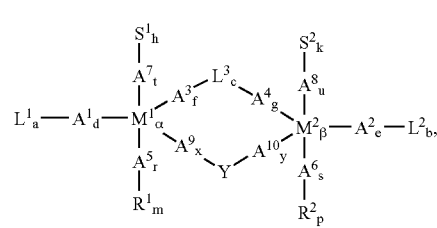

(formula II)

Symbols "$M^1$" "$M^2$", "$R^1$", "$R^2$", "$L^1$", "$L^2$", "$L^3$", "$S^2$", and "$S^2$", of the precursor complex formula" have, respectively, the same meaning as the symbols $M^1$, $M^2$, $R^1$, $R^2$, $L^1$, $L^2$, $L^3$, $S^1$, and $S^2$ of the "cationic metal-pair complex formula".

Symbols "$A^1$", "$A^2$" "$A^3$", "$A^4$", "$A^5$", "$A^6$", "$A^7$", and "$A^8$", of the "precursor complex formula" have, respectively, the same meaning as the symbols $A^1$, $A^2$, $A^3$, $A^4$, $A^5$, $A^6$, $A^7$, and $A^8$ of the "cationic metal-pair complex formula".

Although both $M^1$ and $M^2$ of the at least one metal atom pair of the "cationic metal-pair complex" are always present in the "cationic metal-pair complex", one member of the at least one metal atom pair of the "precursor complex" may be absent. For that reason precursor formula subscripts "$\alpha$" and "$\beta$" have, respectively been added to "$M^1$" and "$M^2$" in the "precursor complex formula". The precursor formula subscript "$\alpha$" on the symbol "$M^1_\alpha$", indicates whether metal atom $M^1$ is present in ($\alpha$=1) or absent from ($\alpha$=0) a metal atom pair of a precursor complex. The precursor formula subscript "$\beta$" on the symbol "$M^2_\beta$", indicates whether metal atom $M^2$ is present in ($\beta$=1) or absent from ($\beta$=0) a metal atom pair of a precursor complex. Because either one or both of metal atoms $M^1$ and $M^2$ must be present in any metal atom pair of a precursor complex, the following relationship exists: $1 \leq \alpha+\beta \leq 2$.

Symbol "Y" represents a leaving group of the precursor complex.

A "leaving group" is a moiety capable of being removed from the precursor complex of the present invention by the action of an "activator component".

Symbol "$A^9$" represents a set of coordination bonds between leaving group Y and first metal atom, $M^1$ of a metal atom pair of a precursor complex.

Symbol "$A^{10}$" represents a set of coordination bonds between leaving group Y and second metal atom, $M^2$ of a metal atom pair of a precursor complex.

An "activator component" is a moiety capable of removing a leaving group Y from a "coordination site" of: metal atom $M^1$ of a precursor complex; metal atom $M^2$ of the precursor complex; or each of metal atom $M^1$ and metal atom $M^2$ of the precursor complex.

A "full-(metal-pair) precursor complex" is a precursor complex according to the precursor complex formula (formula II) wherein the precursor formula subscripts have these values: a, b, h, k, x, and y are selected from 0 or 1; $\alpha$, $\beta$, and c each equal 1; d, e, r, s, t, and u are selected from 0, 1, 2, or 3; f and g are selected from 1, 2, 3, or 4; $1 \leq m+p \leq 2$; $0 \leq d+e \leq 4$; $1 \leq r+s \leq 5$; $0 \leq t+u \leq 4$; $1 \leq x+y \leq 2$; $2 \leq f+g \leq 6$; the sum d+f+r+t+x=4, and the sum e+g+s+u+y=4;

A "first semi-(metal-pair) precursor complex" is a precursor complex according to the precursor complex formula (formula II) wherein the precursor formula subscripts have these values: $\alpha$ and x each equal 1; $\beta$, b, c, k, p, e, f, g, s, u, and y each equal 0; a, h, and m are selected from 0 or 1; d, r, and t are selected from 0, 1, 2, or 3; and the sum d+f+r+t+x=4.

A "second semi-(metal pair) precursor complex" is a precursor complex according to the precursor complex formula (formula II) wherein the precursor formula subscripts have these values: $\beta$ equals 1; $\alpha$, a, c, h, m, d, f, g, r, t, x, and y each equal 0; b, k, and p are selected from 0 or 1; e is selected from 0, 1, 2, 3, or 4; s and u are selected from 0, 1, 2, or 3; and the sum e+g+s+u+y=4.

When a first semi-(metal-pair) precursor complex and a second semi-(metal-pair) precursor complex are used to prepare a cationic metal-pair complex in the method of preparation of the cationic metal-pair complex of the present invention, that first semi-(metal-pair) precursor complex and that second semi-(metal-pair) precursor complex are related in the following ways:

the sum of "m" of said first semi-(metal pair) complex+ "p" of said second semi-(metal pair) complex is selected from 1 or 2;

at least one said first ligand of the first semi-(metal pair) complex or at least one of the second ligand of said second semi-(metal pair) precursor complex has at least one donor site available to fill a metal coordination site vacated by said leaving group Y of said first semi-(metal pair) precursor complex.

A "replacement moiety" is any moiety capable of becoming any of the following: first ligand, second ligand, first hydrocarbyl-containing radical, second hydrocarbyl-containing radical, first labile ligand, second labile ligand, and bridging moiety. A "replacement moiety" is capable of replacing a leaving group during or after removal of that leaving group from a full-(metal pair) precursor comple or a first semi-(metal pair) precursor complex.

A "bridging moiety" of set $L^3$ may be a third ligand, bridging labile ligand, bridging anionic hydrocarbyl radical, bridging hemi-labile ligand, or metal-metal bond.

The term "ethylenically unsaturated monomer" refers to a molecule having one or more carbon-carbon double bonds, and capable of insertion addition polymerization. The term "monoethylenically unsaturated monomer" refers to an ethylenically unsaturated monomer having one carbon-carbon double bond capable of insertion addition polymerization. The term "multiethylenically unsaturated monomer" refers to an ethylenically unsaturated monomer having two or more carbon-carbon double bonds capable of insertion addition polymerization.

The term "non-polar olefinic monomer" (alternatively "non-polar olefin") refers to an ethylenically unsaturated monomer consisting exclusively of hydrogen and carbon atoms. The non-polar olefinic monomers of the present invention are any non-polar olefinic monomers capable of being polymerized using the cationic metal-pair complex of the present invention to form "poly(non-polar olefin)s" or "poly[(polar olefin)-co-(non-polar olefin)]s".

The term "polar olefinic monomer" (alternatively "polar olefin") refers to an ethylenically unsaturated monomer including at least one atom other than carbon or hydrogen. The polar olefinic monomers of the present invention are any polar olefinic monomers capable of being polymerized using the cationic metal-pair complex of the present invention to form "poly(polar olefin)s" or "poly [(polar olefin)-co-(non-polar olefin)]s".

The term "(meth)acryl" refers to both "acryl" and "methacryl". For example, "butyl (meth)acrylate" refers to both "butyl acrylate" and "butyl methacrylate". "(Meth)acryl" type monomers are examples of the "polar olefinic monomer" of the present invention.

An "addition polymer" is a polymer capable of being prepared by addition polymerization, and selected from the group consisting of poly(non-polar olefin), poly(polar olefin), poly[(polar olefin)-co-(non-polar olefin)], and combinations thereof.

A "poly(non-polar olefin)" is a polymer comprising one or more non-polar olefinic monomers, as polymerized units. As such, a "poly(non-polar olefin)" may be a homopolymer or a copolymer, and the copolymer may be, for example, a random, alternating, or block copolymer.

A "poly(polar olefin)" is a polymer comprising, as polymerized units, one or more polar olefinic monomers. As such, a "poly(polar olefin)" may be a homopolymer or a copolymer, and the copolymer may be, for example, a random, alternating, or block copolymer.

A "poly[(polar olefin)-(non-polar olefin)]" is a copolymer comprising one or more non-polar olefinic monomers and one or more polar olefinic monomers, as polymerized units, and the copolymer may be, for example, a random, alternating, or block copolymer. The addition polymer of the present invention is a polymer selected from the group consisting of: poly(non-polar olefin), poly(polar olefin), poly[(polar olefin)-(non-polar olefin)], and combinations thereof.

The following expressions describe the molecular weight of a collection of polymer chains "weight average molecular weight", "$M_w$" and the "number average molecular weight", "$M_n$". These are defined as follows:

$$M_w = \Sigma(W_i M_i)/\Sigma W_i = \Sigma(N_i M_i^2)/\Sigma N_i M_i$$

$$M_n = \Sigma W_i/\Sigma(W_i/M_i) = \Sigma(N_i M_i)/\Sigma N_i$$

where:

$M_i$=molar mass of $i^{th}$ component of distribution
$W_i$=weight of $i^{th}$ component of distribution
$N_i$=number of chains of $i^{th}$ component and the summations are over all the components in the distribution. $M_w$ and $M_n$ are typically computed from the MWD as measured by Gel Permeation Chromatography (see the Experimental Section). The value for "$M_w/M_n$" is referred to as the "MWD polydispersity".

The "average particle size" determined for a collection of polymer particles, varies somewhat according to method of determination (e.g., by DCP or BI-90, as described herein below), but is approximately, or identically, "the weight average particle size", "$d_w$", also described herein below.

Herein, the term "particle size distribution" and the acronym "PSD" are used interchangeably. Used herein, a "PSD polydispersity" is a description of the distribution of particle sizes for the plural polymer particles of the invention. PSD polydispersity is calculated from the weight average particle size, $d_w$, and the number average particle size, $d_n$, according to the expressions:

PSD Polydispersity=$(d_w)/(d_n)$, where $d_n = \Sigma n_i d_i / \Sigma n_i$ $d_w = \Sigma n_i d_i d_i / \Sigma n_i d_i$, and where $n_i$ is the number of particles having the particle size $d_i$ A "monodisperse" distribution (herein, MWD or PSD) refers to a distribution having a polydispersity of exactly 1.

A "supercritical fluid" ("SCF") is a substance above its critical temperature and critical pressure (i.e., its "critical point"). For carbon dioxide, the critical temperature is 31° C. and the critical pressure is 1070 psi. Above the critical point of a fluid, further compression does not cause formation of a liquid (see *Chem. Rev.*, 1999, 99, pp. 565–602.

Each metal atom pair of the cationic metal-pair complex of the present invention includes a single "first metal atom" represented by the symbol "$M^1$" ("metal atom $M^1$") and a single "second metal atom" represented by the symbol "$M^2$" ("metal atom $M^2$"). The first metal atom has four (4) occupied coordination sites, and is a metal atom selected from: the group consisting of nickel, palladium, platinum, copper, silver, gold, iron, cobalt, rhodium, chromium, and manganese; the group consisting of nickel, palladium, copper, iron, and cobalt; or the group consisting of nickel and palladium. The second metal atom also has four (4) occupied coordination sites, and is a metal atom selected from: the group consisting of nickel, palladium, platinum, copper, silver, gold, iron, cobalt, rhodium, chromium, and manganese; the group consisting of nickel, palladium, copper, iron, and cobalt; or the group consisting of nickel and palladium. The first metal atom and the second metal atom may be the same element, or different elements.

Because the cationic metal-pair complex of the present invention is made from the precursor complex of the present invention, it follows that metal atoms $M^1$ and $M^2$ of a cationic metal-pair complex will be, respectively, the same, as metal atoms $M^1$ and $M^2$ of the precursor complex(es), from which that cationic metal-pair complex was made. Therefore, the first metal atom of the precursor complex has four (4) occupied coordination sites, and is a metal atom selected from: the group consisting of nickel, palladium, platinum, copper, silver, gold, iron, cobalt, rhodium, chromium, and manganese; the group consisting of nickel, palladium, copper, iron, and cobalt; or the group consisting of nickel and palladium. The second metal atom of the precursor complex also has four (4) occupied coordination sites, and is a metal atom selected from: the group consisting of nickel, palladium, platinum, copper, silver, gold, iron, cobalt, rhodium, chromium, and manganese; the group consisting of nickel, palladium, copper, iron, and cobalt; or the group consisting of nickel and palladium. The first metal atom and the second metal atom may be the same element, or different elements. A precursor complex may be a full-(metal pair) precursor complex, a first semi-(metal pair) precursor complex, or a second semi-(metal pair) precursor complex. Both first metal atom, $M^1$, and second metal atom, $M^2$, are present in the full-(metal pair) precursor complex. In contrast, only first metal atom, $M^1$, is present in a first semi-(metal pair) precursor complex, and only second metal atom, $M^2$, is present in a second semi-(metal pair) precursor complex.

The combined molar percentage of first metal atom, $M^1$, and second metal atom, $M^2$, present in the cationic metal-pair complex of the present invention, based on the total of all $M^1$-type metal atoms and $M^2$-type metal atoms present in any catalyst complexes of the catalytic composition of the present invention, is: at least 25, at least 50, at least 75, at least 90, or at least 95; and no more than 100; no more than 99; or no more than 97, based on the total moles of $M^1$ and $M^2$ The "through-space internuclear distance" for a metal atom pair of the present invention is: at least 1.5 Angstroms (1 Å=0.0001 micron=$1 \times 10^{-10}$ meter), at least 2 Å, at least 3 Å, or at least 4 Å; and no more than 20 Å, no more than 15 Å, no more than 10 Å, or no more than 6 Å.

Any monodentate or multidentate ligand may be a first ligand of set $L^1$ or a second ligand of set $L^2$ of the present invention, provided that constraints (e.g., electronic, steric, and other spatial constraints) which exist for the ligand in any given cationic metal-pair complex, or precursor complex allow that monodentate or multidentate ligand to participate in at least one coordination bond with the corresponding metal atom ($M^1$ for ligand set $L^1$; and $M^2$ for ligand set $L^2$) of a metal-atom pair.

When both set $L^1$ and set $L^2$ are present in the same cationic metal-pair complex or in the same precursor complex, the first and second ligands that are, respectively, members of those sets may be identical or different ligands within a given set (i.e., $L^1$, $L^2$), and the ligands of set $L^1$ may be the same or different from those of set $L^2$. First ligands and second ligands may be, independently, selected from the following non-exhaustive lists of ligand types wherein at least one atom selected from Group 14, 15, 16, and 17 participates in at least one coordination bond of the present invention.

Any multidentate ligand may also be a third ligand of set $L^3$ of the present invention, provided that constraints (e.g., electronic, steric, and other spatial constraints) which obtain for the ligand in any specific cationic metal-pair complex, or full-(metal pair) precursor complex allow that multidentate ligand to simultaneously participate in at least one coordination bond with each of the metals of a metal-atom pair of that complex.

Similarly, lists of labile ligand, hemi-labile ligand, anionic hydrocarbyl containing radical, activator, weakly coordinating anion, diluents, and monomer types, as well as specific example, provided herein are meant to be illustrative and not exhaustive. Further, the ability of a given labile ligand, hemi-labile ligand, or anionic hydrocarbyl containing radical to form a coordination bond with one, or both, metal atoms of a metal atoms pair of a particular cationic metal-pair complex or precursor complex of the present invention, will depend upon the constraints (e.g., electronic, steric, and other spatial constraints) which exist for that labile ligand, hemi-labile ligand, or anionic hydrocarbyl containing radical.

When mono- and multi-dentate ligands are indicated structurally or by chemical name herein, usage may be made of the designation of one or more substituents on a ligand as an "R-group" indicated by a capital "R", with or without a superscript. Although such notation, common in the art of organometallic chemistry and chemistry in general, is retained herein for describing substituents of ligands, it is understood, herein, that these "R-group" notations do not refer to the first or second anionic hydrocarbyl containing radicals of set $R^1$ and set $R^2$, respectively, of the cationic complex, or of the precursor complex, of the present invention. Similarly, it is understood that any R-group notations used herein to describe, for example, substituents of labile ligands, or substituents of hemi-labile ligands, or substituents of activators, or substituents of weakly coordinating anions, or substituents of ethylenically unsaturated monomers, do not refer to the first or second anionic hydrocarbyl containing radicals of set $R^1$ and set $R^2$, respectively, of the present invention.

Representative neutral electron donor ligands include amines, pyridines, organophosphorus containing compounds, and arsines and stibines, of the formula: E(R3)3, wherein E is arsenic or antimony, and R3 is independently selected from hydrogen, linear and branched $C_1$–$C_{10}$ alkyl, $C_5$–$C_{10}$ cycloalkyl, linear and branched $C_1$–$C_{10}$ alkoxy, allyl, linear and branched $C_2$–$C_{10}$ alkenyl, $C_6$–$C_{12}$ aryl, $C_6$–$C_{12}$ aryloxy, $C_6$–$C_{12}$ arylsufides (e.g., PhS), $C_7$–$C_{18}$ aralkyl, cyclic ethers and thioethers, tri(linear and branched $C_1$–$C_{10}$ alkyl)silyl, tri($C_6$–$C_{12}$ aryl)silyl, tri(linear and branched $C_1$–$C_{10}$ alkoxy)silyl, triaryloxysilyl, tri(linear and branched $C_1$–$C_{10}$ alkyl)siloxy, and tri($C_6$–$C_{12}$ aryl)siloxy, each of the foregoing substituents can be optionally substituted with linear or branched $C_1$–$C_5$ alkyl, linear or branched $C_1$–$C_5$ haloalkyl, $C_1$–$C_5$ alkoxy, halogen, and combinations thereof.

Representative pyridines include pyridine, lutidine (including 2,3-; 2,4-; 2,5-; 2,6-; 3,4-; and 3,5-substituted), picoline (including 2-, 3-, or 4- substituted), 2,6-di-t-butylpyridine, and 2,4-di-t-butylpyridine.

Representative arsines include triphenylarsine, triethylarsine, and triethoxysilylarsine.

Representative stibines include triphenylstibine and trithiophenylstibine.

Suitable amine ligands can be selected from amines of the formula $N(R^4)3$, wherein $R^4$ independently represents hydrogen, linear and branched $C_1$–$C_{20}$ alkyl, linear and branched $C_1$–$C_{20}$ haloalkyl, substituted and unsubstituted $C_3$–$C_{20}$ cycloalkyl, substituted and unsubstituted $C_6$–$C_{18}$ aryl, and substituted and unsubstituted $C_7$–$C_{18}$ aralkyl. When substituted, the cycloalkyl, aryl and aralkyl groups can be monosubstituted or multisubstituted, wherein the substituents are independently selected from hydrogen, linear and branched $C_1$–$C_{12}$ alkyl, linear and branched $C_1$–$C_5$ haloalkyl, linear and branched $C_1$–$C_5$ alkoxy, $C_6$–$C_{12}$ aryl, and halogen selected from chlorine, bromine, and fluorine. Representative amines include but are not limited to ethylamine, triethylamine, diisopropylamine, tributylamine, N,N-dimethylaniline, N,N-dimethyl-4-t-butylaniline, N,N-dimethyl-4-t-octylaniline, and N,N-dimethyl-4-hexadecylaniline.

The organophosphorus containing ligands include phosphines, phosphites, phosphonites, phosphinites and phosphorus containing compounds of the formula: P(R3) g [X'(R3) h] 3-g, wherein X' is oxygen, nitrogen, or silicon, R3 is as defined above and each R3 substituent is independent of the other, g is 0, 1, 2, or 3, and h is 1, 2, or 3, with the proviso that when X' is a silicon atom, h is 3, when X' is an oxygen atom h is 1, and when X' is a nitrogen atom, h is 2. When g is 0 and X' is oxygen, any two or 3 of R3 can be taken together with the oxygen atoms to which they are attached to form a cyclic moiety. When g is 3 any two of R3 can be taken together with the phosphorus atom to which they are attached to represent a phosphacycle.

Illustrative phosphine ligands include, but are not limited to trimethylphosphine, triphenylphosphine, tri(trifluoromethylphenyl)phosphine, allyldiphenylphosphine, tris(trimethylsilyl)phosphine, and tris(pentafluorophenyl)phosphine.

The phosphine ligands can also be selected from phosphine compounds that are water soluble thereby imparting the resulting cationic metal-pair complexes with solubility in aqueous media. Illustrative phosphines of this type include but are not limited to ionic or ionizable substituted phosphines such as 4-(diphenylphosphine)benzoic acid, sodium 2-(dicyclohexylphosphino)ethanesulfonate, and 2-(dicyclohexylphosphino)-N,N,N-trimethylethanaminium iodide.

Illustrative phosphite ligands include triethylphosphite, dicyclohexylphosphite, and tri(hexafluoroisopropyl)phosphite.

Illustrative phosphinite ligands include methyl diphenylphosphinite and ethyl diphenylphosphinite.

Illustrative phosphonite ligands include diphenyl phenylphosphonite and diethyl phenylphosphonite.

The multidentate ligands of the present invention include multidentate ligands containing identical or different donor atoms selected from Group 14, 15, 16, and 17 atoms. The substituents covalently bonded to those donor atoms selected from Group 14, 15, 16, and 17 atoms may be any of those bound to the Group 14, 15, 16, and 17 atoms of the monodentate ligands of the present invention.

Illustrative bidentate phosphine ligands of the present invention include (R)-(+)-2,2'-Bis(diphenylphosphino)-1,1'-binaphthy, and 1,2-bis(diphenylphosphino)ethane.

Additional neutral electron ligands useful in the present invention are disclosed in U.S. Pat. No. 6,455,650.

N-heterocyclic carbene ligands, suitable for use with the present invention include saturated and unsaturated substituted and unsubstituted imidazolidine having a structure according to one of structures (A)–(D):

(A)

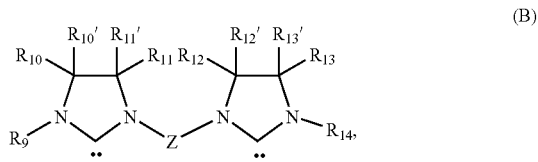

(B)

-continued

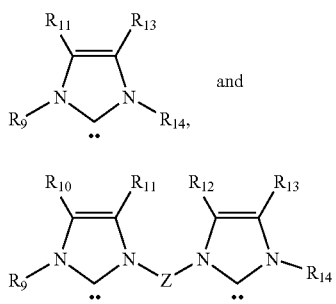

wherein R9, R10, R10', R11, R11', R12, R12', R13, R13' and R14 are each independently a hydrogen or a substituted or unsubstituted substituent selected from C1–C20 alkyl, C2–C20 alkenyl, C2–C20 alkynyl, aryl, C1–C20 carboxylate, C1–C20 alkoxy, C2–C20 alkenyloxy, C2–C20 alkynyloxy, aryloxy, C2–C20 alkoxycarbonyl, C1–C20 alkylthio, C1–C20 alkylsulfonyl, C1–C20 alkylsulfinyl, and silyl; and connecting group Z may be selected from C1–C20 alkyl, aryl, C1–C20 carboxylate, C1–C20 alkoxy, C2–C20 alkenyloxy, C2–C20 alkynyloxy, aryloxy, C2–C20 alkoxycarbonyl, C1–C20 alkylthio, C1–C20 alkylsulfonyl, C1–C20 alkylsulfinyl, and silyl.

In one aspect, at least one of the R9, R10, R10', R11, R11', R12, R12', R13, R13' and R14 substituent groups is substituted with at least one moiety selected from C1–C10 alkyl, C1–C10 alkoxy, and aryl which in turn may each be further substituted with at least one group selected from a halogen, a C1–C5 alkyl, C1–C5 alkoxy and phenyl.

In another aspect, at least one of the R9, R10, R10', R11, R11', R12, R12', R13, R13' and R14 substituent groups further includes at least one functional group. Functional groups suitable for use in these substituent groups include, for example, hydroxyl, thiol, alcohol, sulfonic acid, phosphine, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl and halogen.

In another aspect, R10, R10', R11, R11', R12, R12', R13 and R13' are each independently selected from hydrogen, methyl, aralkyl and aryl and R9 and R14 are each independently selected from substituted or unsubstituted C1–C10 alkyl, C1–C10 cycloalkyl, C2–C10 alkenyl, aralkyl and aryl.

In another aspect, R10, R10', R11, R11', R12, R12', R13 and R13' are each hydrogen and R9 and R14 substituents are each independently substituted or unsubstituted and are selected from phenyl, vinyl, methyl, isopropyl, tert-butyl, neopentyl and benzyl.

In another aspect, R10, R10', R11, R11', R12, R12', R13, and R13' are each hydrogen and R9 and R14 substituents are each independently substituted or unsubstituted and are selected from phenyl, vinyl, methyl, isopropyl, tert-butyl, neopentyl and benzyl; and wherein at least one of the substituents R9 and R14 is substituted with at least one moiety selected from C1–C5 alkyl, C1–C5 alkoxy, phenyl and a functional group. Functional groups suitable for use with this aspect of the present invention include, for example, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect, R9 and R14 are each independently substituted or unsubstituted aryl.

In another aspect, R9, R10, R10', R11, R11', R12, R12', R13, R13' and R14 are linked to form a substituted or unsubstituted, saturated or unsaturated ring structure.

In another aspect, R9, R10, R10', R11, R11', R12, R12', R13, R13' and R14 are linked to form a substituted or unsubstituted, saturated or unsaturated ring structure, wherein the ring structure contains substituents selected from hydrogen, methyl and substituted or unsubstituted aryl, aralkyl, C2–C10 alkenyl, C1–C10 cycloalkyl and C1–C10 alkyl.

In another aspect, R9, R10, R10', R11, R11', R12, R12', R13, R13' and R14 are linked to form a substituted or unsubstituted, saturated or unsaturated ring structure, wherein the ring structure contains substituents selected from alkoxy, aryloxy and functional groups selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect, R10, R10', R13 and R13' are each independently a hydrogen, a phenyl or together form a cycloalkyl or an aryl optionally substituted with at least one moiety selected from C1–C10 alkyl, C1–C10 alkoxy, aryl and a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and R9 and R14 are each independently C1–C10 alkyl or aryl optionally substituted with C1–C5 alkyl, C1–C5 alkoxy, aryl or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect, R10, R10', R14 and R14' are both hydrogen or phenyl, or together form a cycloalkyl group; if present, R11, R11', R12 and R12' are each hydrogen; and R9 and R14 are each selected from substituted or unsubstituted aryl.

In another aspect, R9 and R14 are independently of structure (E):

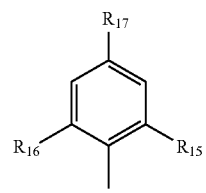

wherein R15, R16, and R17 are each independently hydrogen, C1–C10 alkyl, C1–C10 alkoxy, aryl or a functional group selected from hydroxyl, thiol, thioether, ketone, aldehyde, ester, ether, amine, imine, amide, nitro, carboxylic acid, disulfide, carbonate, isocyanate, carbodimide, carboalkoxy, carbamate and halogen.

In another aspect, R9 and R14 are independently of structure (E), wherein R15, R16, and R17 are each independently selected from hydrogen, methyl, ethyl, propyl, isopropyl, hydroxyl and halogen.

In another aspect, R9 and R14 are independently of structure (E), wherein R15, R16, and R17 are each methyl.

In another aspect, the connecting group, Z, may be substituted with one or more moieties selected from C1–C10 alkyl, C1–C10 alkoxy and aryl; which in turn may each be further substituted with one or more groups selected from a halogen, a C1–C5 alkyl, C1–C5 alkoxy and phenyl.

In another aspect, the connecting group, Z, may further include one or more functional groups. Functional groups suitable for use in connecting group, Z, include, for example, hydroxyl, thiol, alcohol, sulfonic acid, phosphine, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl and halogen.

Additional moieties suitable as bridging ligands include methylenes, alkylenes, halides, and pseudohalides. The methylenes (i.e., $CR_2$) and alkylenes (i.e., $(CR_2)_n$, n=1–24), may have R-groups which, independently, may be C1–C20 alkyl or branched alkyl, mono and multi-ring aryl. Further, any of the carbons of these methylenes and alkylenes may be further substituted with functional groups. Halides and pseudohalides may be and first ligand, second ligands, or bridging moieties. Suitable halides include, for example, fluoride, chloride, bromide, and iodide. Suitable pseudohalides include, for example, cyanide, isocyanide, alkoxides, thioalkoxides, amines, and phosphides. Hydride may further be a bridging moiety.

Hemilabile ligands contain at least two different types of donor sites, wherein at least one donor site is capable of acting as a "non-labile donor site", such as the donor sites of the first, second, and third ligands of the present invention, and at least one donor site is capable of acting as a "labile donor site", such as the donor sites of the first and second labile ligands of the present invention. Typically, a labile donor site is easily displaced from a coordination bond with a metal by, for example, the donor sites of labile ligands (e.g., solvent molecules) and by ethylenically unsaturated monomer. It, therefore, follows that a labile donor site of a hemi-labile ligand is easily displaced by strongly coordinating ligands, such as the first, second, and third ligands of the present invention. In contrast, a non-labile donor site is difficult to displace from coordination bond with a metal. Therefore, when a hemilabile ligand is attached to a metal pair of a cationic metal-pair complex or precursor complex of the present invention, the formalism for assigning subscripts to any cationic metal-pair complex formula or precursor complex formula is as follows: when a hemilabile ligand is bound to a single metal atom of a metal atom pair, any coordination bonds formed by any of the donor sites (labile or non-labile) of that hemilabile ligand will be treated as coordination bonds of first or second ligands; when a hemilabile ligand is bound to both metal atoms of a metal atom pair, any coordination bonds formed by any of the donor sites (labile or non-labile) of that hemilabile ligand will be treated as coordination bonds of a bridging moiety. Further description of hemilabile ligands may be found in: Braunstein, P.; Naud, F. Angew. Chem. Int. Ed. 2001, 40, 680; Slone, C. S.; Weinberger, D. A Mirkin, C. A. Prog. Inorg. Chem. 1999, 48, 233., and the hemilabile ligands of the present invention include those described therein.

One skilled in the art of organometallic chemistry will recognize that the hemilabile ligands of the present invention may be any hemilabile ligand. For illustrative purposes, a non-exhaustive list of hemi-labile phosphine ligands is described. Similar lists exist for other Group 14, 15, 16, and 17 atom containing ligands. By hemilabile phosphine ligand is meant a phosphine ligand containing an additional heteroatom substituent, (e.g., oxygen or sulfur), capable of weakly complexing a metal atom. Included in the hemilabile phosphine ligands of the present invention are hemilabile phosphine ligands represented by the formula $P(R^{24})_2Q$ wherein $R^{24}$ independently represents linear and branched $(C_1-C_{12})$ alkyl, cycloalkyl and $(C_6-C_{14})$ aryl and substituted aryl, and Q represents an organic moiety containing a heteroatom, selected from phosphorous, oxygen, and sulfur and combinations thereof. Examples of the Q substituent include but are not limited to—dibenzothiophene, ortho-alkoxyphenyl-, ortho-alkoxycarbonylphenyl-, wherein the alkoxy group is linear or branched $(C_1-C_5)$ alkoxy; $-(CH_2)_qS(=O)C_6H_5$, $-(CH_2)_qSC_6H_5$, $-(CH_2)_qP(=O)(C_6H_5)_2$, $-(CH_2)_qP(=S)(C_6H_5)_2$, wherein q is 2 or 3. Example of ligands excluded from this class of hemiligands are the strongly chelating ligands, e.g., the diphosphines such as diphenylphosphinoethane and diphenylphosphinopropane. Specific examples of suitable hemilabile phosphine ligands are illustrated below:

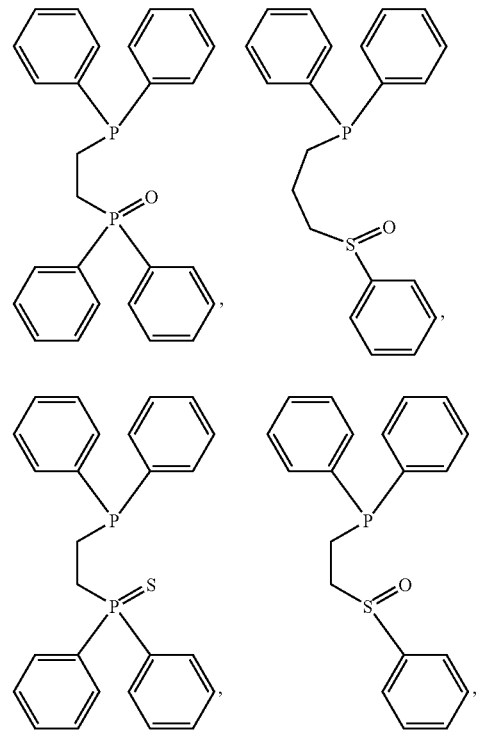

-continued

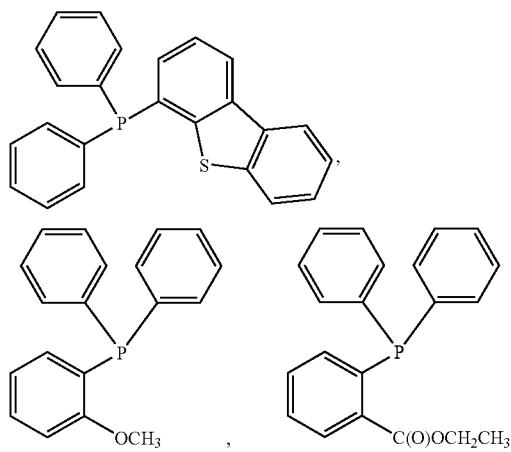

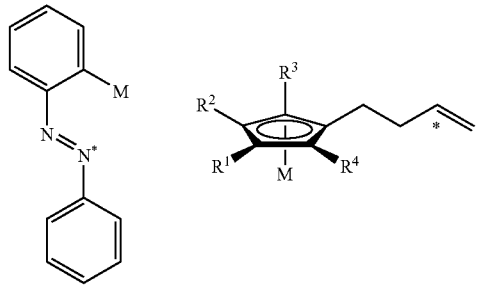

The following hemilabile ligands are shown coordinated to a metal atom, M, through a non-labile donor site. Labile donor sites, available for weak bonding to the same metal atom, or another metal atom are indicated by asterisk.

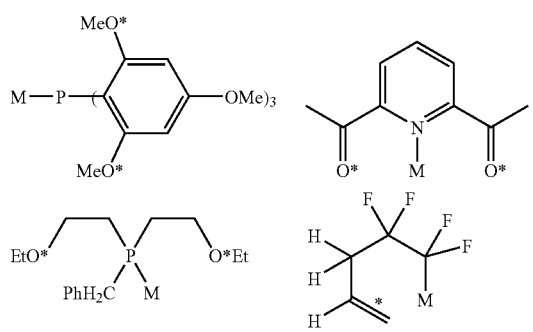

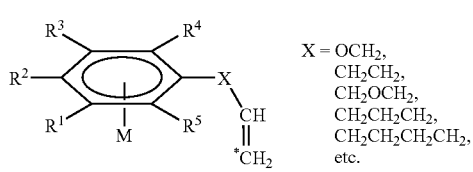

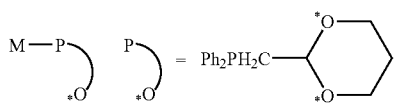

A non-exhaustive list of ligands further illustrating bridging moieties of the present invention, is found in Table I. Some of the bridging moieties of Table I are disclosed in Gavrilova, A. L.; Bosnich, B. *Chem. Rev.* 2004, 104, 349, wherein still further suitable bridging moieties are disclosed.

TABLE I

Examples of bridging moieties of the present invention.

| Bridging unit name | Bridging unit | Metal binding mode |
|---|---|---|
| Halide, Pseudohalide | $X^\ominus$ <br> X = F, Cl, Br, I, NCO, NCS, $N_3$, etc. | $M^1\text{-}X\text{-}M^2$ <br> X = F, Cl, Br, I, NCO, NCS, $N_3$, etc. |
| Methylene, (methylene)$_n$ | $[R_{k1}\text{-}\{C\}_n\text{-}R_{k2}]^\ominus$ <br> $\ominus$ n = 1, 2, 3, 4, ..., 24 <br> $CH_2$, k = 1, ..., n | $M^1\text{-}\{C\}_n(R_{k1})(R_{k2})\text{-}M^2$ <br> $CH_2$ n = 1, 2, 3, 4, ..., 24 <br> $M^1\text{-}M^2$, k = 1, ..., n |
| Carboxylate | R-C(O)($O^\ominus$) | syn, syn; syn, anti; anti, anti |

TABLE I-continued

Examples of bridging moieties of the present invention.

| Bridging unit name | Bridging unit | Metal binding mode |
|---|---|---|
| Formamidinate | | syn, syn |
| Pyrazolate | | |
| Triazolate | | |
| Oxadiazole | | |
| Triadiazole | | |
| Pyridazine and Phthalazine | | |
| 1,8-Naphthyridine | | |
| Phenolate, Alkoxide | | |

TABLE I-continued

Examples of bridging moieties of the present invention.

| Bridging unit name | Bridging unit | Metal binding mode |
|---|---|---|
| Thiophenolate, thioalkoxide | | |
| Disulfide | | |
| Phosphide | | |

An additional illustrative example of a bridging moiety is "NON":

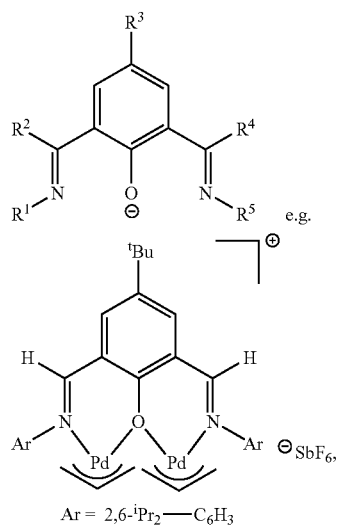

depicted here in a cationic metal-pair complex in which both $M^1$ and $M^2$ are palladium.

Any monodentate or multidentate labile ligand may be a first labile ligand of set $S^1$ or a second ligand of set $S^2$ of the present invention, provided that constraints (e.g., electronic, steric, and other spatial constraints) which exist for that labile ligand in any given cationic metal-pair complex, or precursor complex allow that monodentate or multidentate ligand to participate in at least one coordination bond with the corresponding metal atom ($M^1$ for labile ligand set $S^1$; and $M^2$ for labile ligand set $S^2$) of a metal-atom pair. Further, any multidentate labile ligand may simultaneously participate in at least one coordination bond of each metal atom in a metal atom pair. In such case, the labile ligand is acting as a bridging moiety, so the formalism for assigning subscripts to any cationic metal-pair complex formula or precursor complex formula is as follows: when a labile ligand is bound to both metal atoms of a metal atom pair, any coordination bonds formed by labile donor sites of that labile ligand will be treated as coordination bonds of a bridging moiety (ie., of set $L^3$).

A non-exhaustive list of the labile neutral electron donor ligands of the present invention includes solvents such as methylene chloride, $CHCl_3$, $ClCH_2CH_2Cl$, acrylonitrile, tetrahydrofuran, toluene, benzene, chlorobenzene, and polar monomers, as well as any other diluents typified by those found in the list of diluents, herein, which are able to donate electron density to a metal atom coordination site to form a coordination bond. Further, molecules such as, for example, dioxane, crown ethers, other polyethers, and cyclodextrins typify labile ligands capable of bridging between the metal atoms of a metal atom pair, and, where electronic, steric, and special constraints permit, between, or among metal atom pairs. One skilled in the art of organometallic chemisty will understand that a labile ligand may participate in a coordination bond with a one or both metal atoms of a metal atom pair. Alternatively, a labile ligand may be more loosely associated as part of a solvation sphere which may, in some cases, surround any of the cationic metal-pair complexes or precursor complexes of the present invention. According to common practice in the art, these more loosely associated molecules of the solvation sphere are not explicitly indicated in the cationic metal-pair complex formula or the precursor complex formula.

$R^1$ is an anionic hydrocarbyl containing radical which appears in the formulae for the precursor complex, for the first semi-(metal pair), and for the cationic metal-pair complex of the present invention. $R^2$ is an anionic hydrocarbyl containing radical which appears in the formulae for the second semi-(metal pair), for the cationic metal-pair complex and, optionally, for the precursor complex of the present invention. When both $R^1$ and $R^2$ are present in the same precursor complex or in the same cationic metal-pair complex, they may be identical or different entities. $R^1$ and $R^2$ may be, independently, selected from the following non-exhaustive lists of types of anionic hydrocarbyl containing radical and of specific examples of anionic hydrocarbyl containing radical.

First and second anionic hydrocarbyl containing radicals include, but are not limited to, hydrogen, linear and branched C1–C20 alkyl, C5–C10 cycloalkyl, linear and branched C2–C20 alkenyl, C6–C15 cycloalkenyl, allylic and methallylic ligands, crotyl ligands, or canonical forms thereof, C6–C30 aryl, C6–C30 heteroatom containing aryl, and C7–C30 aralkyl, each of the foregoing groups can be optionally substituted with hydrocarbyl containing and/or heteroatom substituents preferably selected from linear or branched C1–C5 alkyl, linear or branched C1–C5 haloalkyl, linear or branched C2–C5 alkenyl and haloalkenyl, halogen, sulfur, oxygen, nitrogen, phosphorus, and phenyl optionally substituted with linear or branched C1–C5 alkyl, linear or branched C1–C5 haloalkyl, and halogen. $R^1$ and $R^2$ also represent anionic containing ligands of the formula R"C(O)O, R"C(O)CHC(O)R", R"C(O)S, R"C(S)O, R"C(S)S, R"O, and R"$_2$N.

Additional representative examples of anionic ligands:

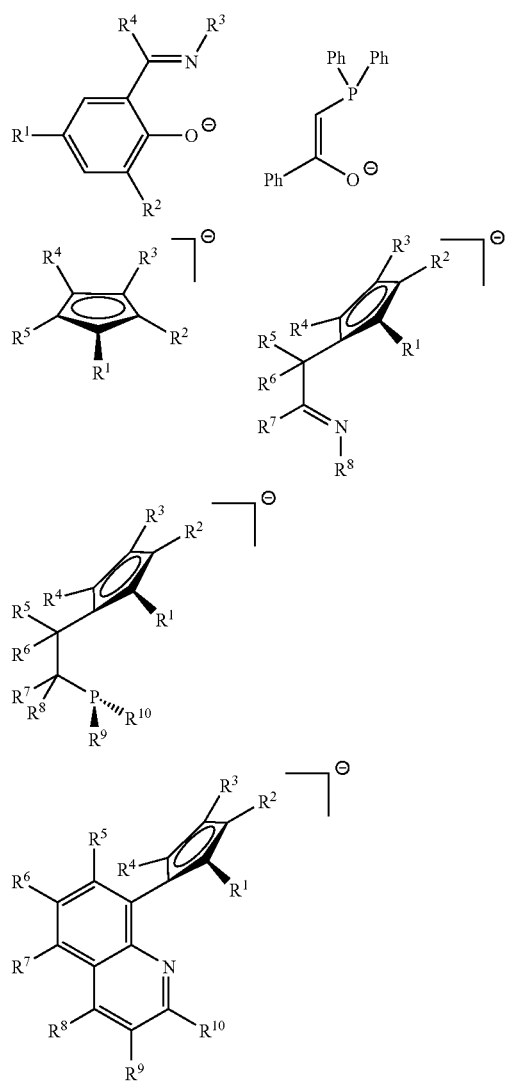
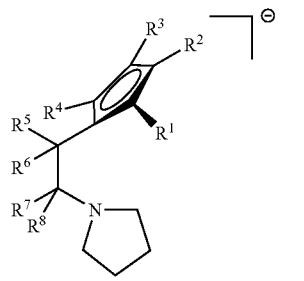

wherein the various R-groups may be: C1–C12 linear, branched, or cyclic and polycyclic alkyl; aryl or polycyclic aryl; or functional groups; and the alkyl and aryl groups may be further substituted with functional groups.

A "leaving group" ("Y") is capable of being removed from a precursor complex of the present invention by the action of an activator component. A leaving group (e.g., a halide or pseudohalide) may be bound to both metals or a single metal of a metal pair of a full-(metal pair) precursor complex, or bound to the single metal atom of a semi-(metal pair) precursor complex.

Additional examples of anionic hydrocarbyl containing ligands are disclosed in U.S. Pat. No. 6,455,650; R. G. Guy and B. L. Shaw, Advances in Inorganic Chemistry and Radiochemistry, Vol. 4, Academic Press Inc., New York, 1962; J. Birmingham, E. de Boer, M. L. H. Green, R. B. King, R. Köster, P. L. I. Nagy, G. N. Schrauzer, Advances in Organometallic Chemistry, Vol. 2, Academic Press Inc., New York, 1964; W. T. Dent, R. Long and A. J. Wilkinson, J. Chem. Soc., (1964) 1585; and H. C. Volger, Rec. Trav. Chim. Pay Bas, 88 (1969) 225.

A "WCA" is a "weakly coordinating anion". The weakly coordinating anion is an anion that is only weakly coordinated to the cationic metal-pair complex. The WCA is sufficiently labile to be displaced by a neutral Lewis base, solvent or monomer. More specifically, the WCA functions as a stabilizing anion to the cationic metal-pair complex and does not transfer to the cationic metal-pair complex to form a neutral product. The WCA is relatively inert in that it is non-oxidative, non-reducing, and non-nucleophilic.

The weakly coordinating anion can be selected, for example, from borates and aluminates, boratobenzene anions, carborane halocarborane anions, antimony halide anions (e.g., $SbF_6$), phosphorus halide anions (e.g., $PF_6$), and boron halide anions (e.g., $BF_4$). The borate and aluminate weakly coordinating anions are represented by the structures II and III below:

$$[Q(R^4)(R^5)(R^6)(R^7)]\text{structure} \qquad \text{II}$$

$$[Q(O\ R^8)(O\ R^9)(O\ R^{10})(O\ R^{11})] \qquad \text{III}$$

wherein, in structure II, Q is boron or aluminum and $R^4$, $R^1$, $R^6$, and $R^7$ independently represent fluorine, linear and branched C1–C10 alkyl, linear and branched C1–C10 alkoxy, linear and branched C3–C5 haloalkenyl, linear and branched C3–C12 trialkylsiloxy, C18–C36 triarylsiloxy, substituted and unsubstituted C6–C30 aryl, and substituted and unsubstituted C6–C30 aryloxy groups wherein $R^4$ to $R^7$ can not all simultaneously represent alkoxy or aryloxy groups. When substituted the aryl groups can be monosubstituted or multisubstituted, wherein the substituents are independently selected from linear and branched C1–C5 alkyl, linear and branched C1–C5 haloalkyl, linear and branched C1–C5 alkoxy, linear and branched C1–C5 haloalkoxy, linear and branched C1–C12 trialkylsilyl, C6–C18 triarylsilyl, and halogen selected from chlorine, bromine, and fluorine, preferably fluorine. Representative borate anions under Structure II include but are not limited to tetrakis(pentafluorophenyl)borate, tetrakis(3,5-bis(trifluoromethyl)phenyl)borate, tetrakis(2-fluorophenyl) borate, tetrakis(3-fluorophenyl)borate, tetrakis(4-fluorophenyl)borate, tetrakis(3,5-difluorophenyl)borate, tetrakis(2,3,4,5-tetrafluorophenyl) borate, tetrakis(3,4,5,6-tetrafluorophenyl) borate, tetrakis(3,4,5-trifluorophenyl)borate, methyltris(perfluorophenyl)borate, ethyltris(perfluorophenyl)borate, phenyltris(perfluorophenyl)borate, tetrakis(1,2,2-trifluoroethylenyl)borate, tetrakis(4-tri-1-propylsilyltetrafluorophenyl)borate, tetrakis(4-dimethyl-tert-butylsilyltetrafluorophenyl)borate, (triphenylsiloxy) tris(pentafluorophenyl)borate, (octyloxy)tris(pentafluorophenyl)borate, tetrakis [3,5-bis[1-methoxy-2,2,2-trifluoro-1-(trifluoromethyl)ethyl] phenyl]borate, tetrakis[3-[1-methoxy-2,2,2-trifluoro-1-(trifluoromethyl) ethyl]-5-(trifluoromethyl)phenyl]borate, and tetrakis[3-[2,2,2-trifluoro-1-(2,2,2-trifluoroethoxy)-1-(trifluoromethyl)ethyl]-5-(trifluoromethyl) phenyl]borate.

Representative aluminate anions under Structure II include but are not limited to tetrakis(pentafluorophenyl) aluminate, tris(perfluorobiphenyl) fluoroaluminate, (octyloxy)tris(pentafluorophenyl)aluminate, tetrakis(3,5-bis(trifluoromethyl)phenyl)aluminate, and methyltris (pentafluorophenyl) aluminate.

In Structure III Q is boron or aluminum, $R^8$, $R^9$, R10, and $R^{11}$ independently represent linear and branched C1–C10 alkyl, linear and branched C1–C10 haloalkyl, C2–C10 haloalkenyl, substituted and unsubstituted C6–C30 aryl, and substituted and unsubstituted C7–C30 aralkyl groups, subject to the proviso that at least three of $R^8$ to $R^{11}$ must contain a halogen containing substituent. When substituted the aryl and aralkyl groups can be monosubstituted or multisubstituted, wherein the substituents are independently selected from linear and branched C1–C5 alkyl, linear and branched C1–C5 haloalkyl, linear and branched C1–C5 alkoxy, linear and branched C1–C10 haloalkoxy, and halogen selected from chlorine, bromine, and fluorine, preferably fluorine. The groups $OR^8$ and $OR^9$ can be taken together to form a chelating substituent represented by —O—R $R^{12}$ —O—, wherein the oxygen atoms are bonded to Q and $R^{12}$ is a divalent radical selected from substituted and unsubstituted C6–C30 aryl and substituted and unsubstituted C7–C30 aralkyl. Preferably, the oxygen atoms are bonded, either directly or through an alkyl group, to the aromatic ring in the ortho or meta position. When substituted the aryl and aralkyl groups can be monosubstituted or multisubstituted, wherein the substituents are independently selected from linear and branched C1–C5 alkyl, linear and branched C1–C5 haloalkyl, linear and branched C1–C5 alkoxy, linear and branched C1–C10 haloalkoxy, and halogen selected from chlorine, bromine, and fluorine, preferably fluorine.

Representative borate and aluminate anions under Structure III include but are not limited to $[B(OC(CF_3)_3)_4]^-$, $[B(OC(CF_3)_2(CH_3))_4]^-$, $[B(OC(CF_3)_2H)_4]^-$, $[B(OC(CF_3)(CH_3)H)_4]^-$, $[Al(OC(CF_3)_2Ph)_4]^-$, $[B(OCH_2(CF_3)_4]^-$, $[Al(OC(CF_3)_2C_6H_4CH_3)_4]^-$, $[Al(OC(CF_3)_3)_4]^-$, $[Al(OC(CF_3)(CH_3)H)_4]^-$, $[Al(OC(CF_3)_2H)_4]^-$, $[Al(OC(CF_3)_2C_6H_4$-4-i-$Pr)_4]^-$, $[Al(OC(CF_3)_2C_6H_4$-4-t-butyl)_4]^-, $[Al(OC(CF_3)_2C_6H_4$-4-SiMe_3)_4]^-$, $[Al(OC(CF_3)_2C_6H_4$-4-Si-i-$Pr_3)_4]^-$, $[Al(OC(CF_3)_2C_6H_2$-2,6-$(CF_3)_2$-4-Si-i-$Pr_3)_4]^-$, $[Al(OC(CF_3)_2C_6H_3$-3,5-$(CF_3)_2)_4]^-$, $[Al(OC(CF_3)_2C_6H_2$2,4,6-$(CF_3)_3)_4]^-$, and $[Al(OC(CF_3)_2C_6F_5)_4]^-$.

Representative boratobenzene anions include but are not limited to [1,4-dihydro-4-methyl-1-(pentafluorophenyl)]-2-borate, 4-(1,1-dimethyl)-1,2-dihydro-1-(pentafluorophenyl)-2-borate, 1-fluoro-1,2-dihydro-4-(pentafluorophenyl)-2-borate, and 1-[3,5-bis(trifluoromethyl)phenyl]-1,2-dihydro-4-(pentafluorophenyl)-2-borate.

The carborane and halocarborane anions useful as the weakly coordinating anion include but are not limited to $CB_{11}(CH_3)_{12}^-$, $CB_{11}H_{12}^-$, $1$-$C_2H_5CB_{11}H_{11}$, $1$-$Ph_3SiCB_{11}H_{11}^-$, $1$-$CF_3CB_{11}H_{11}^-$, $12$-$BrCB_{11}H_{10}^-$, $12$-$ClCB_{11}H_{11}^-$, $7,12$-$Cl_2CB_{11}H_{10}^-$, $1$-H—$CB_{11}F_{11}^-$, $1$-$CH_3$–$CB_{11}F_{11}^-$, $1$-$CF_3$—$CB_{11}F_{11}^-$, $12$-$CH$—$CB_{11}H_{11}^-$, $1$-$CH_3$—$CB_{11}F_{11}^-$, $1$-$CF_3$—$CB_{11}F_{11}^-$, $12$-$CB_{11}H_{11}F^-$, $7,12$-$CB_{11}H_{11}F_{12}^-$, $7,9,12$-$CB_{11}H_{11}F_3^-$, $CB_{11}H_6Br_6^-$; $6$-$CB_9H_9F^-$, $6,8$-$CB_9H_8F_2^-$, $6,7,8$-$CB_9H_7F_3^-$, $6,7,8,9$-$CB_9H_6F_4^-$, $2,6,7,8,9$,-$CB_9H_5F_5^-$, $CB_9H_5Br_5^-$, $CB_{11}H_6Cl_6^-$, $CB_{11}H_6F_6^-$, $CB_{11}H_6F_6^-$, $CB_{11}H_6F_6^-$, $CB_{11}H_6I_6^-$, $CB_{11}H_6Br_6^-$, $6,7,9,10,11,12$-$CB_{11}H_6F_6^-$, $2,6,7,8,9,10$-$CB_9H_5F_5^-$, $1$-H—$CB_9F_9^-$, $12$-$CB_{11}H_{11}(C_6H_5)^-$, $1$-$C_6F_5$—$CB_{11}H_5Br_6^-$, $CB_{11}Me_{12}^-$, $CB_{11}(CF_3)_{12}^-$, $Co(B_9C_2H_{11})_2^-$, $CB_{11}(CH_3)_{12}^-$, $CB_{11}(C_4H_{12})_{12}^-$, $CB_{11}(C_6H_{13})_{12}^-$, $Co(C_2B_9H_{11})_2^-$, $Co(Br_3C_2B_9H_8)_2^-$ and dodecahydro-1-carbadodecaborate. The weakly coordinating anion of the present invention further includes any of those disclosed in U.S. Pat. No. 6,455,650.

Illustrative, but non-limiting examples of the "activator component" of the present invention are disclosed in publications of Chen and Marks, such as Chem. Rev., 100, 1391–1434, 2000, Coates, such as Chem. Rev., 100, 1223–1252, 2000, Resconi et al, such as Chem. Rev., 100, 1253–1346, 2000, Fink et al, such as Chem. Rev., 100, 1377–1390, 2000 Alt and Koeppl, such as Chem. Rev., 100, 1205–1222, 2000 and Hlatky, Chem. Rev., 100, 1347–1376, 2000, the contents of which are usefully employed in accordance with the present invention. Activator components useful in the method of preparing the cationic metal-pair complex of the present invention, for example, include: aluminum alkyls such as $Al(C_2H_5)_3$, $Al(CH_2CH(CH_3)_2)_3$, $Al(C_3H_7)_3$, $Al((CH_2)_3CH_3)_3$, $Al((CH_2)_5CH_3)_3$, $Al(C_6F_5)_3$, $Al(C_2H_5)_2Cl$, $Al_2(C_2H_5)_3Cl_2$, $AlCl_3$; aluminoxanes such as methylaluminoxane (MAO), modified methyl aluminoxane (MMAO), isobutylaluminoxane, butylaluminoxane, heptylaluminoxane and methylbutylaluminoxane; and combinations thereof. Both stoichiometric and non-stoichiometric quantities of activator components are usefully employed in the present invention. Chemically and structurally useful aluminum compounds as well as other activator components of Group 13 elements would be apparent to those skilled in the art based on their respective chemical structures and activities in preparing cationic metal-pair complexes.

The activator component further comprises hydroxyaluminoxanes. Hydroxyaluminoxanes, and methods of preparing them, are disclosed in U.S. Pat. No. 6,160,145. The hydroxyaluminoxane has a hydroxyl group bonded to at least one of its aluminum atoms.

The alkyl aluminum compound used in forming the hydroxyaluminoxane reactant can be any suitable alkyl aluminum compound other than trimethylaluminum. Thus at least one alkyl group has two or more carbon atoms. Preferably each alkyl group in the alkyl aluminum compound has at least two carbon atoms. More preferably each alkyl group has in the range of 2 to about 24, and still more preferably in the range of 2 to about 16 carbon atoms. Most preferred are alkyl groups that have in the range of 2 to about 9 carbon atoms each. The alkyl groups can be cyclic (e.g., cycloalkyl, alkyl-substituted cycloalkyl, or cycloalkyl-substituted alkyl groups) or acyclic, linear or branched chain alkyl groups. Preferably the alkyl aluminum compound contains at least one, desirably at least two, and most preferably three branched chained alkyl groups in the molecule. Most preferably each alkyl group of the aluminum alkyl is a primary alkyl group, i.e., the alpha-carbon atom of each alkyl group carries two hydrogen atoms.

Suitable aluminum alkyl compounds which may be used to form the hydroxyaluminoxane reactant include dialkylaluminum hydrides and aluminum trialkyls. Examples of the dialkylaluminum hydrides include diethylaluminum hydride, dipropylaluminum hydride, diisobutylaluminum hydride, di(2,4,4-trimethylpentyl)aluminum hydride, di(2-ethylhexyl)aluminum hydride, di(2-butyloctyl)aluminum hydride, di(2,4,4,6,6-pentamethylheptyl)aluminum hydride, di(2-hexyldecyl)aluminum hydride, dicyclopropylcarbinylaluminum hydride, dicyclohexylaluminum hydride, dicyclopentylcarbinylaluminum hydride, and analogous dialkylaluminum hydrides. Examples of trialkylaluminum compounds which may be used to form the hydroxyaluminoxane include triethylaluminum, tripropylaluminum, tributylaluminum, tripentylaluminum, trihexylaluminum, triheptylaluminum, trioctylaluminum, and their higher straight chain homologs; triisobutylaluminum, tris(2,4,4-trimethylpentyl)aluminum, tri-2-ethylhexylaluminum, tris(2,4,4,6,6-pentamethylheptyl)aluminum, tris(2-butyloctyl)aluminum, tris(2-hexyldecyl)aluminum, tris(2-heptylundecyl)aluminum, and their higher branched chain homologs; tri(cyclohexylcarbinyl)aluminum, tri(2-cyclohexylethyl)aluminum and analogous cycloaliphatic aluminum trialkyls; and tri (pentafluoro)aluminum. Triisobutylaluminum has proven to be an especially desirable alkyl aluminum compound for producing a hydroxyaluminoxane. Hydroxyisobutylaluminoxane (HOIBAO) is a preferred hydroxyaluminoxane. The hydroxyisobutylaluminoxane is essentially devoid of unreacted triisobutylaluminum.

Useful activator components further include aluminoxane salt compositions (aluminoxinates) as disclosed in U.S. Pat. No. 5,922,631. Useful activator components still further include any of the liquid clathrate aluminoxanes disclosed in U.S. Pat. No. 5,670,682.

Activator components useful in the present invention further include organic borane compounds, inorganic borane compounds, and borate anions. Preferred examples of boron containing activator components employed in the method of preparing the cationic metal-pair complex of the present invention are trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane, tris(3,4,5-trifluorophenyl)borane, dimethylanilinium (pentafluorophenyl) borate, sodium[B{3,5-$(CF_3)_2C_6F_3$}$_4$], [H(OEt$_2$)$_2$[B{3,5-$(CF_3)_2C_6F_3$}$_4$]. Both stoichiometric and non-stoichiometric quantities of activators are usefully employed using triaryl carbenium tetraarylborates, N,N-dialkylanilinium salts such as N,N-dimethylanilinium tetra(pentafluorophenyl)borate, N,N-diethylanilinium tetra(phenyl)borate, N,N-2,4,6-pentamethylanilinium tetraphenylborate and chemically related Group 13 compounds; dialkyl ammonium salts such as di(i-propyl)ammonium tetra(pentafluorophenyl)borate, dicyclohexylammonium tetra(phenyl)boron and chemically related Group 13 compounds; triaryl phosphonium salts such as triphenylphosphonium tetraphenylborate, tri(methylphenyl)phosphonium tetra(phenyl)borate, tri(dimethylphenyl)phosphonium tetra(phenyl)borate and chemically related Group 13 compounds. Any complex anions or compounds forming such anions that exhibit an ability to abstract and activate the metal compounds would be within the scope of the "activator component" of the present invention. Chemically and structurally useful boron compounds would be apparent to those skilled in the art based on their respective chemical structures and activities in olefin polymerizations.

In the method of the present invention, the activator component is present in an amount of: at least 0.1 molar equivalent, at least 0.3 molar equivalent, at least 0.7 molar equivalent, or at least 1.0 molar equivalent, based on leaving group Y; and no more than 5,000 molar equivalent, no more than 500 molar equivalent, no more than 5 molar equivalent, or no more than 2 molar equivalents, based on leaving group Y.

The non-polar olefinic monomers of the present invention include, for example, unbranched aliphatic olefins having from 2 to 12 carbon atoms, branched aliphatic olefins having from 4 to 12 carbon atoms, unbranched and branched aliphatic α-olefins having from 2 to 12 carbon atoms, conjugated olefins having 4 to 12 carbon atoms, aromatic olefins having from 8 to 20 carbons, unbranched and branched cycloolefins having 3 to 12 carbon atoms, unbranched and branched acetylenes having 2 to 12 carbon atoms, and combinations thereof. A non-exhaustive list of examples of non-polar olefinic monomers of the present invention includes ethylene, propene, 1-butene, 1-hexene, butadiene, 1,5-hexadiene, isoprene, styrene, alpha-methylstyrene, cyclopentene, cyclohexene, cyclohexadiene, norbornene, norbornadiene, cyclooctadiene, divinylbenzene, trivinylbenzene, acetylene, diacetylene, alkynylbenzene, dialkynylbenzene, ethylene/1-butene, ethylene/isopropene, ethylene/1-hexene, ethylene/1-octene, ethylene/propene, ethylene/cyclopentene, ethylene/cyclohexene, ethylene/butadiene, ethylene/1,5-hexadiene, ethylene/styrene, ethylene/acetylene, propene/1-butene, propene/styrene, propene/butadiene, propylene/1-hexene, propene/acetylene, ethylene/propene/1-butene, ethylene/propene/1-hexene, ethylene/propene/1-octene, and various combinations thereof.

Polar olefinic monomers of the present invention include ethylenically unsaturated monomers having from 2 to 60 carbon atoms and at least one atom such as O, N, B, Al, S, P, Si, F, Cl, Br, and combinations thereof. These polar olefinic monomers include, for example: $C_1$–$C_{22}$ linear or branched chain alkyl (meth)acrylates, bornyl (meth)acrylate, and isobornyl (meth)acrylate; hydroxyethyl (meth)acrylate, hydroxypropyl (meth)acrylate; (meth)acrylamide or substituted (meth)acrylamides; epoxy containing (meth)acrylates such as glycidyl (meth)acrylate; styrene or substituted styrenes; butadiene; vinyl acetate or other vinyl ester; vinyl chloride; vinylidene chloride; vinylidene fluoride; N-butylaminoethyl (meth)acrylate, N,N-di(methyl)aminoethyl (meth)acrylate; monomers containing α,β-unsaturated carbonyl functional groups such as fumarate, maleate, cinnamate and crotonate; and (meth)acrylonitrile. Acid-functional methacrylic monomers include, for example, (meth) acrylic acid, itaconic acid, crotonic acid, phosphoethyl (meth)acrylate, sulfoethyl (meth)acrylate, 2-acrylamido-2-methyl-1-propanesulfonic acid, fumaric acid, maleic anhydride, monomethyl maleate, and maleic acid.

Polar olefinic monomers of the present invention further include: acrylic acid 5-oxo-tetrahydro-furan-3-yl ester, acrylic acid 1,1,2-trimethyl-propyl ester, acrylic acid 2-ethyl-1,3,3-trimethyl-bicyclo[2.2.1]hept-2-yl ester, acrylic acid 2-ethyl-adamantan-2-yl ester, acrylic acid 2-methyl-adamantan-2-yl ester, acrylic acid 4-hydroxy-adamantan-1-yl ester, acrylic acid 3-hydroxy-adamantan-1-yl ester, acrylic acid 5-hydroxy-2-methyl-adamantan-2-yl ester, 5H-Furan-2-one, 3-Methylene-dihydro-furan-2-one, acrylic acid 1,7,7-trimethyl-bicyclo[2.2.1]hept-2-yl ester, acrylic acid 1-methyl-cyclopentyl ester, acrylic acid 5-oxo-4-oxa-tricyclo[4.2.1.0 3,7]non-2-yl ester, acrylic acid 1,2,3,3-tetramethyl-bicyclo[2.2.1]hept-2-yl ester, acrylic acid tert-butyl ester, acrylic acid 1-ethyl-cyclopentyl ester, acrylic acid 3-oxo-4-oxa-tricyclo[5.2.1.0 2,6]dec-8-yl ester, and acrylic acid 1-(2-oxo-tetrahydro-furan-3-yl)-ethyl ester.

Suitable fluorinated (meth)acrylic monomers useful in the present invention include, but are not limited to: fluoroalkyl (meth)acrylate; fluoroalkylsulfoamidoethyl (meth)acrylate; fluoroalkylamidoethyl (meth)acrylate; fluoroalkyl (meth)acrylamide; fluoroalkylpropyl (meth)acrylate; fluoroalkylethyl poly(alkyleneoxide) (meth)acrylate; fluoroalkylsulfoethyl (meth)acrylate; fluoroalkylethyl vinyl ether; fluoroalkylethyl poly(ethyleneoxide) vinyl ether; pentafluoro styrene; fluoroalkyl styrene; vinylidene fluoride; fluorinated α-olefins; perfluorobutadiene; 1-fluoroalkylperfluorobutadiene; ωH-perfluoroalkanediol di(meth)acrylate; and β-substituted fluoroalkyl (meth)acrylate. The fluoroalkyl groups used as substituents have from 1 to 20 carbon atoms and the fluoroalkyl groups may be mono-, di, tri, or tetra-fluorinated, or contain any number of fluoro-atoms, up to and including perfluorinated compositions.

Silicon containing polar olefinic monomers useful in the present invention include, for example, trimethoxysilylethyl (meth)acrylate and trimethoxysilylpropyl (meth)acrylate.

The terms "cyclic olefin,", "polycyclic", "polycyclicolefin," and "norbornene-type" monomer as used herein are interchangeable and mean that the monomer contains at least one norbornene moiety as follows:

wherein W''' is selected from the group including, but by no means limited to, an oxygen, a nitrogen with a hydrogen attached thereto, a nitrogen with a linear $C_1$ to $C_{10}$ alkyl grouping attached thereto, a nitrogen with a branched $C_1$ to $C_{10}$ alkyl grouping attached thereto, a sulfur and a methylene group of having the formula —(CH$_2$)n'- wherein n' is an integer from 1 to 5.

Polycyclic monomers of the present invention include both polycyclic monomers that are non-polar monomers and polycyclic monomer that are polar monomer.

Polycyclic monomers suitable for use with the present invention include bicyclic monomers, for example, bicyclo[2.2.1]hept-2-ene also referred to as norbornene.

The term "norbornene-type monomer" as used herein and in the appended claims is meant to encompass norbornene, substituted norbornene, as well as any substituted and unsubstituted higher cyclic derivatives thereof, provided that the subject monomer contains at least one norbornene-type moiety or substituted norbornene-type moiety.

Norbornene-type monomers suitable for use with the present invention include substituted norbornene-type monomers and higher cyclic derivatives thereof that contain a pendant hydrocarbon group or a pendant functional substituent containing an oxygen atom.

Norbornene-type monomers suitable for use with the present invention may include norbornene-type or polycycloolefin monomers are represented by the structure below:

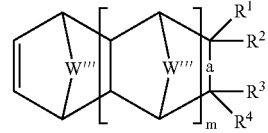

(A)

wherein each W''' is independently defined as above; "a" is a single or a double bond; $R^1$, $R^2$, $R^3$, and $R^4$ each independently represent a hydrogen, a hydrocarbyl or a functional substituent; m is an integer from 0 to 5, with the proviso that when "a" is a double bond, both (i) one of $R^1$ and $R^2$ is not present and (ii) one of $R^3$ and $R^4$ is not present.

The term "hydrocarbon groups" as used herein and in the appended claims encompasses hydrogen, hydrocarbon groups, halohydrocarbon groups, perhalohydrocarbon groups and perhalocarbyl groups. In one embodiment, $R^1$, $R^2$, $R^3$ and/or $R^4$, may independently represent hydrogen, linear or branched $C_1$–$C_{10}$ alkyl, linear or branched $C_2$–$C_{10}$ alkenyl, linear or branched $C_2$–$C_{10}$ alkynyl, $C_4$–$C_{12}$ cycloalkyl, $C_4$–$C_{12}$ cycloalkenyl, $C_6$–$C_{12}$ aryl, and $C_7$–$C_{24}$ aralkyl. In one embodiment, $R^1$ and $R^2$ or $R^3$ and $R^4$ may collectively represent a $C_1$–$C_{10}$ alkylidenyl group. Representative alkyl groups include, but are by no means limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are by no means limited to, vinyl, allyl, butenyl and cyclohexenyl. Representative alkynyl groups, include but are by no means limited to, ethynyl, 1-propynyl, 2-propynyl, 1-butynyl and 2-butynyl. Representative cycloalkyl groups include, but are by no means limited to, cyclopentyl, cyclohexyl and cyclooctyl substituents. Representative aryl groups include, but are by no means limited to, phenyl, naphthyl and anthracenyl. Representative aralkyl groups include, but are by no means limited to, benzyl and phenethyl. Representative alkylidenyl groups include, but are by no means limited to, methylidenyl and ethylidenyl groups.

In one embodiment, the perhalohydrocarbon groups may include perhalogenated phenyl and alkyl groups. The halogenated alkyl groups useful in the invention are partially or fully halogenated and are linear or branched, and have the formula $C_zW''_{2z+1}$ wherein W'' is independently selected from halogen and hydrogen and z is an integer of 1 to 20. In another embodiment, each W'' is independently selected from hydrogen, chlorine, fluorine and bromine. In another embodiment, each W'' is independently selected from hydrogen and fluorine.

In one embodiment, the perfluorinated substituents include perfluorophenyl, perfluoromethyl, perfluoroethyl, perfluoropropyl, perfluorobutyl and perfluorohexyl. In addition to the halogen substituents, the cycloalkyl, aryl, and aralkyl groups of the present invention may be further substituted with linear or branched $C_1$–$C_5$alkyl and haloalkyl groups, aryl groups and cycloalkyl groups.

When the pendant group(s) is(are) a functional substituent, $R^1$, $R^2$, $R^3$ may $R^4$ independently represent a radical selected from $(CH_2)_n$—CH(CF$_3$)$_2$—O—Si(Me)$_3$, —(CH$_2$)$_n$—CH(CF$_3$)$_2$—O—CH$_2$—O—CH$_3$, —(CH$_2$)$_n$—CH(CF$_3$)$_2$—O—C(O)—C(CH$_3$)$_3$, —(CH$_2$)$_n$—C(CF$_3$)$_2$—OH, —(CH$_2$)$_n$C(O)NH$_2$, —(CH$_2$)$_n$C(O)Cl, —(CH$_2$)$_n$C(O)OR$^5$, —(CH$_2$)$_n$—OR$^5$, —(CH$_2$)$_n$—OC(O)R$^5$, —(CH$_2$)$_n$—C(O) R$^5$, —(CH$_2$)$_n$—OC(O)OR$^5$, —(CH$_2$)$_n$Si(R$^5$)$_3$, —(CH$_2$)$_n$Si(OR$^5$)$_3$, —(CH$_2$)$_n$—O—Si(R$^5$)$_3$ and —(CH$_2$)$_n$C(O)OR$^6$ wherein n independently represents an integer from 0 to 10 and $R^5$ independently represents hydrogen, linear or branched $C_1$–$C_{20}$ alkyl, linear or branched $C_1$–$C_{20}$ halogenated or perhalogenated alkyl, linear or branched $C_2$–$C_{10}$ alkenyl, linear or branched $C_2$–$C_{10}$ alkynyl, $C_5$–$C_{12}$ cycloalkyl, $C_6$–$C_{14}$ aryl, $C_6$–$C_{14}$ halogenated or perhalogenated aryl, and $C_7$–$C_{24}$ aralkyl. Representative hydrocarbon groups set forth under the definition of $R^5$ are the same as those identified above under the definition of $R^1$ to $R^4$. As set forth above under $R^1$ to $R^4$ the hydrocarbon groups defined under $R^5$ may be halogenated and perhalogenated. For example, when $R^5$ is $C_1$–$C_{20}$ halogenated or perhalogenated alkyl, $R^5$ may be represented by the formula $C_zW''_{2z+1}$, wherein z and W'' are defined as above and at least one W'' on the alkyl group is a halogen. It is to be recognized that when the alkyl group is perhalogenated, all W'' substituents are halogenated. Examples of perhalogenated alkyl groups include, but are by no means limited to, trifluoromethyl, trichloromethyl, —$C_7F_{15}$, and —$C_{11}F_{23}$. Examples of perhalogenated aryl groups include, but are by no means limited to, pentachlorophenyl and pentafluorophenyl. The $R^6$ radical represents an acid labile moiety selected from —$C(CH_3)_3$, —$Si(CH_3)_3$, —$CH(R^7)OCH_2CH_3$, —$CH(R^7)OC(CH_3)_3$ or the following cyclic groups:

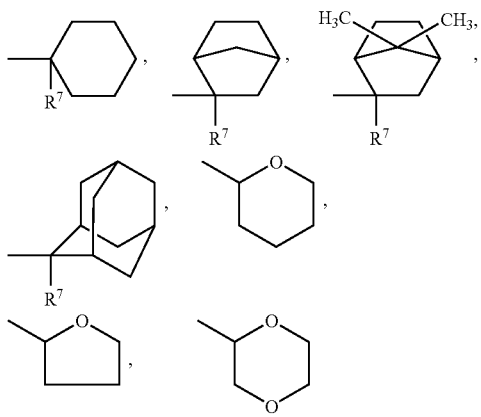

wherein $R^7$ represents hydrogen or a linear or branched ($C_1$–$C_5$) alkyl group. The alkyl groups may include methyl, ethyl, propyl, i-propyl, butyl, i-butyl, t-butyl, pentyl, t-pentyl and neopentyl. In the above structures, the single bond line projecting from the cyclic groups indicates the position where the cyclic protecting group is bonded to the acid substituent. Examples of $R^6$ radicals include 1-methyl-1-cyclohexyl, isobornyl, 2-methyl-2-isobornyl, 2-methyl-2-adamantyl, tetrahydrofuranyl, tetrahydropyranoyl, 3-oxocyclohexanonyl, mevalonic lactonyl, 1-ethoxyethyl and 1-t-butoxy ethyl.

The $R^6$ radical can also represent dicyclopropylmethyl (Dcpm), and dimethylcyclopropylmethyl (Dmcp) groups which are represented by the following structures:

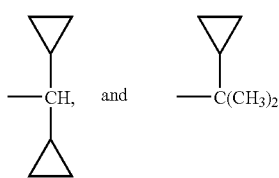

In the structure (B) above, $R^1$ and $R^4$ together with the two ring carbon atoms to which they are attached may represent a substituted or unsubstituted cycloaliphatic group containing 4 to 30 ring carbon atoms, a substituted or unsubstituted aryl group containing 6 to 18 ring carbon atoms, or a combination thereof. The cycloaliphatic group can be monocyclic or polycyclic. When unsaturated, the cyclic group may contain monounsaturation or multiunsaturation. In one embodiment, the unsaturated cyclic group may be a monounsaturated cyclic group. When substituted, the rings may contain monosubstitution or multisubstitution, wherein the substituents may independently be selected from hydrogen, linear or branched $C_1$–$C_5$ alkyl, linear or branched $C_1$–$C_5$ haloalkyl, linear or branched $C_1$–$C_5$ alkoxy, halogen and combinations thereof. $R^1$ and $R^4$ may be taken together to form the divalent bridging group, —C(O)—Q—(O)C—, which when taken together with the two ring carbon atoms to which they are attached form a pentacyclic ring, wherein Q represents an oxygen atom or the group N($R^8$), and $R^8$ may be selected from hydrogen, halogen, linear or branched $C_1$–$C_{10}$ alkyl, and $C_6$–$C_{18}$ aryl. A representative structure is shown in below as Structure (C):

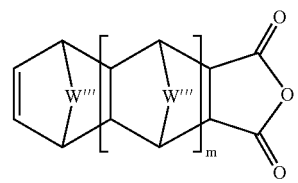

wherein each W''' is independently defined as above and m is an integer from 0 to 5.

Deuterium enriched norbornene-type monomers wherein at least one of the hydrogen atoms on the norbornene-type moiety and/or one at least one of the hydrogen atoms on a pendant hydrocarbon group described under $R^1$ to $R^4$ have been replaced by a deuterium atom are contemplated within the scope of the present invention. In one embodiment, at least 40 percent of the hydrogen atoms on the norbornene-type moiety and/or the hydrocarbon group are replaced by deuterium. In another embodiment, at least about 50 percent of the hydrogen atoms on the norbornene-type moiety and/or the hydrocarbon group are replaced by deuterium. In yet another embodiment, at least about 60 percent of the hydrogen atoms on the norbornene-type moiety and/or the hydrocarbon group are replaced by deuterium. In one embodiment, the deuterated monomers are represented by Structure (D) below:

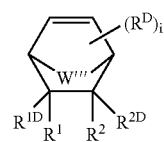

wherein W''' is defined as above, $R^D$ is deuterium, "i" is an integer from 0 to 6, $R^1$ and $R^2$ independently represent a hydrocarbyl or functional substituent as defined above and $R^{1D}$ and $R^{2D}$ may or may not be present and independently represent a deuterium atom or a deuterium enriched hydrocarbon group containing at least one deuterium atom; with the proviso that when "i" is 0, at least one of $R^{1D}$ and $R^{2D}$ must be present. In one embodiment, the deuterated hydrocarbon group is selected from linear or branched $C_1$–$C_{10}$ alkyl wherein at least 40 percent of the hydrogen atoms on the carbon backbone are replaced by deuterium. In another embodiment, the deuterated hydrocarbon group is selected from linear or branched $C_1$–$C_{10}$ alkyl wherein at least 50 percent of the hydrogen atoms on the carbon backbone are replaced by deuterium. In yet another embodiment, the deuterated hydrocarbon group is selected from linear or branched $C_1$–$C_{10}$ alkyl wherein at least 60 percent of the hydrogen atoms on the carbon backbone are replaced by deuterium.

A further illustrative list of norbornene-type monomers is shown below:

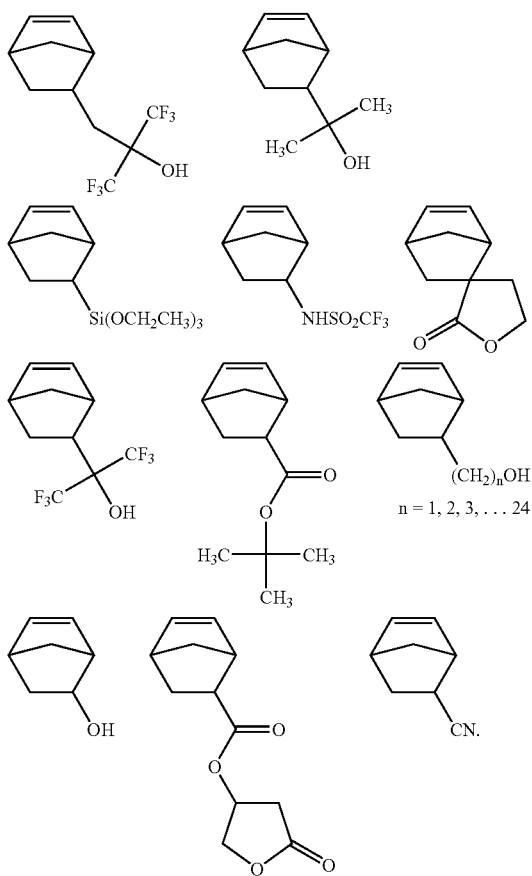

A still further illustrative list of norbornene-type monomers of the present invention includes: bicyclo[2.2.1]hept-5-ene-2-carboxylic acid 5-oxo-4-oxa-tricyclo[4.2.1.03,7]non-2-yl ester, bicyclo[2.2.1]hept-5-ene-2-carboxylic acid 2-methoxy-ethyl ester, bicyclo[2.2.1]hept-5-ene-2-carboxylic acid, bicyclo[2.2.1]hept-5-ene-2-carboxylic acid 2-oxo-tetrahydro-furan-3-yl ester, 4-Oxa-tricyclo [5.2.1.02,6]dec-8-ene-3,5-dione, 4-Oxa-tricyclo [5.2.1.02,6]dec-8-ene-3-one, 1,4,4a,5,6,7,8,8a-Octahydro-1,4-methano-naphthalen-5-ol, 2-bicyclo[2.2.1]hept-5-en-2-yl-propan-2-ol, 2-bicyclo[2.2.1]hept-5-en-2-ylmethyl-1,1,1,3,3,3-hexafluoro-propan-2-ol, 2-bicyclo[2.2.1]hept-5-ene-2-carboxylic acid 1,1,2-trimethyl-propyl ester, 2-bicyclo[2.2.1]hept-5-ene-2-carboxylic acid tert-butyl ester, 2-bicyclo[2.2.1]hept-5-ene-2-carboxylic acid 2-ethyl-adamantan-2-yl ester, 2-bicyclo [2.2.1]hept-5-ene-2-carboxylic acid 2-methyl-adamantan-2-yl ester, 2-bicyclo [2.2.11]hept-5-ene-2-carboxylic acid 1,2,3,3-tetramethyl-bicyclo [2.2.1]hept-2-yl ester, and 2-bicyclo [2.2.1]hept-5-ene-2-carboxylic acid 2-hydroxy-ethyl ester.

Multi-ethylenically unsaturated monomers of the present invention may be incorporated into the addition polymer of the present invention to provide crosslinking either during polymerization, or subsequent to polymerization, or both. Multi-ethylenically unsaturated monomers may be polar olefinic or non-polar olefinic monomers, and the ethylenically unsaturated groups may be identical or different. Useful (meth)acrylic multi-ethylenically unsaturated monomers include, but are not limited to, allyl (meth)acrylate, diallyl phthalate, 1,4-butylene glycol di(meth)acrylate, 1,6-hexanediol di(meth)acrylate, and 1,1,1-trimethylolpropane tri(methyl)acrylate.

Crosslinked polymers can be prepared by copolymerizing the norbornene-type monomer(s) set forth under Structure (B) above with a multifunctional norbornene-type crosslinking monomer(s). By multifunctional norbornene-type crosslinking monomer is meant that the crosslinking monomer contains at least two norbornene-type moieties (norbornene-type double bonds), each functionality being polymerizable in the presence of the catalyst system of the present invention. The crosslinkable monomers include fused multicyclic ring systems and linked multicyclic ring systems. Examples of fused crosslinking agents are illustrated in structures below. For brevity, norbornadiene is included as a fused multicyclic crosslinking agent and is considered to contain two polymerizable norbornene-type double bonds.

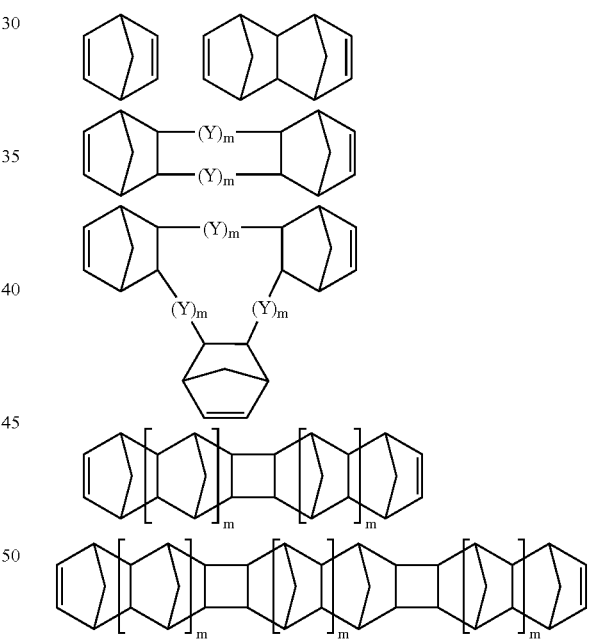

wherein Y represents a methylene (—$CH_2$—) group and m independently represents an integer from 0 to 5, and when m is 0, Y represents a single bond. Representative monomers under the forgoing formulae are disclosed by, for example, Bell et al. in U.S. Pat. No. 6,350,832.

Hydrocarbon groups, R, include, for example, hydrogen, linear and branched $C_1$–$C_{20}$ alkyl, $C_5$–$C_{10}$ cycloalkyl, linear and branched $C_2$–$C_{20}$ alkenyl, $C_6$–$C_{15}$ cycloalkenyl, allylic ligands or canonical forms thereof, $C_6$–$C_{30}$ aryl, $C_6$–$C_{30}$ heteroatom containing aryl and $C_7$–$C_{30}$ aralkyl; each of the foregoing groups can optionally be substituted with hydrocarbyl and/or heteroatom substituents selected from linear or branched $C_1$–$C_5$ alkyl, linear or branched $C_1$–$C_5$ haloalkyl, linear or branched $C_2$–$C_5$ alkenyl and haloalkenyl, halogen, sulfur, oxygen, nitrogen, phosphorus, and phenyl optionally substituted with linear or branched $C_1$–$C_5$ alkyl, linear or branched $C_1$–$C_5$ haloalkyl, and halogen; wherein the cycloalkyl and cycloalkenyl groups may be monocyclic or multicyclic; wherein the aryl groups can be a single ring (e.g., phenyl) or a fused ring system (e.g., naphthyl); wherein the cycloalkyl, cycloalkenyl and aryl groups can be taken together to form a fused ring system; and wherein each of the monocyclic, multicyclic and aryl ring systems may optionally be monosubstituted or multisubstituted with a substituent independently selected from hydrogen, linear and branched $C_1$–$C_5$ alkyl, linear and branched $C_1$–$C_5$ haloalkyl, linear and branched $C_1$–$C_5$ alkoxy, chlorine, fluorine, iodine, bromine, $C_5$–$C_{10}$ cycloalkyl, $C_6$–$C_{15}$ cycloalkenyl and $C_6$–$C_{30}$ aryl.

In the method of polymerizing of the present invention, the cationic metal-pair complex can be used to polymerize: one or more "non-polar olefinic monomers"; one or more "polar olefinic monomers"; or combinations of one or more non-polar olefinic monomers and one or more polar olefinic monomers to form the addition polymer of the present invention. The number average molecular weight, Mn, of the addition polymer of the present invention is: at least 500, at least 1,000, at least 10,000, or at least 20,000; and no more than 5,000,000, no more than 1,000,000, no more than 500,000, or no more than 200,000. The polydispersity of the MWD of the addition polymer of the present invention is: at least 1.000, at least 1.001, at least 1.01, or at least 1.05; and no more than 10, no more than 2.5, no more than 1.5, or no more than 1.1. The MWD of the addition polymer of the present invention may be unimodal or multi-modal, wherein multi-modal includes bimodal and trimodal, as well as higher degrees of modality, and wherein the polydispersity of the MWD for each mode may have the upper and lower limits defined supra.

The "poly(non-polar olefin)" of the present invention is any polymer that can be made from any of the non-polar olefinic monomers of the present invention. The following is a short, non-exhaustive, list of illustrative examples poly (non-polar olefin)s, which may be homopolymers or copolymers: polyethylene, polypropylene, ethylene-propylene copolymers, ethylene-propylene-(non-conjugated diene monomer) ("EPDM") copolymers, LLDPE, polystyrene homo- and copolymers, polybutadiene homo- and copolymers, and polynorbornene. In fact, the poly(non-polar olefin) may include any non-polar olefin capable of insertion addition polymerization in the presence of the cationic metal-pair complex of the present invention.

The "poly(polar olefin)" of the present invention is any polymer that can be made from the polar olefinic monomers of the present invention. The following is short, non-exhaustive, list of illustrative examples poly(polar olefin)s, which may be homopolymers or copolymers: poly[(meth)acrylates] such as poly(methyl methacrylate), poly(butyl acrylate-co-methyl methacrylate), poly[vinylidene halide(s)], poly(vinyl acetate), and poly(vinyl ether). In fact, the poly(polar olefin) may include any polar olefin capable of insertion addition polymerization in the presence of the cationic metal-pair complex of the present invention.

A "poly[(polar olefin)-(non-polar olefin)]" of the present invention is any polymer that can be made from at least one of the non-polar olefinic monomers and at least one of the polar olefinic monomers of the present invention. The following is short, non-exhaustive, list of illustrative examples of poly[(polar olefin)-(non-polar olefin) which copolymers: poly[ethylene-co-methyl (meth)acrylate], poly[octene-co-methyl(meth)acrylate], poly[propylene-co-(meth)acrylate], poly[norbornene-co-(meth)acrylate]. In fact, the poly[(polar olefin)-(non-polar olefin)] may include any polar olefin and any non-polar olefin capable of insertion addition polymerization in the presence of the cationic metal-pair complex of the present invention. The molar ratio of polar olefinic monomers to non-polar olefinic monomers, present as polymerized units in the poly[(polar olefin)-(non-polar olefin)] of the present invention is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

When the addition polymer of the present invention is a copolymer, that copolymer may include, as polymerized units, two, three, four, or more than four different monomers, with no particular limit to the number of different monomers. For example, in one embodiment of the present invention, the poly[(polar olefin)-(non-polar olefin)] is a terpolymer including, as polymerized units, norbornene, 1-octene, and methyl acrylate.

When at least one polar monomer polymerized by the method of the present invention to form a "poly[(polar olefin)-(non-polar olefin)]" is a (meth)acrylate monomer, the molar ratio of (meth)acrylate monomers to non-polar olefinic monomers, present as polymerized units in the poly[(polar olefin)-(non-polar olefin)] of the present invention is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

Further, when both polar olefinic monomers and non-polar olefinic monomers are polymerized together in the polymerization method of the present invention, the molar percentage of monomer incorporated into poly[(polar olefin)-(non-polar olefin)], based on total moles of monomer incorporated into all polymer produced in the polymerization, is: at least 70, at least 80, at least 90 or at least 95; no more than 100, no more than 99, no more than 97.

In particular, when both polar olefinic monomers and non-polar olefinic monomers are polymerized together in the polymerization method of the present invention, and at least one of the polar olefinic monomers is a (meth)acrylate monomer, the molar percentage of monomer incorporated into poly[(polar olefin)-(non-polar olefin)], based on total moles of monomer incorporated into all polymer produced in the polymerization, is: at least 70, at least 80, at least 90 or at least 95; no more than 100, no more than 99, no more than 97.

Still further, when the addition polymer of the present invention is a poly(polar olefin) and at least one of the polar olefinic monomers, incorporated as polymerized units, is a (meth)acrylate monomer, the molar ratio of all (meth)acrylate monomers, present as polymerized units, to all non-(meth)acrylate monomers, present as polymerized units, is: at least 0.05:99.95, at least 0.5:99.5, at least 10:90, at least 20:80, or at least 40:60; or no more than 100:0, no more than 99.5:0.5, no more than 90:10, no more than 80:20, or no more than 60:40.

Similarly, when the addition polymer of the present invention is a poly[(polar olefin)-(non-polar olefin)] and at least one of the polar olefinic monomers, incorporated as polymerized units, is a (meth)acrylate monomer, the molar ratio of all (meth)acrylate monomers, present as polymerized units, to all non-(meth)acrylate monomers, present as polymerized units, is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

When the addition polymer of the present invention includes, as polymerized units, at least one cyclic olefin, incorporated as polymerized units, the molar ratio of all cyclic olefin monomers, present as polymerized units, to all non-(cyclic olefin) monomers, present as polymerized units, is: at least 0.05:99.95, at least 0.5:99.5, at least 10:90, at least 20:80, or at least 40:60; or no more than 100:0, no more than 99.5:0.5, no more than 90:10, no more than 80:20, or no more than 60:40.

Crosslinked polymers can be prepared by copolymerizing the norbornene-type monomer(s) set forth under Structure (B) above with a multifunctional norbornene-type crosslinking monomer(s). By multifunctional norbornene-type crosslinking monomer is meant that the crosslinking monomer contains at least two norbornene-type moieties (norbornene-type double bonds), each functionality being polymerizable in the presence of the catalyst system of the present invention. The crosslinkable monomers include fused multicyclic ring systems and linked multicyclic ring systems. Examples of fused crosslinking agents are illustrated in structures below. For brevity, norbornadiene is included as a fused multicyclic crosslinking agent and is considered to contain two polymerizable norbornene-type double bonds.

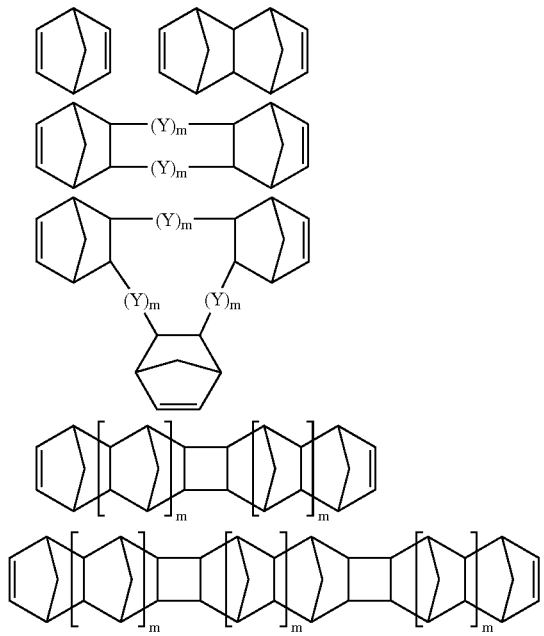

wherein Y represents a methylene (—CH$_2$—) group and m independently represents an integer from 0 to 5, and when m is 0, Y represents a single bond. Representative monomers under the forgoing formulae are disclosed by, for example, Bell et al. in U.S. Pat. No. 6,350,832.

Hydrocarbon groups, R, suitable for use with the present invention include, for example, hydrogen, linear and branched C1–C20 alkyl, C5–C10 cycloalkyl, linear and branched C2–C20 alkenyl, C6–C15 cycloalkenyl, allylic ligands or canonical forms thereof, C6–C30 aryl, C6–C30 heteroatom containing aryl and C7–C30 aralkyl; each of the foregoing groups can optionally be substituted with hydrocarbyl and/or heteroatom substituents selected from linear or branched C1–C5 alkyl, linear or branched C1–C5 haloalkyl, linear or branched C2–C5 alkenyl and haloalkenyl, halogen, sulfur, oxygen, nitrogen, phosphorus, and phenyl optionally substituted with linear or branched C1–C5 alkyl, linear or branched C1–C5 haloalkyl, and halogen; wherein the cycloalkyl and cycloalkenyl groups may be monocyclic or multicyclic; wherein the aryl groups can be a single ring (e.g., phenyl) or a fused ring system (e.g., naphthyl); wherein the cycloalkyl, cycloalkenyl and aryl groups can be taken together to form a fused ring system; and wherein each of the monocyclic, multicyclic and aryl ring systems may optionally be monosubstituted or multisubstituted with a substituent independently selected from hydrogen, linear and branched C1–C5 alkyl, linear and branched C1–C5 haloalkyl, linear and branched C1–C5 alkoxy, chlorine, fluorine, iodine, bromine, C5–C10 cycloalkyl, C6–C15 cycloalkenyl and C6–C30 aryl.

The method of preparing the addition polymer of the present invention can be carried out at a reaction temperature (° C.) of: at least –100° C., at least –50° C., at least 0° C., or at least 20° C.; and no more than 200° C., no more than 160° C., no more than 140° C., or no more than 120° C. This method can be carried out at a pressure (in atmospheres, i.e., the pressure inside the reactor is 1.0 atmosphere for a value of 1.0) of: at least 0.01, at least 0.1, at least 0.5, or at least 1.0, and no more than 1,000, no more than 100, no more than 10, or no more than 5. Further, the molar ratio of ethylenically unsaturated monomer to the cationic metal-pair complex of present invention is: at least 50:1, at least 200:1, at least 250:1, or at least 1,000:1, and no more than 5,000,000:1, no more than 2,000,000:1, or no more than 500,000:1, no more than 250,000:1, or no more than 100,000:1. For gaseous monomers at high pressures, in particular constant high pressures, e.g., equal to or greater than 400 psi, the molar ratio of ethylenically unsaturated monomer to the cationic metal-pair complex of present invention may be even higher than 5,000,000:1, for example, no more than 6,000,000:1, no more than 8,000,000:1, or even higher. In the method of polymerization of the present invention, the amount of diluent, expressed as volume (milliliters) of diluent per millimole of the cationic metal-pair complex of the present invention, is: at least 0.0, at least 10, at least 50, or at least 100; and no more than 10,000,000, no more than 1,000,000, no more than 100,000, no more than 10,000, or no more than 5,000.

When particles of the addition polymer are produced by the method of preparing the addition polymer of the present invention, depending on the particular details of that method, the polymer particles have a mean particle diameter (i.e., mean particle size), expressed in microns, of: at least 0.002, at least 0.04, at least 0.1, or at least 0.8; and no more than 500, no more than 20, no more than 10, no more than 5, or no more than 3. The PSD polydispersity of the particles is: at least 1, at least 1.001, at least 1.01, or at least 1.05; and no more than 10, no more than 5, no more than 1, no more than 1.3, or no more than 1.1. The PSD of the addition polymer of the present invention may be unimodal or multi-modal, wherein multi-modal includes bimodal and trimodal, tetramodal, as well as higher degrees of modality, and wherein the polydispersity of the PSD for each particle size mode may have the upper and lower limits defined supra. One skilled in the art of catalytic polymerization will further recognize that it is even possible to prepare particles having a mean particle diameter greater than 1000 microns (1 millimeter). This may happen, for example, as the result of evaporation during or after solution or bulk polymerization, or polymerization involving polymer precipitation. In this way, even larger monolithic polymer structures may be formed.

The method for preparing the addition polymer of the present invention may be carried out in bulk or in a diluent. If the catalytic composition is soluble in the one or more ethylenically unsaturated monomers to be polymerized, it may be convenient to carry out the polymerization in bulk. Such bulk polymerizations may be carried out, for example, in batch or continuous mode, or by reaction injection molding or other mold based techniques. In another embodiment of the present invention, the polymerization is carried out in a diluent. Any organic or aqueous diluent which does not adversely interfere with the catalytic composition and is a solvent for the monomers may be employed. Illustrative examples of organic solvents are: aliphatic (non-polar) hydrocarbons, e.g., hexane and heptane; alicyclic hydrocarbons, e.g., cyclohexane; aromatic hydrocarbons, e.g., toluene; halogenated (polar) hydrocarbons, e.g., methylene chloride and chlorobenzene. For polymerization systems in which the catalytic composition is not degraded, the diluent may be water, solvents miscible with water, and combinations thereof. The diluent may further include, for example, any of the fugitive substances disclosed in US patent application 2002/0110690, e.g., 2,2-dimethylpropane, 1,1-difluoroethane, 1,1,1,2-tetrafluoroethylene propane (−42.1° C.), carbon dioxide, and tetrafluoromethane (−130° C.).

The diluent of the present invention may also be an "ionic liquid". Ionic liquids are either organic salts or mixtures of salts that are fluid at room or near-room temperature (see: Dupont, J. *Chem. Rev.* 2002, 102, 3667; Kabisa, P. *Prog. Poly. Sci.* 2004, 29, 3). A property of ionic liquids is their zero vapor pressure, making them potential solvents for zero-(volatile organic) chemical processes and possible alternative for supercritical $CO_2$. Ionic liquids are, for example, composed of bulky 1,3-dialkylimidazolium, alkylammonium, alkylphosphonium or alkylpyridinium organic cations and inorganic anions such as most frequently $AlCl_4^-$, $BF_4^-$ or $PF_6$ but also $NO_3$, $ClO_4$, $CF_3CO_2$, $CF_3SO_3$ or $CH_3CO_2$ and other anions. The most commonly used neutral ionic liquids include 1-butyl-3-methylimidazolium hexafluorophospate or tetrafluoroborate abbreviated as [bmim] [PF6] and [bmim] [BF4] correspondingly.

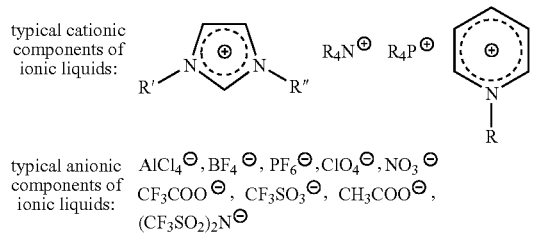

typical cationic components of ionic liquids:

typical anionic components of ionic liquids: $AlCl_4^\ominus, BF_4^\ominus, PF_6^\ominus, ClO_4^\ominus, NO_3^\ominus$
$CF_3COO^\ominus, CF_3SO_3^\ominus, CH_3COO^\ominus,$
$(CF_3SO_2)_2N^\ominus$ When utilized in the preparation of the addition polymer of the present invention, the monomers and/or catalytic composition of the present invention may not be fully soluble, or may even be insoluble, in the diluent. This situation might, for example, occur in heterogeneous systems wherein the locus of polymerization must be accessed by both catalytic composition and ethylenically unsaturated monomer. In such cases, it may be advantageous to employ one or more transport agents to transport monomers, or the complexes of the catalytic composition, to the desired locus of polymerization. For example, transport agents such as cyclodextrins may be advantageously employed to transport ethylenically unsaturated monomers having low, or very low, water solubility, across the aqueous phase to polymer particles during aqueous emulsion polymerization.

In addition to being carried out as bulk and solution polymerizations, the polymerizations of the present reaction can be carried out in the gas phase in, for example fluidized bed or stirred tank reactors, optionally in the presence of prepolymer for control of the size and shape of polymers formed. Polyethylene, polybutene, polyhexene, and related copolymers, including copolymers containing, for example, methyl methacrylate may be prepared by gas phase polymerization.

A still further method for producing the addition polymer of the present invention may be any appropriate method known to the art, including, but not limited to emulsion polymerization, suspension polymerization, microemulsion polymerization, mini-emulsion, and slurry polymerization. Descriptions of emulsion polymerization methods are disclosed in Blackley, D.C. Emulsion Polymerisation; Applied Science Publishers: London, 1975; Odian, G. Principles of Polymerization; John Wiley & Sons: New York, 1991; Emulsion Polymerization of Acrylic Monomers; Rohm and Haas, 1967. The method of the present invention further includes methods disclosed in published U.S. patent application US2003/0007990.

The cationic metal-pair complex of the present invention is suitably employed as an unsupported material. Alternatively, any of the complexes of the present invention may be supported on an "inorganic solid carrier" ("inorganic carrier") or an "organic polymeric solid catalyst carrier" ("organic carrier") which is normally solid under reaction conditions and is heterogeneous, i.e., is substantially insoluble in the reaction medium. Used herein, the terms "carrier" and "support" are used interchangeably. Illustrative of suitable inorganic carriers are inorganic acidic oxides such as alumina and inorganic materials known as refractory oxides. Suitable refractory oxides include synthetic components as well as acid treated clays and similar materials such as kieselguhr or crystalline macroreticular aluminosilicates known in the art as molecular sieves. In general, synthetic catalyst carriers are preferred over natural occurring materials or molecular sieves. Exemplary synthetic catalyst carriers include alumina, silica-alumina, silica-magnesia, silica-alumina-titania, silica-alumina-zirconia, silica-titania-zirconia, silica-magnesia-alumina, magnesium chloride, and the like. Organic carriers include, for example, macroreticular resins which may, or may not, bear polar functional groups or carbon-carbon double bonds.

In general, proportions of cationic metal-pair complex, or precursor complex of the present invention, in percent by weight, based on the weight of catalyst carrier, are: at least 0.001%, at least 0.01%, at least 0.1%, or at least 1.0%; and no more than 500%, no more than 100%, no more than 70%, no more than 20%, or no more than 5%. The cationic metal-pair complex is introduced onto the carrier in any suitable manner. In one modification, the supported cationic metal-pair complex is prepared by intimately contacting the preformed cationic metal-pair complex and the carrier in an inert diluent, which may or may not be the same inert diluent employed for preparing the cationic metal-pair complex. In another modification, the cationic metal-pair complex can be prepared directly on the catalyst carrier support surface by contacting the cationic metal-pair complex precursors in the presence of the catalyst carrier in a suitable inert diluent. In addition to the supports enumerated supra, the cationic metal-pair complex of the present invention can be supported on any of the supports or matrices disclosed in published U.S. patent applications US2002/60226997, US2002/0052536, in U.S. patent applications Ser. No. 60/383,650 and U.S. Ser. No. 60/440,142., and in Chen and Marks, *Chem. Rev.*, 100, 1391–1434, 2000.

One skilled in the art will recognize that, when aqueous emulsion polymerization and microemulsion polymerization are used to prepare the addition polymer of the present invention, surfactants will, optionally, be present in the reaction medium. Conventional surfactants may be used to stabilize the emulsion polymerization systems before, during, and after polymerization of monomers. For emulsion polymers, these conventional surfactants will usually be present at levels of 0.1 percent to 6 percent by weight based on the weight of total monomer, whereas microemulsion polymerizations may require level as high as 30 weight %. Useful surfactants include,: anionic surfactants, for example, sodium lauryl sulfate and sodium dodecyl benzene sulfonate; nonionic surfactants, for example, glycerol aliphatic esters and polyoxyethylene aliphatic esters; and amphoteric surfactants, for example, aminocarboxylic acids, imidazoline derivatives, and betaines.

Methods for generating cationic mono-metallic complexes by treating their neutral precursors with stoichiometric (i.e., one equivalent per metal atom) or excess amounts of activator component are disclosed in Chen, E. Y.-X.; Marks, T. *J. Chem. Rev.* 2000, 100, 1391 and Mecking, S. *Coord. Chem. Rev.* 2000, 203, 325.

In the method of preparing the catalytic composition of the present invention, a cationic metal-pair complex is generated by treating a precursor complex using amounts of activator component suitable to remove leaving group Y. The leaving group Y is replaced with at least one replacement moiety in an amount sufficient to at least fill any coordination sites, of metal atoms $M^1$ and $M^2$, vacated by the removal of said leaving group Y, to form said cationic metal-pair complex.

The precursor complex from which the leaving group Y is removed may be a full-(metal pair) complex or a first semi-(metal pair) complex. When the precursor is a first semi-(metal pair) complex, the leaving group Y is replaced by a second semi-(metal pair) complex. The temperature (° C.) for the reaction generating the cationic metal-pair complex is: at least −100° C., at least −50° C., at least 0° C., or at least 20° C.; and no more than 200° C., no more than 160° C., no more than 140° C., or no more than 120° C. In the method of preparation of the cationic metal-pair complex of the present invention, the amount of diluent, expressed as volume (milliliters) pre millimole of cationic metal-pair complex, is: at least 0.0, at least 2, at least 5, or at least 10; and no more than 1,000, no more than 500, no more than 200, or no more than 100. Useful diluents include any of the non-aqueous diluents (vide supra) useful in carrying out the polymerization of the ethylenically unsaturated monomers of the present invention. In cases in which neither the precursor complex nor the cationic metal-pair complex is adversely affected, water or water miscible diluents may be utilized as well.

In one embodiment of the method of the present invention for preparing, from a full-(metal-pair) precursor complex, a cationic metal-pair complex, the removal of leaving group Y is represented by the following reaction scheme:

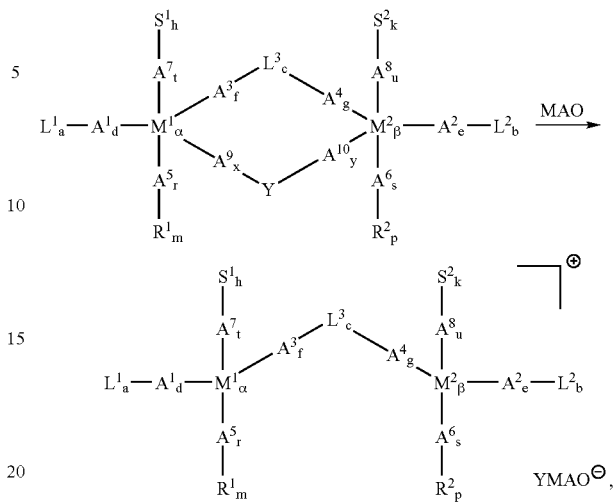

wherein the activator component is MAO or modified MAO.

In another embodiment of the method of the present invention, the cationic metal-pair complex is formed by: oxidative cleavage of the bond between first metal atom, $M^1$, and a leaving group Y and of the bond between second metal atom, $M^2$, and that leaving group Y of a full-(metal-pair) precursor complex. This embodiment is represented by the following reaction scheme:

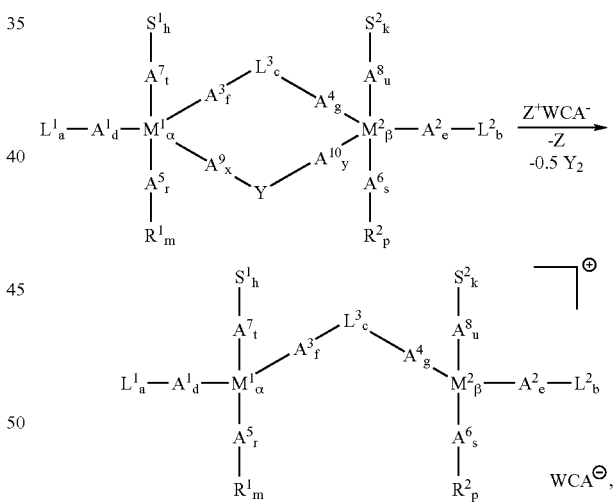

wherein the activator component is $Z^+WCA$: and $Z^+$ may be, for example, $Ag^+$ or $Cp_2Fe^+$. Used herein, "Cp" denotes "cyclopentadienyl", and $Cp_2Fe^+$ denotes the "ferricenium ion".

In a further embodiment of the method of the present invention, the cationic metal-pair complex is formed by: abstractive cleavage of the bond between first metal atom, $M^1$, and the leaving group Y, and of the bond between second metal atom, $M^2$, and the leaving group Y of a full-(metal-pair) precursor complex. This embodiment is represented by the following reaction scheme:

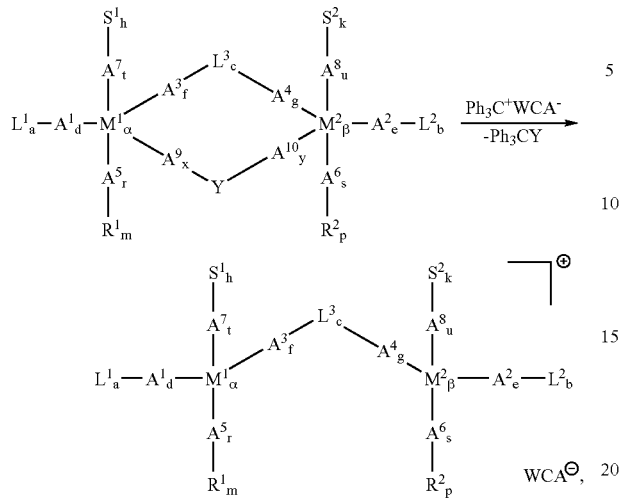

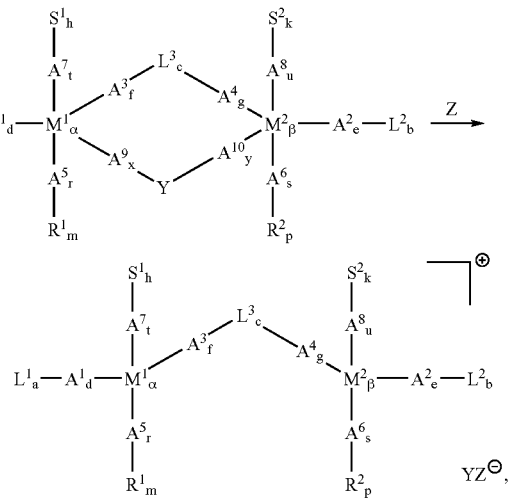

wherein the activator component is, for example, $Ph_3C^+$ WCA⁻. Used herein $Ph_3C^+$ is the "trityl cation", also denoted "triphenyl carbocation".

In a still further embodiment of the method of the present invention, the cationic metal-pair complex is formed by protonolysis of the bond between first metal atom, $M^1$, and the leaving group Y, and of the bond between second metal atom, $M^2$, and the leaving group Y of a full-(metal-pair) precursor complex. This embodiment is represented by the following reaction scheme:

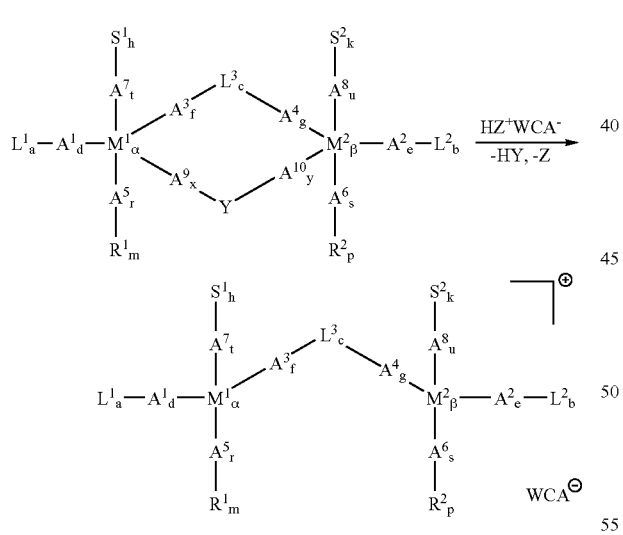

wherein, for example, Z is: $NR_jAr_k$ (wherein R is a methyl or other alkyl group; Ar is a phenyl or other aryl group); $(OEt_2)_2$; first or second labile ligand; some other labile neutral electron donor ligand that is present, but does not become part of the cationic metal-pair complex.

In yet another embodiment of the method of the present invention, the cationic metal-pair complex is formed by abstraction by a neutral Lewis acid of leaving group Y of a full-(metal-pair) precursor complex. This embodiment is represented by the following reaction scheme:

wherein Z is the Lewis acid and, for example, $Z=B(C_6F_5)_3$ or other $B(Ar^F)_3$ compounds. "$Ar^F$" denotes "fluoroaryl", and "YZ⁻" serves as weakly coordinating anion, WCA⁻.

In another embodiment of the method of the present invention, the cationic metal-pair complex is formed by abstraction by silver, thallium or alkali metal salts of leaving group Y of a full-(metal-pair) precursor complex. This embodiment is represented by the following reaction scheme:

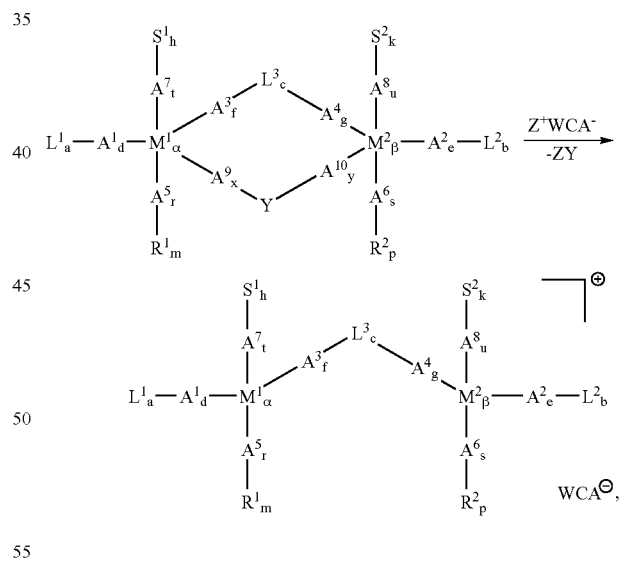

wherein, for example, Z=Ag, Tl, Li, Na, K, or Cs.

In another embodiment of the method of the present invention, a first semi-(metal pair) precursor complex is combined with any of the above activator components, (e.g., silver salt) to remove leaving group Y, and leaving group Y is replaced by a second semi-(metal pair) precursor complex during or after the removal of leaving group Y from the first semi-(metal pair) complex. It is understood that bridging moiety $L^3$ in the following schemes is derived from a first ligand or first anionic hydrocarbyl radical of a precursor complex.

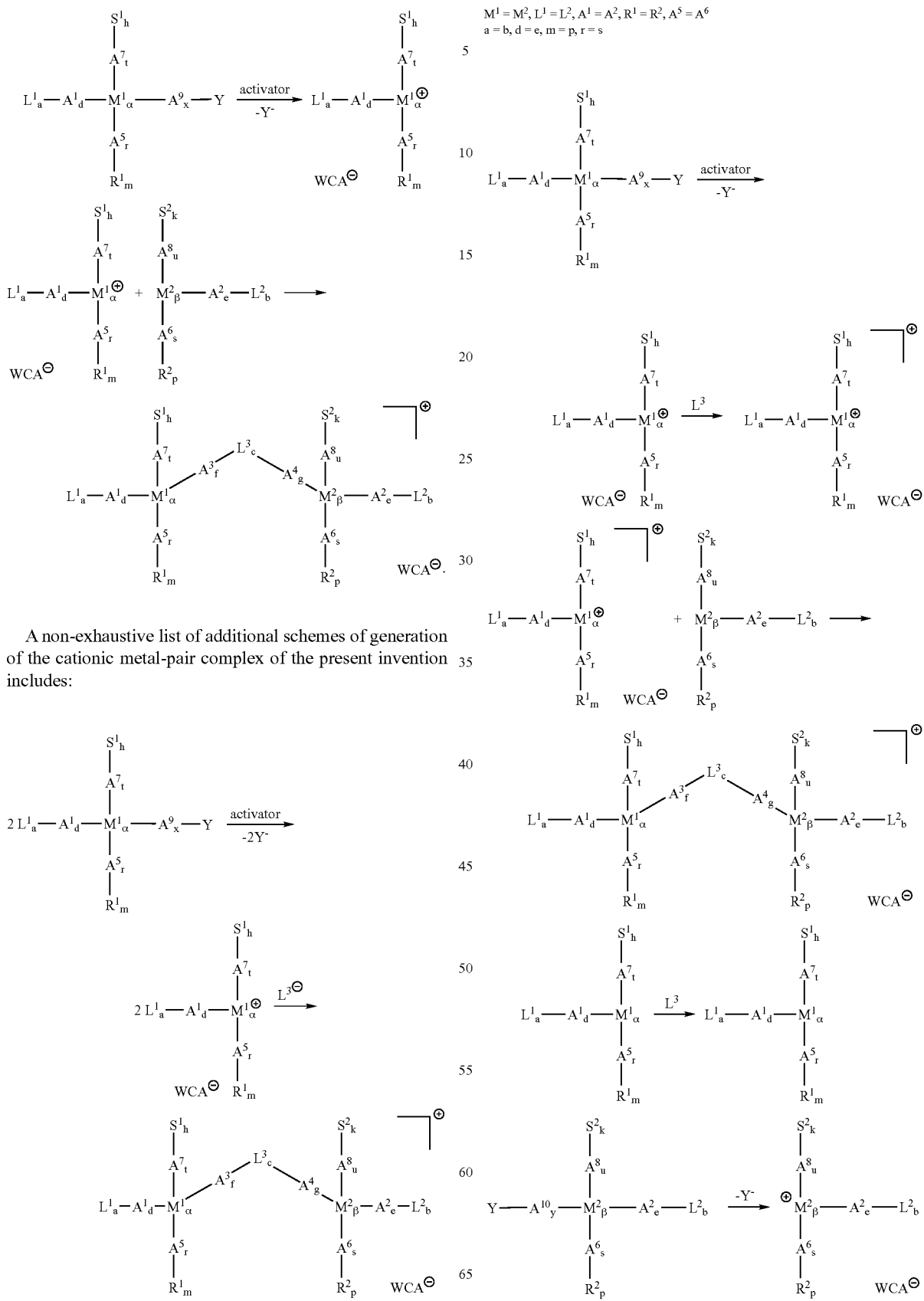
A non-exhaustive list of additional schemes of generation of the cationic metal-pair complex of the present invention includes:

-continued

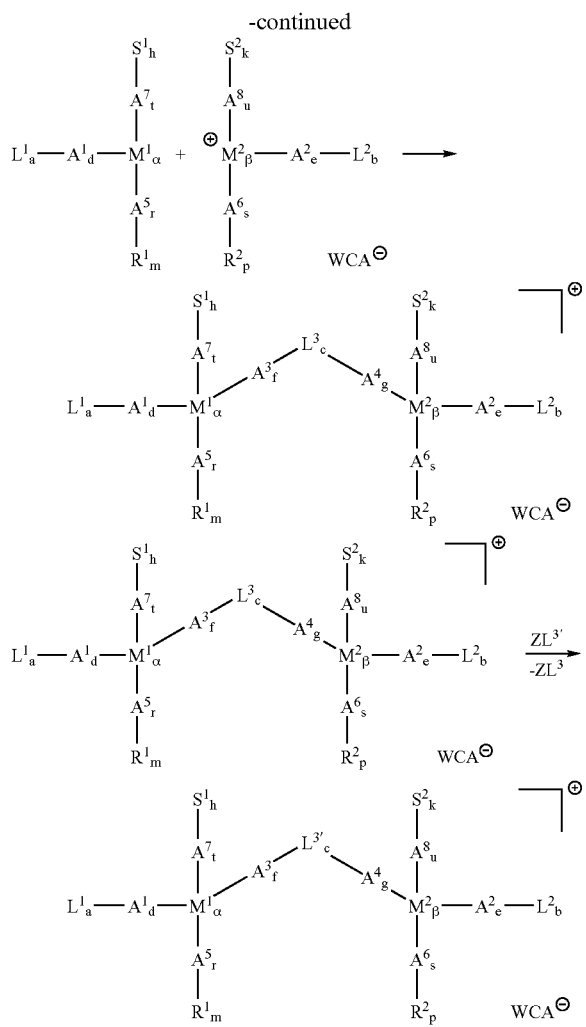

The following is an example of the reaction using $ZL^{3'}$ (immediately above):

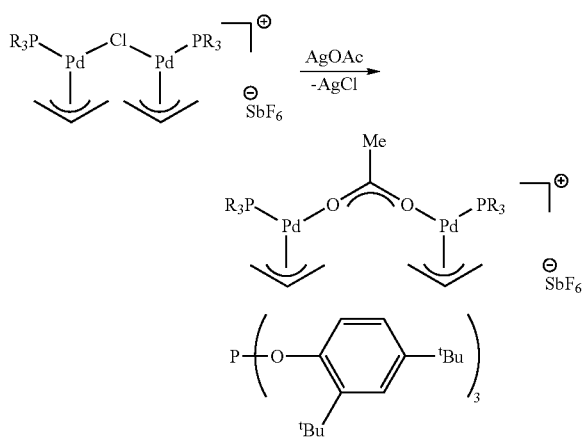

In another embodiment of the method of preparing the cationic metal-pair complex of the present invention, any of the preceding reaction schemes may be carried out in the presence of an inorganic support, an organic polymeric support, a pair-coupling moiety, or a combination thereof. Within this embodiment, a non-exhaustive list of ways in which a support or pair-coupling moiety may be utilized includes: combination with a precursor complex, followed by addition of an activator component; combination with of an activator component, followed by addition of a precursor component; when a first semi-(metal pair) precursor complex is involved and the first semi-(metal pair) precursor complex is not already associated with a support, combining the first semi-(metal pair) precursor complex with a support and then reacting it with the second semi-(metal pair) precursor complex, or combining the first semi-(metal pair) precursor complex with a supported second semi-(metal pair) precursor complex; or combining the cationic metal-pair complex and a support.

The addition polymers prepared using the catalytic composition of the present invention afford many new products and market opportunities currently unachievable. Applications for the polymers include polymers useful in preparation of photoresists, polymers useful in electronics, polymers useful in computer components and microcomponents, polymers useful as plastics additives (e.g., heat distortion temperature improvers, impact modifiers, and processing aids), UV stable thermoplastic elastomers, colorable (including dyeable) polyolefin plastics and other polymers, and new low-cost, high melting point, optical polymers. The polymers of the present invention include polymers that, while having polyolefin type attributes, are also paintable, or otherwise coatable without recourse to pretreatment which adds expense and often creates environmental hazard. Applications further include paint binders that can undergo film formation in the absence of coalescents while still providing paints that are both durable and dirt-resistant, enabling productions of, for example, aqueous and powder formulations having reduced or zero concentrations of volatile organic compounds (VOCs) without sacrificing paint properties. Polymers selected from those of the present invention may be the principal, sole, or minor components of coatings (paints, stains, varnishes, adhesives and mastics) for essentially any substrate, including non-polar and polar thermoplastics, thermoset plastics, other organic and inorganic polymers, glass, stone, ceramic, wood, particle board, paper, leather, concrete, asphalt, cement, and metal. Whether the polymers of the present invention are included in the coating, the substrate, or both, the resulting coated substrates can, for example, be decorative and/or of enhanced durability, attributes that are highly desirable in, for example, vehicular, appliance, architectural, household, device housing (including electronic), decorative design, and ornamental applications.

Polymers of the present invention are further useful as ionomers for applications requiring extreme toughness (e.g., golf ball covers) or superior sealing properties (e.g., bacon packaging). They find further utility as thermoplastics, as thermosets, and as compatibilizers, affording compatible blends of non-polar and polar polymers with enhanced properties compared with the component polymers. They find still further utility as impact and processing enhancing additives for thermoplastic and thermoset resins. When functionalized appropriately, these polymers behave as colorants, UV and other radiation absorbers, and photosensitizers. When combined with active ingredients of various types, they can enable delivery of those ingredients to targeted loci. Such active ingredients include, pharmaceutical, pesticides, other biologically active substances, colorants and other optically active substances, and analytical tags, The polymers of the present invention are useful inter alia in electronic and optical applications. They are useful as components in resist materials utilized in the manufacture of integrated circuits (ICs). The patterning of IC's is carried out according to various lithography techniques known in the art. Polymers of the present invention that contain acid labile groups pendant from the backbone can be used in radiation sensitive photoresist compositions. (J. V. Crivello et al., Chemically Amplified Electron-Beam Photoresists, Chem. Mater., 1996, 8, 376–381). Electronic applications further include, but are not limited to, dielectric films (i.e., multichip modules and flexible circuits), chip attach adhesives, underfill adhesives, chip encapsulants, glob tops, near hermetic board and chip protective coatings, embedded passives, laminating adhesives, capacitor dielectrics, high frequency insulator/connectors, high voltage insulators, high temperature wire coatings, conductive adhesives, reworkable adhesives, photosensitive adhesives and dielectric film, resistors, inductors, capacitors, antennas and printed circuit board substrates. In optical applications uses include but are not limited to optical films, ophthalmic lenses, wave guides, optical fiber, photosensitive optical film, specialty lenses, windows, high refractive index film, laser optics, color filters, optical adhesives, and optical connectors.

Some embodiments of the invention will now be described in detail in the following Examples. Some of the chemicals used in the Examples are listed in Table II.

TABLE II

Chemicals used the preparations of the examples.

| Chemical (purity) | Source | CAS # |
|---|---|---|
| (Allyl)palladium-(tricyclohexylphosphine)chloride: | (a) | |
| 1,3-Bis(3,5-di-tert-butylpyrazolyl-1-carbonyl)benzene | (b) | |
| Allylpalladium chloride dimer (99%) | Strem, Newburyport, MA 01950-4098 | 12012-95-2 |
| 4-tert-Butyl-2,6-diformylphenol (96%) | Aldrich, Milwaukee, WI 53201 | 84501-28-0 |
| Chlorobenzene | Aldrich | 108-90-7 |
| Dichloromethane (99+%) | Aldrich | 75-09-2 |
| Diethyl ether (99+) | Aldrich | 60-29-7 |
| 2,6-Diisopropylaniline (97%) | Aldrich | 24544-04-5 |
| Hexanes (98+) | Aldrich | 73513-42-5 |
| Hexafluoroisopropanol norbornene, 5-R-NB (R = $CH_2C(CF_3)_2OH$) | | 196314-61-1 |
| Lithium tetrakis-(pentafluorophenyl)borate etherate | Boulder Scientific, Boulder, CO BSC-353 | |
| Methallylnickel chloride dimer | Strem | 12145-60-7 |
| Methylaluminoxane (30 wt % in Toluene) | Albemarle, Baton Rouge, LA | |
| Pentane (99+%) | Aldrich | 109-66-0 |
| Q-5 oxygen scavenger | Engelhard, Iselin, NJ 08830 | |
| Silver hexafluoroantimonate (98%) | Aldrich | 12005-82-2 |
| Silver hexafluorophosphate (99.99%) | Aldrich; Acros Organics, Belgium | 26042-63-7 |
| Sodium Hydride (60% dispersion in mineral oil) | Aldrich | 7646-69-7 |
| Sodium tetrakis [3,5-bis(trifluoromethyl)phenyl]-borate (98+) | Aldrich | 79060-88-1 |
| Tetrahydrofuran (99+) | Aldrich | 109-99-9 |
| p-Toluenesulfonic acid monohydrate (98%) | Aldrich | 55415-4 |
| Tricyclohexylphosphine (97%) | Strem | 2622-14-2 |
| Tris(2,4-di-tert-butylphenyl)-phosphite (98+) | Strem | 31570-04-4 |
| 1-octene (99+%) | Acros | 111-66-0 |

(a) Prepared according to the literature method of DiRenzo, G. M.; White, P. S.; Brookhart, M. J. Am. Chem. Soc. 1996, 118, 6225).;
(b) Prepared according to the literature method of Guzei, I. A., et al., S. F. Dalton Trans., 2003, 715-722.

General procedures. The polymerization reactions of Comparative Examples 1–5 and Examples 1–19 were set up within a dry box under a nitrogen atmosphere. After the reaction was set up, the glass vessel was sealed, removed from the dry box, and heated using water bath in a fume hood.

Nitrogen was purified by passage through columns containing activated molecular sieves and Q-5 oxygen scavenger. Toluene was purified by passage through columns of activated molecular sieves (4 Å)/alumina/O2 remover (e.g., Q-5) and methylene chloride was purified by passage through columns of activated alumina. Lithium tetrakis (pentafluorophenyl)borate etherate was purchased from Boulder Scientific, allylpalladium chloride dimer (99%) and tricyclohexylphosphine (97%) were purchased from Strem, silver hexafluorophosphate (98%) was purchased from Acros, and all were used without further purification. Methyl acrylate (99%) was purchased from Aldrich and purified by passage through columns of MEHQ inhibitor remover and activated molecular sieves (4 Å), and purged with nitrogen for 0.5 hour. Norbornene (99%) was purchased from Acros and purified using one of the following two methods: 1) It was dried with calcium hydride at 60° C. overnight, degassed by freeze-pump-thaw twice and vacuum transferred at 50° C. to a dry glass receiver; 2) It was dissolved in a small amount of toluene to yield a clear colorless solution, which was passed through a column of activated molecular sieves (4 Å) and purged with nitrogen for 0.5 hour. The concentration of this toluene solution of norbornene was determined by $^1$H NMR analysis. Hexafluoroisopropanol norbornene and chlorobenzene each was sparged with nitrogen for 0.5 hours and then purified by passage over a column containing alumina and molecular sieves (3 Å). 1-octene was sparged with nitrogen for 0.5 hours and then purified by passage through a column containing alumina and molecular sieves (4 Å).

Nuclear Magnetic Resonance (NMR) Spectroscopy. NMR spectra were recorded on Varian 600, Bruker DMX-400 or DEX-500 spectrometers at 23° C. unless otherwise indicated. $^1$H and $^{13}$C chemical shifts are reported vs. $SiMe_4$ and were determined by reference to residual $^1$H and $^{13}$C solvent signals.

Molecular Weight Determination using Gel Permeation Chromatography (GPC). Gel Permeation Chromatography, otherwise known as size exclusion chromatography, actually separates the members of a distribution of polymer chains according to their hydrodynamic size in solution rather than their molar mass. The system is then calibrated with standards of known molecular weight and composition to correlate elution time with molecular weight. The techniques of GPC are discussed in detail in Modern Size Exclusion Chromatography, W. W. Yau, J. J Kirkland, D. D. Bly; Wiley-Interscience, 1979, and in A Guide to Materials Characterization and Chemical Analysis, J. P. Sibilia; VCH, 1988, p.81–84.

All samples were prepared at concentration 2 mg/mL in THF or chloroform (HPLC grade) and gently stirred to dissolve the polymer sample completely. All polymer solutions were filtered using 1 μm PTFE filter. GPC separation were performed using 2 PL gel Mixed B columns and evaporative light scattering detector (ELSD). Typical chromatographic conditions: 2 PL gel MIXED B columns, particle size 5 μm; eluent: THF or CHCl3 (HPLC grade), 1.0 ml/min; injected volume of sample solution: 50 μL; PS standards with molecular weight ranging from 580 to 2 560 000 g/mol (0.5 mg/mL in THF or CHCl3) were used to construct calibration curve; ELS detection, (TN=40° C., TECH=80° C., Fnitrogen=1 L/min).

Liquid Chromatography—NMR. Typical LC-NMR experiment conditions: a sample was dissolved in $CDCl_3$ to form a solution (ca. 1%) and filtered through a 0.2 micron filter. The polymer separation was carried out on a SUPLE-COSIL reverse-phase C-18 column (25 cm×4.6 mm), with a flow rate of 1 ml/min. The Evaporative Light Scattering detection (ELSD) and UV detectors were employed with a solvent gradient of acetonitrile/water/THF from 95/5/0 to 0/0/100 in 24 minutes. LC-$^1$HNMR spectra were acquired on a Varian UNITY INOVA 600 MHz NMR spectrometer.

Differential Scanning Calorimetry (DSC): Modulated Differential Scanning Calorimetry measurements were carried out on a Q-1000 Series DSC made by TA Instruments. Samples were run under an inert atmosphere of nitrogen at a flow rate of 25 mL/min. Samples were heated from −90° C. to +380° C. at a rate of 7° C./min with a modulation amplitude of 1° C. and a period of 40 s.

COMPARATIVE EXAMPLE 1

Use of the Catalyst Precursor of U.S. Pat. No. 6,303,724 as Catalyst for the Polymerization of Monomers Methyl Acrylate and Norbornene The polymeric mixture produced infra utilizing that catalyst precursor is not a copolymer of methyl acrylate and norbornene, but rather a mixture of two components, as clearly elucidated by the more in-depth analyses used in this Comparative Example 1.

A 2 mL vial was charged with allylpalladium chloride dimer (9.6 mg, 0.026 mmol). Toluene (1 mL) was added to yield a clear yellow solution. A second 2 mL vial was charged with tricyclohexylphosphine (14.6 mg, 0.052 mmol). Toluene (1 mL) was added to the second vial to yield a clear colorless solution. A third 2 mL vial was charged with lithium tetrakis(pentafluorophenyl)borate etherate (43.4 mg, 0.052 mmol). Toluene (1 mL) was added to the third vial to yield a colorless slurry. The three catalyst precursors were mixed in a 5 ML vial to yield a brownish yellow solution instantaneously. The brownish yellow solution was then added to a 100 ML serum bottle containing norbornene (1.13 g, 12 mmol), methyl acrylate (1.0 g, 12 mmol) and toluene (17 mL) to form a clear yellow solution. The bottle was sealed and stirred at 50° C. for 17.5 hours, after which the reaction mixture was poured into acidified methanol (250 mL; HCl, 1M) to yield a yellow solution with fine white solids. The mixture was filtered to yield a yellow solid, which was dried under vacuum at 50° C. overnight. A yellow solid (0.134 g) was collected. $^1$H NMR analysis revealed that the product has an overall molar ratio of 44 (norbornene): 56 (methyl acrylate). GPC analysis revealed a bimodal pattern: Peak 1, Mw 25000, Mn 20000, Mw/Mn 1.25; Peak 2, Mw 1300, Mn 1000, Mw/Mn 1.30. The ratio of the areas under peaks 1 and 2 was roughly 1:1.

COMPARATIVE EXAMPLE 2

Use of the Catalyst Precursor of U.S. Pat. No. 6,303,724 as Catalyst for the Polymerization of Monomers Methyl Acrylate and Norbornene The polymeric mixture produced infra utilizing that catalyst precursor is a mixture of two components, as clearly elucidated by the more in-depth analyses used in this Comparative Example 2.

A 2 ML vial was charged with allylpalladium chloride dimer (9.6 mg, 0.026 mmol). Toluene (1 mL) was added to yield a clear yellow solution. A second 2 mL vial was charged with tricyclohexylphosphine (14.6 mg, 0.052 mmol). Toluene (1 mL) was added to yield a clear colorless solution. A third 2 ML vial was charged with lithium tetrakis(pentafluorophenyl)borate etherate (43.4 mg, 0.052 mmol). $CH_2Cl_2$ (2 mL) was added to yield a clear colorless solution. The three catalyst precursors were mixed in a 5 ML vial to yield a brownish yellow solution instantaneously, which was then added to a 100 ML serum bottle containing norbornene (1.13 g, 12 mmol), methyl acrylate (1.0 g, 12 mmol) and toluene (16 mL) to form a clear yellow solution. The bottle was sealed and stirred at 50° C. for 20 hours, after which the reaction mixture was poured into acidified methanol (250 mL; HCl, 1M) to yield a yellow solution with fine white solids. The mixture was filtered to yield a yellow solid and a colorless filtrate. The solid was dried under vacuum at 60° C. overnight. A yellow solid (0.247 g) was collected. $^1$H NMR analysis showed that the product has an overall molar ratio of 37 (norbornene): 63 (methyl acrylate). GPC exhibited a bimodal pattern: Peak 1, Mw 26500, Mn 20000, Mw/Mn 1.33; Peak 2, Mw 1300, Mn 900, Mw/Mn 1.44. The ratio of the areas under peaks 1 and 2 was roughly 1:1. The two components were separated by GPC on a preparative scale. $^1$H NMR analysis revealed that the high MW fraction had a molar ratio of 89:11 for methyl acrylate:norbornene and the low MW fraction was essentially a homopolymer of norbornene. Each fraction remaind a single peak in HPLC chromatograms.

COMPARATIVE EXAMPLE 3

Use of the Catalyst Precursor of U.S. Pat. No. 6,303,724 as Catalyst for the Polymerization of Monomers Methyl Acrylate and Norbornene This comparative example utilizes the catalyst preparative method and catalyst precursor described in Example 8 of U.S. Pat. No. 6,303,724 i.e., combining allylpalladium chloride dimer with tricyclohexyl-phosphine first, and then adding lithium tetrakis(pentafluorophenyl)borate etherate. The polymeric mixture produced infra utilizing that catalyst precursor is a mixture of two components, as clearly elucidated by the more in-depth analyses used in this Comparative Example 3.

Stock solutions of allylpalladium chloride dimer (9.6 mg/mL), tricyclohexylphosphine (14.6 mg/mL) and lithium tetrakis(pentafluorophenyl)borate etherate (43.4 mg/mL) were prepared using $CH_2Cl_2$ for each individual catalyst precursor. Solutions of allylpalladium chloride dimer (4 mL) and tricyclohexylphosphine (4 mL) were pre-cooled at −35° C. before being mixed to yield a clear yellow solution, which was added to the lithium tetrakis(pentafluorophenyl)borate etherate solution (4 mL) to form a white slurry in a yellow solution. 3 mL of the mixture was added to a 100 mL serum bottle which contained norbornene (2.26 g, 24 mmol, pre-dissolved in toluene, 86 wt %), methyl acrylate (2.0 g, 24 mmol) and toluene (15 mL) to form a clear yellow solution. The bottle was sealed and stirred at 60° C. for 18 hours, after which the reaction mixture was poured into methanol (250 mL) to yield a yellow slurry in a colorless solution. The mixture was filtered to yield a yellow solid and a slightly yellow filtrate. The solid was dried under vacuum at 60° C. overnight. A yellow solid (0.565 g) was collected. GPC analysis revealed a bimodal pattern: Peak 1, Mw 38000, Mn 27000, Mw/Mn 1.41; Peak 2, Mw 1280, Mn 860, Mw/Mn 1.48.

COMPARATIVE EXAMPLE 4

Use of the Catalyst Precursor of U.S. Pat. No. 6,303,724 as Catalyst for the Polymerization of Monomers Methyl Acrylate and Norbornene This comparative example utilizes the catalyst preparative method and catalyst precursor described in Example 8 of U.S. Pat. No. 6,303,724 i.e., combining allylpalladium chloride dimer with tricyclohexylphosphine first and then adding lithium tetrakis(pentafluorophenyl)borate etherate. The polymeric mixture produced infra utilizing that catalyst precursor is a mixture of two components, as clearly elucidated by the more in-depth analyses used in this Comparative Example 4.

A 5 mL vial was charged with allylpalladium chloride dimer (9.6 mg, 0.026 mmol) and tricyclohexylphosphine (14.6 mg, 0.052 mmol). $CH_2Cl_2$ (pre-cooled at $-35°$ C., 2 mL) was added and the mixture was gently swirled to form a clear yellow solution. A solution of lithium tetrakis(pentafluorophenyl)borate etherate ($CH_2Cl_2$, 1 mL, 43.4 mg/mL) was added to form a yellow solution, which was not transparent but no visible particles could be observed. Additional $CH_2Cl_2$ (1 mL) was added. The catalyst solution was added to a serum bottle containing toluene (15 mL), norbornene (2.03 g, 21.6 mmol, pre-dissolved in toluene, 86 wt %) and methyl acrylate (1.0 g, 12 mmol) to form a yellow solution, which was stirred at 50° C. 17 hours later, the reaction mixture was poured into methanol (200 mL) to form a pale yellow slurry in a yellow solution immediately. The suspension was filtered. The solid was collected and dried under vacuum at 60° C. overnight to yield a yellow solid (0.129 g). $^1$H NMR analysis revealed that the product had an overall molar ratio of 64 (norbornene): 36 (methyl acrylate). GPC experiment exhibited a bimodal pattern: Peak 1, Mw 24800, Mn 19300, Mw/Mn 1.28; Peak 2, Mw 1600, Mn 1100, Mw/Mn 1.45.

EXAMPLE 1

Preparation of a Catalytic Composition and Use of that Catalytic Composition to Prepare Copolymers of Methyl Acrylate and Norbornene, According to the Method of the Present Invention In contrast to Comparative Example 4, this experiment shows that a key to preparing a copolymer of methyl acrylate and norbornene is to first combine a full-(metal pair) precursor complex, here a dimer wherein both $M^1$ and $M^2$ are palladium, and the activator component (Li salt in this case), and then add the phosphine ligand to the activated palladium species.

A 5 mL vial was charged with allylpalladium chloride dimer (9.6 mg, 0.026 mmol) and lithium tetrakis(pentafluorophenyl)borate etherate (43.4 mg, 0.052 mmol). $CH_2Cl_2$ (pre-cooled at $-35°$ C., 2 mL) was added and the mixture was gently swirled to form a pale yellow slurry. A solution of tricyclohexylphosphine ($CH_2Cl_2$, 1 mL, 14.6 mg/mL) was added to form a pale yellow slurry. Additional $CH_2Cl_2$ (1 mL) was added. The catalytic composition solution was added to a serum bottle containing toluene (15 mL), norbornene (2.03 g, 21.6 mmol, pre-dissolved in toluene, 86 wt %) and methyl acrylate (1.0 g, 12 mmol) to form a pale yellow solution, which was stirred in a 50° C. water bath. 17 hours later, the reaction mixture was poured into methanol (200 mL) to form a pale yellow slurry in a yellow solution immediately. The suspension was filtered. The solid was collected and dried under vacuum at 60° C. overnight to yield a pale yellow solid (0.716 g). $^1$H NMR analysis revealed that the product had a molar ratio of 84 (norbornene): 16 (methyl acrylate). GPC analysis revealed a unimodal pattern: Mw 11700, Mn 6100, Mw/Mn 1.92.

EXAMPLE 2

Preparation of a Catalytic Composition and Use of that Catalytic Composition to Prepare Copolymers of Methyl Acrylate and Norbornene, According to the Method of the Present Invention In contrast to Comparative Example 4, this experiment showed that a key to preparing a copolymer of methyl acrylate and norbornene is to combine a full-(metal pair) precursor complex, here a dimer wherein both $M^1$ and $M^2$ are palladium, and the activator component (Li salt in this case) first and then add the phosphine ligand to the activated palladium species, that is, using the method of catalytic composition preparation of the present invention. The experiment followed the procedure described in Example 1 supra with variation in the amount of monomers and the reaction time.

A 5 mL vial was charged with allylpalladium chloride dimer (9.6 mg, 0.026 mmol) and lithium tetrakis(pentafluorophenyl)borate etherate (43.4 mg, 0.052 mmol). $CH_2Cl_2$ (pre-cooled at $-35°$ C., 1 mL) was added and the mixture was gently swirled to form a pale yellow solution with fine particles. A solution of tricyclohexylphosphine ($CH_2Cl_2$, 1 mL, 14.6 mg/mL) was added to form a pale yellow slurry. The catalytic composition solution was added to a serum bottle containing toluene (10 mL), norbornene (2.26 g, 24 mmol, pre-dissolved in toluene, 86 wt %) and methyl acrylate (2.0 g, 24 mmol) to form a pale yellow solution, which was stirred at 50° C. 1 hour later, the reaction mixture was poured into methanol (150 mL) to form a pale yellow slurry in a yellow solution immediately. The solid was isolated by filtration and dried under vacuum at 60° C. overnight to yield a yellow solid (0.281 g). $^1$H NMR experiment showed that the product had a molar ratio of 19 (norbornene): 81 (methyl acrylate). GPC analysis revealed a unimodal pattern: Mw 57500, Mn 41000, Mw/Mn 1.4.

EXAMPLE 3

Preparation of a Catalytic Composition and Use of that Catalyst Composition to Prepare a Copolymer of Methyl Acrylate and Norbornene, According to the Method of the Present Invention This experiment was similar to Examples 1 and 2 (vide supra) with differences in monomer ratio and reaction time. It was shown again that preparation of a true copolymer of norbornene and methyl acrylate can be achieved by the methods of catalytic composition generation and use in accordance with of the present invention.

A 2 mL vial was charged with allylpalladium chloride dimer (9.6 mg, 0.026 mmol) and lithium tetrakis(pentafluorophenyl)borate etherate (43.4 mg, 0.052 mmol). $CH_2Cl_2$ (pre-cooled at $-35°$ C., 1 mL) was added and the mixture was gently swirled to form a pale yellow solution with fine particles. A solution of tricyclohexylphosphine ($CH_2Cl_2$, 1 mL, 14.6 mg/mL) was added to form a brownish yellow slurry instantaneously. The catalytic composition solution was added to a serum bottle containing toluene (10 mL), norbornene (1.70 g, 18 mmol, pre-dissolved in toluene, 86 wt %) and methyl acrylate (1.0 g, 12 mmol) to form a yellow solution, which was stirred at 50° C. 19 hours later, the reaction mixture was poured into fresh methanol (200 mL) to form a yellow slurry instantaneously. The solid was isolated by filtration and dried under vacuum at 60° C. overnight to yield a light yellow solid (0.778 g). $^1$H NMR analysis showed that the product had a molar ratio of 67 (norbornene): 33 (methyl acrylate). GPC analysis revealed a unimodal pattern: Mw 15000, Mn 8500, Mw/Mn 1.76.

EXAMPLE 4

Preparation of a Catalytic Composition and Use of that Catalytic Composition to a Prepare a Copolymer of Norbornene and Tert-butyl Acrylate, According to the Method of the Present Invention In this experiment, a copolymer of norbornene and tert-butyl acrylate was prepared by using the catalytic composition composition generated according to the method of the present invention. It was shown that preparation of a copolymer of norbornene and tert-butyl acrylate can be achieved by the methods of catalytic composition generation and use of the present invention.

A 2 mL vial was charged with allylpalladium chloride dimer (19.2 mg, 0.052 mmol) and lithium tetrakis(pentafluorophenyl)borate etherate (86.8 mg, 0.104 mmol). CH$_2$Cl$_2$ (pre-cooled at −35° C., 1 mL) was added and the mixture was gently swirled to form a pale yellow solution with fine particles. A solution of tricyclohexylphosphine (CH$_2$Cl$_2$, 1 mL, 29.2 mg/mL) was added to form a brownish yellow slurry instantaneously. The catalytic composition solution was added to a serum bottle containing toluene (10 mL), norbornene (3.40 g, 36 mmol, pre-dissolved in toluene, 86 wt %) and tert-butyl acrylate (3.08 g, 24 mmol) to form a yellow solution, which was stirred at 50° C. 3 hours later, the reaction mixture was poured into fresh methanol (200 mL) to form a yellow slurry instantaneously. The solid was isolated and dried under vacuum at 60° C. overnight to yield a yellow solid (0.938 g). $^{13}$C NMR analysis revealed that the product had a molar ratio of 28 (norbornene): 72 (tert-butyl acrylate). GPC and LC-NMR analyses revealed a unimodal pattern: Mw 57500, Mn 42000, Mw/Mn 1.37.

EXAMPLE 5

Preparation of a Catalytic Composition and Use of that Catalytic Composition to Prepare a Terpolymer of an Acrylate, Norbornene, and a Substituted Norbornene, According to the Method of the Present Invention In this experiment, a terpolymer of norbornene, tert-butyl acrylate and 5-R-norbornene, [R=—CH$_2$C(CF$_3$)$_2$(OH)], was prepared by using the catalytic composition generated according to the method of the present invention. It was shown that preparation of a terpolymer of norbornene, tert-butyl acrylate, and a third monomer (in this case 5-R-norbornene, [R=—CH$_2$C(CF$_3$)$_2$(OH)]), can be achieved by the methods of catalytic composition generation and use of the present invention.

A 2 mL vial was charged with allylpalladium chloride dimer (19.2 mg, 0.052 mmol) and lithium tetrakis(pentafluorophenyl)borate etherate (86.8 mg, 0.104 mmol). CH$_2$Cl$_2$ (pre-cooled at −35° C.,1 mL) was added and the mixture was gently swirled to form a pale yellow solution with fine particles. A solution of tricyclohexylphosphine (CH$_2$Cl$_2$, 1 mL, 29.2 mg/mL) was added to form a brownish yellow slurry. The catalytic composition solution was added to a serum bottle containing toluene (10 mL), norbornene (3.40 g, 36 mmol, pre-dissolved in toluene, 86 wt %), tert-butyl acrylate (3.08 g, 24 mmol) and 5-R-norbornene (R=—CH$_2$C(CF$_3$)$_2$(OH), 3.28 g, 12 mmol) to form a yellow solution, which was stirred at 50° C. 3 hours later, the reaction mixture was poured into fresh methanol (200 mL) to form a yellow slurry. The solid was isolated by filtration and dried under vacuum at 60° C. overnight to yield a yellow solid (0.692 g). $^{13}$C NMR analysis showed that the product had a molar ratio of 43 (norbornene): 55 (tert-butyl acrylate): 2 (5-R-norbornene). GPC experiment exhibited a major peak at Mw 48500, Mn 35500, Mw/Mn 1.37 and a minor peak (less than 10 area %, based on the total area of both peaks) at Mw 2000, Mn 1300, Mw/Mn 1.54.

EXAMPLE 6

Preparation of a Catalytic Composition and Use of that Catalytic Composition to Prepare a Terpolymer of an Acrylate, Norbornene, and a Substituted Norbornene, According to the Method of the Present Invention In this experiment, a terpolymer of norbornene, tert-butyl acrylate and 5-R-norbornene, [R=—CH$_2$C(CF$_3$)$_2$(OH)], was prepared by using a cationic metal-pair complex generated according to the method of the present invention. A silver salt, was used to replace the lithium salt. It was shown that preparation of a terpolymer of norbornene, tert-butyl acrylate, and a third monomer (in this case 5-R-norbornene, [R=—CH$_2$C(CF$_3$)$_2$(OH)]), can be achieved by the methods of catalytic composition generation and use of the present invention.

A 10 mL vial was charged with allylpalladium chloride dimer (40.0 mg, 0.109 mmol). CH$_2$Cl$_2$ (1 mL) was added to yield a clear yellow solution. A 5 mL vial was charged with tricyclohexylphosphine (61.2 mg, 0.218 mmol). CH$_2$Cl$_2$ (1 mL) was added to yield a clear colorless solution. A 1 mL vial was charged with silver hexafluorophosphate (27.6 mg, 0.109 mmol). The silver hexafluorophosphate solution was added to the solution of allylpalladium chloride dimer, which was swirled for ca. 1 min to form a yellow/white slurry. The solution of tricyclohexylphosphine was added to form a brownish yellow solution with white slurry. Additional CH$_2$Cl$_2$ (1 mL) was added. The catalytic composition solution (1 mL) was added to a serum bottle containing toluene (10 mL), norbornene (2.26 g, 24 mmol, pre-dissolved in toluene, 86 wt %), tert-butyl acrylate (3.08 g, 24 mmol) and 5-R-norbornene (R=—CH$_2$C(CF$_3$)$_2$(OH), 1.64 g, 6 mmol) to form a yellow solution, which was stirred at 50° C. 3.5 hours later, the reaction mixture was quenched with methanol (25 mL) to yield a yellow slurry. The solid was isolated by filtration and dried under vacuum at 60° C. deg C overnight to yield a yellow solid (1.729 g). $^{13}$C NMR analysis revealed that the product had a molar ratio of 87 (norbornene): 9 (tert-butyl acrylate): 4 (5-R-norbornene). GPC analysis revealed a unimodal pattern: Mw 66000, Mn 47000, Mw/Mn 1.40.

EXAMPLE 7

Preparation of a Catalytic Composition and Use of that Catalytic Composition to Prepare a Homopolymer of Norbornene, According to the Method of the Present Invention In this experiment, a homopolymer of norbornene was prepared using a procedure similar to that described in Example 6. The polymer was shown by NMR spectroscopy to have a microstructure different from that of the homopolymer poly(norbornene) made using palladium or nickel catalytics other than those of the present invention (see Goodall, B. L. *Cycloaliphatic Polymers via Late Transition Metal Catalysts* in *Late Transition Metal Polymerization Catalysis*; Rieger, B.; Baugh, L. S.; Kacker S.; Striegler, S., Eds.; WILEY-VCH: Weinheim, 2003, pp 101–192).

A 10 mL vial was charged with allylpalladium chloride dimer (20.0 mg, 0.0546 mmol) and silver hexafluorophosphate (13.8 mg, 0.0546 mmol). $CH_2Cl_2$ (1 mL) was added to form a yellow slurry instantaneously. A 5 mL vial was charged with tricyclohexylphosphine (30.6 mg, 0.109 mmol). $CH_2Cl_2$ (1 mL) was added to form a clear colorless solution, which was added to the solution of allylpalladium chloride dimer and silver hexafluorophosphate. The mixture was swirled for ca. 1 min to form a pale yellow slurry. The catalytic composition solution (1 mL) was added to a 50 mL serum bottle containing toluene (20 mL) and norbornene (1.13 g, 12 mmol, pre-dissolved in toluene, 86 wt %), which was then stirred at 50° C. 2 hours later, the reaction mixture was quenched with methanol (50 mL) to yield an off-white slurry. The solid was isolated by filtration and dried under vacuum at 60° C. overnight to yield an off-white solid (0.900 g). $^1H$ and $^{13}C$ NMR experiments showed that this polymer had a different microstructure from homo poly(norbornene) made by other palladium or nickel catalysts that are not the catalytic composition of the present invention. The product was dissolved in $CHCl_3$ and GPC analysis revealed a unimodal pattern: Mw 39000, Mn 32000, Mw/Mn 1.22.

EXAMPLE 8

Preparation of a Catalytic Composition Using 1.0 Equivalent of Silver Salt, Based on Allylpalladium Chloride Dimer, and Utilizing that Catalytic Composition to Prepare a Copolymer of Norbornene and Tert-butyl Acrylate, According to the Method of the Present Invention In this experiment, a copolymer of norbornene and tert-butyl acrylate was prepared using the a procedure similar to that described in Example 6.

Vial #1 was charged with allylpalladium chloride dimer (20.0 mg, 0.0546 mmol). $CH_2Cl_2$ (1 mL) was added to form a clear yellow solution. Vial #2 was charged with tricyclohexylphosphine (30.6 mg, 0.109 mmol). $CH_2Cl_2$ was added to form a clear colorless solution. Vial #3 was charged with silver hexafluorophosphate (13.8 mg, 0.0546 mmol). $CH_2Cl_2$ was added to form a clear colorless solution. The solution of silver hexafluorophosphate was added to the solution of allylpalladium chloride dimer. The mixture was swirled for ca. 1 min at room temperature to form a yellow/white slurry. The solution of tricyclohexylphosphine was added to form a white slurry in a pale yellow solution. The catalytic composition in $CH_2Cl_2$ (3 mL) was added to a 100 mL serum bottle containing toluene (30 mL), norbornene (3.39 g, 36 mmol, pre-dissolved in toluene, 86 wt %) and tert-butyl acrylate (4.61 g, 36 mmol) to form a yellow solution w/a small amount of solids, which was stirred at 50° C. 3 hours later, the reaction mixture was quenched with methanol (ca. 450 mL) to form a yellow suspension. The solid was isolated by filtration and dried under vacuum at 60° C. overnight to yield a pale yellow solid (2.402 g). $^{13}C$ NMR analysis revealed that the product had a molar ratio of 84 (norbornene): 16 (tert-butyl acrylate). GPC experiment exhibited a unimodal pattern: Mw 56000, Mn 41000, Mw/Mn 1.37.

EXAMPLE 9

Preparation of a Catalytic Composition Using 0.5 Equivalents of Silver Salt, Based on (allyl)palladium(tricyclohexylphosphine)chloride, and Utilizing that Catalytic Composition to Prepare a Copolymer of Norbornene and Methyl Acrylate, According to the Method of the Present Invention In this experiment, a copolymer of norbornene and methyl acrylate was prepared using a procedure in which the cationic metal-pair complex was generated by combining (allyl)palladium-(tricyclohexylphosphine)chloride with silver hexafluorophosphate (0.5 equiv).

Vial #1 was charged with (allyl)palladium(tricyclohexylphosphine)-chloride (10 mg, 0.0216 mmol). $CH_2Cl_2$ (1 mL) was added to form a clear pale yellow solution. Vial #2 was charged with silver hexafluorophosphate (2.7 mg, 0.0108 mmol). $CH_2Cl_2$ (2 mL) was added to form a clear colorless solution. The solution of silver hexafluorophosphate was added to the solution of (allyl)palladium(methyl)chloride. The mixture was swirled for ca. 1 min at room temperature to form a pale yellow slurry. The catalytic composition in $CH_2Cl_2$ (1 mL) was added to a 100 mL serum bottle containing toluene (10 mL), norbornene (1.13 g, 12 mmol, pre-dissolved in toluene, 86 wt %) and methyl acrylate (1.03 g, 12 mmol) to form a pale yellow solution, which was then stirred at 50° C. 3 hours later, the reaction mixture was quenched with methanol (200 mL) to yield a lump of off-white solid in a colorless solution. The solid was isolated by filtration and dried under vacuum at 60° C. overnight to yield a white solid (0.692 g). $^1H$ NMR experiment showed that the product had a molar ratio of 85 (norbornene): 15 (methyl acrylate). GPC and LC analyses revealed a unimodal pattern: Mw 121000, Mn 91000, Mw/Mn 1.33.

COMPARATIVE EXAMPLE 5

Preparation of a Complex Using 1.0 Equivalent of Silver Salt, Based on (allyl)palladium(tricyclohexylphosphine)chloride, and Utilizing the Complex to Polymerize Norbornene and Methyl Acrylate In contrast to Example 9, this method of combining (allyl)palladium(tricyclohexylphosphine)chloride with silver hexafluorophosphate (1.0 equiv. instead of the 0.5 of Example 9) did not generate a catalyst that would produce a copolymer of norbornene and tert-butyl acrylate.

A 2 mL vial was charged with (allyl)palladium-(tricyclohexylphosphine)chloride (5.0 mg, 0.011 mmol) and silver hexafluorophosphate (2.7 mg, 0.011 mmol). $CH_2Cl_2$ (1 mL) was added and the mixture was gently swirled to form a pale yellow solution with fine white particles. The catalyst solution was added to a serum bottle containing toluene (10 mL), norbornene (3.40 g, 36 mmol, pre-dissolved in toluene, 86 wt %) and tert-butyl acrylate (3.08 g, 24 mmol), which was stirred at 22 deg. 3.5 hours later, the reaction mixture was quenched with methanol (100 mL) to form a yellow slurry. The solid was isolated by filtration and dried under vacuum at 60° C. overnight to yield a yellow solid (1.618 g). IR analysis revealed only a tiny carbonyl peak from tert-butyl acrylate. $^1$H, PFG and HETCOR NMR analyses revealed that the polymer was homo poly (norbornene) and tert-butyl acrylate appeared to be residual monomer instead of part of the polymer.

EXAMPLE 10

Preparation of a Copolymer of Norbornene and Methyl Methacrylate by the Polymerization of Norbornene and Methyl Methacrylate Catalyzed by a Catalytic Composition In this experiment, a copolymer of norbornene and methyl methacrylate was prepared using a procedure in which a cationic metal-pair complex was first generated by combining (allyl)palladium chloride dimer with silver hexafluorophosphate (0.5 equiv, based on the two palladium atoms of the dimer) and then adding two equivalents of tricyclohexylphosphine.

Vial #1 was charged with allylpalladium chloride dimer (10.0 mg, 0.0273 mmol). CH$_2$Cl$_2$ (2 mL) was added to form a clear pale yellow solution. Vial #2 was charged with silver hexafluorophosphate (6.9 mg, 0.0273 mmol). CH$_2$Cl$_2$ (2 mL) was added to form a clear colorless solution. Vial #3 was charged with tricyclohexylphosphine (15.3 mg, 0.0546 mmol). CH$_2$Cl$_2$ (2 mL) was added to form a clear colorless solution. The solution of silver hexafluorophosphate was added to the solution of allylpalladium chloride dimer, followed by swirling for ca. 1 minute at room temp to form a yellow-white slurry. To this mixture was added the solution of tricyclohexylphosphine to form a white slurry in a pale yellow solution. The catalytic composition in CH$_2$Cl$_2$ (1 mL) was added to a 100-mL serum bottle containing toluene (10 mL), norbornene (1.13 g, 12 mmol, pre-dissolved in toluene, 86 wt %) and methyl methacrylate (1.20 g, 12 mmol) to form a clear pale yellow solution, which was stirred at 50° C. 5 hours later, the reaction mixture became a yellow slurry in a yellow solution and was quenched with methanol (150 mL) to form a white slurry in a pale yellow solution. The mixture was filtered. The solid was collected and dried under vacuum at 70° C. overnight to yield a white solid (1.313 g). $^1$H NMR experiment revealed that the product had a molar ratio of 84 (norbornene): 16 (methyl methacrylate). GPC experiment exhibited a unimodal pattern: Mw 130000, Mn 100000, Mw/Mn 1.30.

EXAMPLE 11

Preparation of the Cationic Metal-pair Complex of the Present Invention Wherein Both First Metal Atom and Second Metal Atom are Palladium, Both First Ligand and Second Ligand are Tricyclohexylphosphine, both First Hydrocarbyl Radical and Second Hydrocarbyl Radical are Allyl, Bridging Moiety is Chloride, and WCA— is Hexafluorophosphate In the preparative procedures of Examples 11 and 12, all manipulations were carried out in a nitrogen containing glove box with less than 5 ppm oxygen and less than 2 ppm water in the atmosphere. Pentane was dried over 3 Å molecular sieves and degassed with nitrogen prior to use. Dichloromethane was purified by passing it through a column of alumina under nitrogen. Celite was dried under vacuum (<50 mtorr) at 125° C. for 2 hours.

Allylpalladium chloride dimer (0.300 g, 0.819 mmol) was dissolved in 5 mL of dichloromethane to yield a yellow solution. Separately, silver hexafluorophosphate (0.208 g, 0.819 mmol) was dissolved in 5 mL of dichloromethane to give a clear solution. The solution of the silver salt was added to the palladium containing solution and a precipitate immediately formed. The yellow slurry was allowed to stir in the dry box for 15 minutes. Meanwhile, tricyclohexylphosphine ("PCy3", 0.459 g, 1.638 mmol) was dissolved in dichloromethane (5 mL). The clear phosphine solution was added to the reaction mixture which remained yellow. After allowing the reaction mixture to stir for an additional 15 minutes, the slurry was vacuum filtered through Celite into a Schlenk flask. The pale yellow filtrate was concentrated to dryness on a vacuum line to give a lemon yellow powder which was collected and stored in the dry box. X-ray quality crystals were grown by allowing a layer of pentane to diffuse into a dichloromethane solution of the product at room temperature. The following sets of NMR peaks were consistent with the desired structure. 1H NMR (d6-acetone, 500 MHz): δ 1.30–2.28 (m, 66H, Cy), 3.03 (br s, 2H, allyl), 3.79 (br s, 2H, allyl), 3.89 (dd, 2H, allyl), 4.82 (dd, 2H, allyl), 5.83 (m, 2H, allyl) ppm. 31P{1H, 13C} NMR: δ-140 (septet, PF6—), 42 (s, PCy) ppm.

EXAMPLE 12

Preparation of the Cationic Metal-pair Complex of the Present Invention Wherein Both First and Second Metal Atoms are Palladium, Both First and Second Ligand are Absent (i.e., Subscript a=b=0), Both First and Second Hydrocarbyl Radical are Allyl, WCA— is Hexafluoroantimonate and Bridging Moiety is 1,3-bis(3,5-di-tert-butylpyrazolyl-1-carbonyl)benzene and Chloride Allylpalladium chloride dimer (0.100 g, 0.273 mmol) was dissolved in 5 mL of dichloromethane to yield a yellow solution. Separately, silver hexafluoroantimonate (0.0939 g, 0.273 mmol) was dissolved in 5 mL of dichloromethane to give a clear solution. The solution of the silver salt was added to the palladium containing solution and a precipitate immediately formed. The yellow slurry was allowed to stir in the dry box for 15 minutes. Meanwhile, 1,3-Bis(3,5-di-tert-butylpyrazolyl-1-carbonyl)benzene (0.134 g, 0.273 mmol) was dissolved in dichloromethane (5 mL). The resulting clear solution was added to the reaction mixture which remained yellow. After allowing the reaction mixture to stir for an additional 15 minutes, the slurry was vacuum filtered through Celite into a Schlenk flask. The yellow filtrate was concentrated to dryness on a vacuum line to give a pale yellow powder which was collected and stored in the dry box. X-ray quality crystals were grown from d-chloroform at −35° C. The following set of NMR peaks was consistent with the desired structure. 1H NMR (CDCl3, 500 MHz): δ 1.30 (broad, 9H, t-butyl), 1.41 (broad, 9H, t-butyl), 2.96 (broad s, 4H, allyl), 3.94 (broad s, 4H, allyl), 5.47 (broad s, 2H, allyl), 6.31 (s, 2H, pyrazolyl), 8–8.8 (broad, 4H, aryl) ppm. 1,3-Bis(3,5-di-tert-butylpyrazolyl-1-carbonyl)benzene was prepared according to the literature method of Guzei, I. A., et al., S. F. Dalton Trans., 2003, 715–722.

EXAMPLE 13

Preparation of a Cationic Metal-pair Complex by Sequential Addition of a Solution of 1 Equivalent of Silver Hexafluoroantimonate and a Solution of 2 Equivalents of Tricyclohexylphosphine to a Solution of Allylpalladium Chloride Dimer, and Utilizing That Catalytic Composition to Prepare a Homopolymer of Norbornene of Very High Molecular Weight and Narrow MWD Polydispersity, According to the Method of the Present Invention Vial #1 was charged with allylpalladium chloride dimer (40.0 mg, 0.109 mmol). $CH_2Cl_2$ (1 mL) was added to form a clear yellow solution. Vial #2 was charged with the activator silver hexafluoroantimonate (37.6 mg, 0.109 mmol). $CH_2Cl_2$ (1 mL) was added to form a clear colorless solution. Vial #3 was charged with tricyclohexylphosphine (61.2 mg, 0.218 mmol). $CH_2Cl_2$ (1 mL) was added to form a clear colorless solution. The solution of silver hexafluoroantimonate was added to the solution of allylpalladium chloride dimer. The mixture was swirled for ca. 1 min at room temperature to form a white slurry in a yellow solution. The solution of tricyclohexylphosphine was then added to the mixture of allylpalladium chloride dimer and silver hexafluoroantimonate to form a brown slurry in a yellow solution. Fresh $CH_2Cl_2$ (5 mL) was added (Catalyst Solution A, 8 mL). 0.2 mL of the supernatant of Catalyst Solution A was transferred to another clean vial using syringe, which was diluted to 2 mL with $CH_2Cl_2$. 0.2 mL of the diluted solution was again transferred to a third clean vial, which was diluted to 2 mL with $CH_2Cl_2$. A solution containing norbornene (12 mmol, pre-dissolved in toluene, 86 wt %) and additional toluene (10 mL) was added to the diluted catalyst solution (1 mL, containing 1.25% of the catalytic composition in Catalyst Solution A) to yield a clear colorless solution. The reaction mixture was allowed to stay at room temperature for ca. 5 min before the serum bottle was sealed and transferred out of the glove box and stirred in a 50° C. water bath in a fume hood. 21.5 hours later, the reaction mixture became a viscous pale yellow slurry, which was quenched with methanol (300 mL) to yield a white slurry in a colorless solution. The solid was isolated by filtration and dried under vacuum at 60° C. overnight to yield a while solid (0.966 g, 85%). GPC experiment exhibited a unimodal pattern: Mw 1435000, Mn 1040000, Mw/Mn 1.38.

EXAMPLE 14

Utilizing a Cationic Metal-pair Complex to Prepare a Homopolymer of Norbornene of Very Narrow Polydispersity in the Presence of a Large Amount of Water, According to the Method of the Present Invention A glass vial was charged with the catalytic composition of Example 11 (10 mg, 0.0089 mmol). $CH_2Cl_2$ (2 mL) was added to form a clear pale yellow solution. The catalyst solution (1 mL) was added to a 100-mL serum bottle containing norbornene (12 mmol, pre-dissolved in toluene, 86 wt %) and additional toluene (10 mL) to form a clear pale yellow solution. The reaction mixture was sealed with a septum and moved to a fume hood. $H_2O$ (5 mL, deoxygenated by purging with nitrogen for 1 hour) was added to the reaction mixture to form two distinctive phases. The reaction mixture was stirred at 50° C. (water bath) for 2 hours. 2 hours later, the reaction mixture was cooled to room temperature and stirring was terminated; then it became a yellow solution with a white liquid layer at the bottom. The reaction mixture was poured into methanol (300 mL) to form a pale yellow slurry in a nearly colorless solution, which was filtered to yield a pale yellow solid and a nearly colorless solution. The solid was collected and dried under vacuum at 65° C. for 2 hours to yield a pale yellow solid (113 mg, 10%). $^1H$ NMR experiment revealed that the product was a homopolymer of norbornene. GPC experiment exhibited a unimodal pattern: Mw 39000, Mn 37000, Mw/Mn 1.05.

EXAMPLE 15

Utilizing a Cationic Metal-pair Complex to Prepare a Copolymer of Norbornene and Methyl Acrylate of Very Narrow Polydispersity in the Presence of a Large Amount of Water, According to the Method of the Present Invention A glass vial was charged with the catalytic composition of Example 11 (10 mg, 0.0089 mmol). $CH_2Cl_2$ (2 mL) was added to form a clear pale yellow solution. The catalyst solution (1 mL) was added to a 100-mL serum bottle containing norbornene (12 mmol, pre-dissolved in toluene, 86 wt %) and additional toluene (10 mL) to form a clear pale yellow solution. The reaction mixture was sealed with a septum and moved to a fume hood. $H_2O$ (5 mL, deoxygenated by purging with nitrogen for 1 hour) was added to the reaction mixture to form two distinctive phases. The reaction mixture was stirred at 50° C. (water bath) for 2 hours. 2 hours later, the reaction mixture was cooled to room temperature and stirring was terminated; then it became a yellow solution with a white liquid layer at the bottom. The reaction mixture was poured into methanol (300 mL) to form a pale yellow slurry in a nearly colorless solution, which was filtered to yield a pale yellow solid and a nearly colorless solution. The solid was collected and dried under vacuum at 65° C. for 2 hours to yield a yellow solid (234 mg, 10%). $^1H$ NMR experiment revealed that the product had a molar ratio of 51 (norbornene): 49 (methyl acrylate). GPC experiment exhibited a unimodal pattern: Mw 40000, Mn 33000, Mw/Mn 1.21.

EXAMPLE 16

Utilizing a Cationic Metal-pair Complex to Prepare a Copolymer of Norbornene and 5-R-Norbornene (R=$Si(OCH_2CH_3)_3$, triethoxysilyl), According to the Method of the Present Invention A glass vial A was charged with the catalytic composition of Example 11 (7.0 mg, 0.0062 mmol). $CH_2Cl_2$ (4 mL) was added to form a clear pale yellow solution. The mixture was swirled at room temperature for 0.5 min, which was labeled Catalyst Solution A. Catalyst Solution A was stored at −35° C. About 5 min later, Catalyst Solution A (1 mL) was added to a reaction mixture in a 100-mL serum bottle containing norbornene (24 mmol, pre-dissolved in toluene, 79%), 5-R-norbornene and toluene (10 mL) to form a clear pale yellow solution. The reaction mixture was sealed with a rubber septum and transferred to a fume hood. 10 min after the catalytic composition was added, the reaction mixture was stirred at 50° C. using a water bath in the fume hood. Half an hour later, the reaction mixture remained a clear pale yellow solution. 3 hours later, the reaction mixture was quenched with methanol (ca. 150 mL) to form a pale yellow polymer aggregate in a colorless solution. The solution was decanted and the remaining polymer was rinsed with methanol (100 mL) 4 times. The product was dried under vacuum at room temperature overnight to yield a white solid (1.61 g, 19%). $^1$H NMR experiment revealed that the product had a molar ratio of 42 (norbornene): 58 (5-R-norbornene). GPC experiment exhibited a unimodal pattern: Mw 500000, Mn 400000, Mw/Mn 1.3. TGA experiment showed weight losses during various heating stages under nitrogen: 4.079% (300° C., 60 min), 3.830% (350° C., 60 min), 86.99% (425°C.).

EXAMPLE 17

Utilizing a Cationic Metal-pair Complex to Prepare a Homopolymer of Low Molecular Weight by Employing a Chain Transfer Agent, According to the Method of the Present Invention A glass vial A was charged with the catalytic composition of Example 24 (vide infra) (5.3 mg, 0.0028 mmol). $CH_2Cl_2$ (2.5 mL) was added to form a clear colorless solution. The mixture was swirled at room temperature for 0.5 min, which was labeled Catalyst Solution A and stored at ambient temperature for about 1 min. Catalyst Solution A (0.5 mL) was added to a 100-mL serum bottle containing norbornene (6 mmol, pre-dissolved in toluene, 79 wt %), 1-octene (60 mmol) and additional toluene (15 mL) to form a clear colorless solution at ambient temperature. The serum bottle was sealed with a rubber septum and transferred to a fume hood. 5 min after the catalytic composition was added, the reaction mixtures were stirred at 50° C. using a water bath in the fume hood. 20.5 hrs later, the reaction mixture remained a clear colorless solution, which was quenched with methanol (ca. 100 mL) to form a white slurry in a colorless solution. The solid was isolated by filtration and dried under vacuum at 65° C. overnight to yield a white solid (463 mg, 82%). The product was soluble in deuterated chloroform and $^1$H NMR experiment revealed that it was a homopolymer of norbornene with a vinyl end group. GPC experiment exhibited a unimodal pattern: Mw 3000, Mn 1600, Mw/Mn 1.9.

EXAMPLE 18

Utilizing a Catalytic Cationic Metal-pair Complex to Prepare a Copolymer of Norbornene and 5-R-norbornene (R=$CH_2C(CF_3)_2$(OH)), According to the Method of the Present Invention Glass vial A was charged with allylpalladium chloride dimer (19.2 mg, 0.052 mmol). $C_6H_6Cl$ (1 mL) was added to form a nearly colorless solution with yellow solid. Glass vial B was charged with lithium tetrakis(pentafluorophenyl)borate etherate (86.8 mg, 0.104 mmol). $C_6H_5Cl$ (1 mL) was added to form a brownish yellow solution. Glass vial C was charged with tri(2,4-di-tert-butylphenyl)phosphite (67.3 mg, 0.104 mmol). $C_6H_5Cl$ (1 mL) was added to form a clear colorless solution. The solution in glass vial B was mixed with that in glass vial A to form a clear brownish yellow solution, which was stored in glass vial A. Glass vial B was rinsed with $C_6H_5Cl$ (1 mL) and the solution was added to glass vial A. The mixture was swirled at room temperature for 1 min. The solution in glass vial C was added to glass vial A to form a clear brownish yellow solution. Glass vial C was rinsed with $C_6H_5Cl$ (1 mL) and the solution was added to glass vial A. The mixture was swirled at room temperature, which was labeled Catalyst Solution A. A 15-mL serum bottle was charged with norbornene (3 mmol, pre-dissolved in toluene) and chlorobenzene (2 mL) to form a clear colorless solution, which was sealed with rubber septum and transferred to a fume hood. 5-R-norbornene (3 mmol, used as received) was injected into the bottle by a syringe. Catalyst Solution A (0.5 mL) was added to the monomer solution to form a clear pale yellow solution. 1 min after the catalyst was added, the reaction mixture became an orange yellow gel, which was washed with methanol (ca. 100 mL), isolated by filtration and dried under vacuum overnight.

EXAMPLE 19

Utilizing a Cationic Metal-pair Complex to Prepare a Homopolymer of 5-R-norbornene (R=$Cl_2C(CF_3)_2$(OH)), According to the Method of the Present Ivention Glass vial A was charged with allylpalladium chloride dimer (19.2 mg, 0.052 mmol). $C_6H_5Cl$ (1 mL) was added to form a nearly colorless solution with yellow solid. Glass vial B was charged with lithium tetrakis(pentafluorophenyl)borate etherate (86.8 mg, 0.104 mmol). $C_6H_5Cl$ (1 mL) was added to form a brownish yellow solution. Glass vial C was charged with tri(2,4-di-tert-butylphenyl)phosphite (67.3 mg, 0.104 mmol). $C_6H_5Cl$ (1 mL) was added to form a clear colorless solution. The solution in glass vial B was mixed with that in glass vial A to form a clear brownish yellow solution, which was stored in glass vial A. Glass vial B was rinsed with $C_6H_5Cl$ (1 mL) and the solution was added to glass vial A. The mixture was swirled at room temperature for 1 min. The solution in glass vial C was added to glass vial A to form a clear brownish yellow solution. Glass vial C was rinsed with $C_6H_5Cl$ (1 mL) and the solution was added to glass vial A. The mixture was swirled at room temperature, which was labeled Catalyst Solution A. A 15-mL serum bottle was charged with chlorobenzene (2 mL), which was sealed with rubber septum and transferred to a fume hood. 5-R-norbornene (3 mmol, used as received) was injected into the bottle by a syringe. Catalyst Solution A (0.5 mL) was added to the monomer solution to form a clear pale yellow solution. The reaction mixture was heated at 90° C. for 15 min and it became a yellow solid, which was washed with methanol (ca. 100 mL), isolated by filtration and dried under vacuum overnight.

Unless otherwise noted in Examples 20–30, all manipulations were carried out in a nitrogen containing glove box with less than 5 ppm $O_2$ and less than 2 ppm $H_2O$ in the atmosphere. Pentane, hexanes, diethyl ether, and tetrahydrofuran (THF) were dried over 3 Å molecular sieves and sparged with nitrogen prior to use. Dichloromethane was purified by passing it through a column of alumina under nitrogen. Celite was dried at 125° C. overnight. Sodium hydride was washed with hexanes to remove the mineral oil and dried under vacuum prior to use. The toluene was removed from the methylaluminoxane under vacuum prior to use to give a white powder.

EXAMPLE 20

Preparation of 4-tert-Butyl-2,6-bis-[(2,6-diisopropyl-phenylimino)-methyl]-phenol 4-tert-butyl-2,6-bis-[(2,6-diisopropyl-phenylimino)-methyl]-phenol has the following chemical structure:

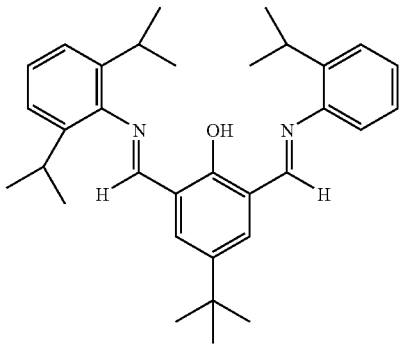

4-tert-butyl-2,6-diformylphenol (5 g, 24.2 mmol) was measured into a 250 mL round bottom flask containing a Teflon coated magnetic stir bar and equipped with a condenser and Dean Stark trap. Toluene (50 mL) was added to the flask followed by 2,6-diisopropylaniline (10 g, 56.4 mmol). An additional 50 mL of toluene was added to the reaction mixture followed by p-toluenesulfonic acid monohydrate (0.046 g, 0.24 mmol). The reaction mixture was briefly sparged with nitrogen and then a static pressure of nitrogen was applied on top of the condenser. The reaction was refluxed for 40 hours. The wet toluene trapped in the Dean Stark apparatus was drained and then the reaction was refluxed for a further 8 hours. About 50 mL of toluene was removed from the reaction mixture by distillation, leaving behind a deep orange solution. The remainder of the solvent was removed under vacuum to give a thick, bright yellow oil that slowly crystallized to give brilliant yellow crystals. The product was recrystallized by dissolving about 4 g of the crude product in 200 mL of hot ethanol. The solution was filtered via cannula to another flask and was allowed to cool under nitrogen to room temperature. The resulting bright yellow needles were washed with two 5 mL portions of cold ethanol and then dried under vacuum. The $^1H$ NMR spectrum of the crystals was consistent with the desired product. $^1H$ NMR (d-chloroform, 500 MHz): δ 1.2 (d, 24 H, $CH_3$), 1.42 (s, 9H, tert-butyl), 3.02 (septet, 4H, CH), 7.2–8.7 (m, 10H, aryl+imine), 13.3 (s, 1H, OH), ppm.

EXAMPLE 21

Preparation of the Precursor Complex of the Present Invention Wherein both $M^1$ and $M^2$ are Palladium, both $L^1$ and $L^2$ are Absent (i.e., Subscripts a, b=0), both $R^1$ and $R^2$ are allyl, Y is Chloride, WCA⁻ is Hexafluorophosphate and $L^3$ is 4-tert-butyl-2,6-bis-[(2,6-diisopropyl-phenylimino)-methyl]-phenoxide The chemical structure of the precursor complex of Example 21 is:

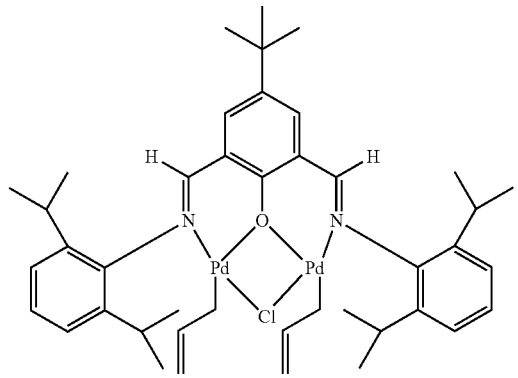

4-tert-butyl-2,6-bis-[(2,6-diisopropyl-phenylimino)-methyl]-phenol (0.2 g, 0.381 mmol) was dissolved in THF (10 mL) in a 50 mL jar. Separately, sodium hydride (0.0114 g, 0.476 mmol) was slurried in THF (10 mL). The ligand solution was added to the sodium hydride slurry. Gas evolution was immediately observed. After 20 minutes, the mixture was vacuum filtered through Celite. The Celite was rinsed with 10 mL of THF. The combined filtrate was concentrated to dryness under vacuum. The residue was dissolved in 10 mL of diethyl ether. Separately, a suspension of allylpalladium chloride dimer (0.130 g, 0.355 mmol) was prepared in 5 mL of diethyl ether. The sodium salt solution was added to the palladium containing slurry. The reaction was allowed to stir at room temperature for 4 h. The material was filtered through Celite. The Celite was rinsed with diethyl ether until the solvent ran clear. The filtrate was concentrated under vacuum. Pentane (10 mL) was added and then removed under vacuum to give a bright yellow powder with a $^1H$ NMR spectrum that was consistent with the desired product.

EXAMPLE 22

Preparation of the Cationic Complex of the Present Invention Wherein $M^1$ is Nickel and $M^2$ is Palladium, $L^1$ is Absent (i.e., Subscript a=0), $L^2$ is Triphenylphosphine, $R^1$ is Phenyl, $R^2$ is Allyl, WCA is Hexafluorophosphate and $L^3$ is 2-[(2,6-Diisopropyl-phenylimino)-methyl]-phenoxide The chemical structure of $(Sal)Ni(C_6H_5)(P(C_6H_5)_3)$ is:

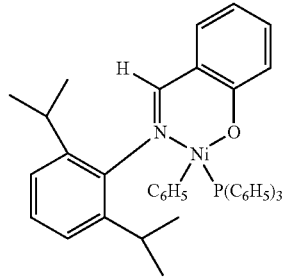

The chemical structure of the cationic complex of Example 22 (S¹ represents a labile ligand) is:

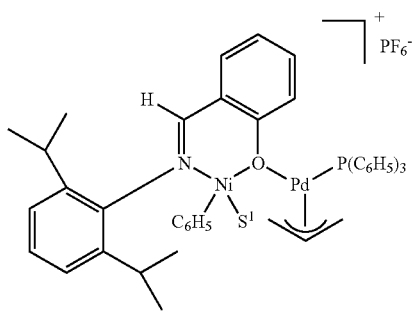

2-[(2,6-Diisopropyl-phenylimino)-methyl]-phenol ("Sal-H") and (Sal)Ni(C$_6$H$_5$)(P(C$_6$H$_5$)$_3$) were prepared according to the literature method of Wang, C. et. al., *Organometallics*, 1998, 17, 3149–3151. (Sal)Ni(C$_6$H$_5$)(P(C$_6$H$_5$)$_3$) (0.100 g, 0.15 mmol) was weighed into an oven dried 1 oz glass vial equipped with a Teflon coated stir bar. The complex was diluted with 5 mL of cold methylene chloride (−35° C.) to give a red/black solution. Separately, allyl palladium chloride dimer (0.027 g, 0.07 mmol) was dissolved in about 2 mL of cold methylene chloride in an oven dried 1 oz vial to give a bright yellow solution. In a third vial, silver hexafluorophosphate (0.037 g, 0.15 mmol) was dissolved in 2 mL of cold methylene chloride. The allyl palladium chloride dimer solution was added to the (Sal)Ni(C$_6$H$_5$)(P(C$_6$H$_5$)$_3$) solution and the vial was rinsed with 2 mL of methylene chloride. The silver salt solution was then added and the vial rinsed with 2 mL of methylene chloride. A dark precipitate immediately fell from solution. After about 5 minutes, the reaction vial was placed in the −35° C. freezer. After about 15 minutes, the reaction mixture was filtered through Celite and the red brown filtrate was concentrated to dryness under vacuum. The product was washed with pentane and vacuum filtered over a medium frit to give a red brown powder and a bright yellow filtrate. The powder was dried under vacuum in the dry box for 4 hours. The red/brown material was collected in a 1 oz oven dried vial. The red/brown powder was essentially insoluble in toluene. In contrast, (Sal)Ni(C$_6$H$_5$)(P(C$_6$H$_5$)$_3$) was readily soluble in toluene and gave a bright yellow solution. The $^1$H and $^{31}$P NMR spectra of the red/brown material, taken in d$_6$-acetone, were consistent with the desired product.

EXAMPLE 23

Preparation of a Homopolymer of Ethylene by the Polymerization of Ethylene Catalyzed by Activating the Precursor Complex of Example 21

Methylaluminoxane (117 mg) and toluene (4 mL) were charged to the glass liner of a steel pressure vessel (8 mL capacity) equipped with a mechanical stirrer. The pressure vessel was sealed and heated to 80° C. Ethylene pressure (350 psig) was introduced. The precursor complex (8 μmol in 0.25 mL of toluene) of Example 21 was injected to the pressure vessel using an oven dried gas tight syringe. 0.75 mL of toluene was added via syringe to rinse the injection port. The polymerization was allowed to proceed under these reaction conditions for 2 h. After this time, the reactor was vented and the contents of the glass liner were added to methanol acidified with hydrochloric acid. After stirring overnight, the precipitated polymer was collected by vacuum filtration and washed with methanol. The polymer was dried in a vacuum oven heated to 60° C. overnight. The dried polymer (0.11 g) was collected in a 1 oz vial. A small sample of the material was analyzed by Differential Scanning Calorimetry (DSC). A melting transition (T$_m$)=132° C. and heat of fusion (ΔH$_f$)=147 J/g were measured for this sample.

EXAMPLE 24

Preparation of the Cationic Complex of the Present Invention Wherein M$^1$ and NV are Both Palladium, L$^1$ and L$^2$ are Both tris(2,4-di-tert-butylphenyl)phosphite, R$^1$ and R$^2$ are Both Allyl, WCA⁻ is hexafluoroantimonate and L$^3$ is Chloride Allylpalladium chloride dimer (0.5 g, 1.37 mmol) was dissolved in 5 mL of methylene chloride in an oven dried 1 oz vial. Separately, silver hexafluoroantimonate (0.469 g, 1.367 mmol) was dissolved in 5 mL of methylene chloride. The silver salt containing solution was added to the bright yellow palladium containing solution to give a lemon yellow slurry. The vial that had contained the silver salt solution was rinsed with 3 mL of methylene chloride. The rinses were added to the reaction mixture. The reaction was allowed to stir at room temperature for 15 minutes. Meanwhile, tris(2,4-di-tert-butylphenyl)phosphite (1.77 g, 2.73 mmol) was dissolved in 5 mL of methylene chloride and then was added to the reaction mixture. The vial was rinsed with 3 mL of methylene chloride and the rinses were added to the reaction. As the ligand was added, much of the heavy precipitate disappeared in solution. The reaction was allowed to stir for 15 minutes. The reaction mixture was then vacuum filtered through a medium frit. The homogeneous yellow filtrate was concentrated to dryness under vacuum to give a sticky yellow solid. Pentane (5 mL) was added to the residue to give a dark yellow solution. A heavy white precipitate formed over 15 minutes. The white solid was diluted with pentane and vacuum filtered through a medium frit. The solid was dried under vacuum for one hour (Yield=2.24 g=88%). $^1$H NMR (d$_6$-acetone, 500 MHz): δ 1.27 (s, 54H, tert-butyl), 1.53 (s, 54H, tert-butyl), 3.12 (br s, 2H, allyl), 3.51 (t, 2H, allyl), 4.10 (br s, 2H, allyl), 4.18 (br s, 2H, allyl), 5.67 (m, 2H allyl), 7.25 (d, 6H, aryl), 7.5 (s, 6H, aryl), 7.65 (d, 6H, aryl) ppm. $^{31}$P{$^1$H, $^{13}$C} NMR: δ 118 (s) ppm.

EXAMPLE 25

Preparation of the Cationic Complex of the Present Invention Wherein Both $M^1$ and $M^2$ are Palladium, Both $L^1$ and $L^2$ are Absent (i.e., Subscripts a, b=0), Both $R^1$ and $R^2$ are Allyl, WCA⁻ is Hexafluorophosphate and $L^3$ is 4-tert-butyl-2,6-bis-[(2,6-diisopropyl-phenylimino)-methyl]-phenoxide The chemical structure of the precursor complex of Example 24 is:

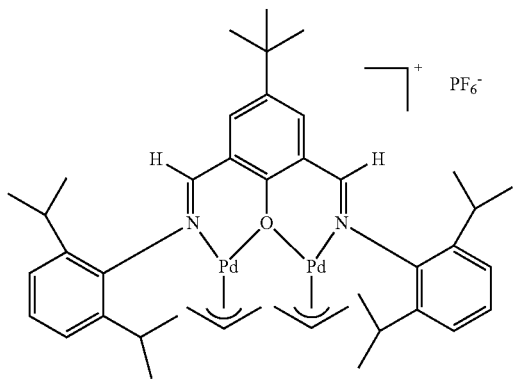

4-tert-butyl-2,6-bis-[(2,6-diisopropyl-phenylimino)-methyl]-phenol (0.300 g, 0.572 mmol) was dissolved in THF (10 mL) in a 50 ml jar. Separately, sodium hydride (0.0172 g, 0.715 mmol) was slurried in THF (10 mL). The ligand solution was slowly added to the sodium hydride slurry. Gas evolution was immediately observed. After 20 minutes, the mixture was vacuum filtered through Celite. The Celite was rinsed with 10 mL of THF. The combined filtrate was concentrated to dryness under vacuum. The residue was dissolved in 10 mL of methyl ene chloride. Separately, solutions of allylpalladium chloride dimer (0.200 g, 0.547 mmol) and silver hexafluorophosphate (0.138 g, 0.547 mmol) were prepared in 5 mL of methylene chloride. The silver salt solution was added to the palladium containing solution to give a yellow slurry. After 10 minutes, the slurry was added to the solution containing the sodium salt of 4-tert-butyl-2,6-bis-[(2,6-diisopropyl-phenylimino)-methyl]-phenol.

After 15 minutes, the resulting orange slurry was filtered through Celite and concentrated to dryness under vacuum to give a bright orange powder. The $^1H$ and $^{31}P$ NMR spectra, taken in $d_6$-benzene, were consistent with the desired product.

EXAMPLE 26

Preparation of a Homopolymer of Norbornene by the Polymerization of Norbornene Catalyzed by the Cationic Complex of Example 25

4.6 g of norbornene in toluene (49 wt. %) was measured into an oven dried 50 mL crimp top vial equipped with Teflon coated magnetic stir bar. Toluene (10 mL) was added to the vessel. The vial was sealed with a septum cap and brought out of the dry box. The vial was placed in a 50° C. temperature regulated water bath. 7.2 μmol of the cationic complex of Example 25 in 1 mL of methylene chloride was added via syringe. After 4 h, the contents of the vial were added to methanol and stirred overnight. The polymer was collected by vacuum filtration and dried in a 60° C. vacuum oven overnight (Yield=1.35 g). The polymer was essentially insoluble in chloroform at ambient temperature.

EXAMPLE 27

Preparation of a Homopolymer of Norbornene by the Polymerization of Norbornene Catalyzed by Activating the Precursor Complex of Example 21

Lithium tetrakis(pentafluorophenyl)borate etherate (2 mg, 2.9 μmol) was charged to an oven dried 50 mL crimp top vial equipped with a Teflon coated magnetic stir bar. 2.81 g of norbornene in toluene (79 wt. %) was added followed by toluene (10 mL). The vial was sealed with a septum cap and brought out of the dry box. The vial was placed in a 50° C. temperature regulated water bath. 1.2 μmol of the cationic complex of Example 21 in 0.25 mL of toluene was added via syringe. After 15 h, the contents of the vial were added to methanol and stirred overnight. The polymer was collected by vacuum filtration and dried in a 60° C. vacuum oven overnight (Yield=2.47 g). The polymer was essentially insoluble in chloroform at ambient temperature.

EXAMPLE 28

Preparation of a Copolymer of Norbornene and Ethylene by the Polymerization of Norbornene and Ethylene Catalyzed by Activating the Precursor Complex of Example 21

Sodium tetrakis[3,5-bis(trifluoromethyl)phenyl]borate (14.2 mg, 16 μmol) and toluene (1 mL) were charged to the glass liner of a steel pressure vessel (8 mL capacity) equipped with a mechanical stirrer. The pressure vessel was sealed and heated to 80° C. 1 mL of norbornene in toluene (79 wt. %) was added using an oven dried gas tight syringe. Toluene (3.25 mL) was used to rinse the injection port into the reactor. Ethylene pressure (350 psig) was introduced. The precursor complex (8 μmol in 0.25 mL of toluene) of Example 21 was injected to the pressure vessel using an oven dried gas tight syringe. 0.75 mL of toluene was added via syringe to rinse the injection port. The polymerization was allowed to proceed under these reaction conditions for 2 h. After this time, the reactor was vented and the contents of the glass liner were added to methanol acidified with hydrochloric acid. After stirring overnight, the precipitated polymer was collected by vacuum filtration and washed with methanol. The polymer was dried in a vacuum oven heated to 60° C. overnight. The dried polymer (0.39 g) was collected in a 1 oz vial. A small sample of the material was analyzed by Differential Scanning Calorimetry (DSC). A glass transition $(T_g)=76°$ C. was measured for this sample. The polymer was entirely soluble in chloroform at ambient temperature. Analysis of the $^1H$ NMR spectrum of the polymer indicated a composition of 55 mol % norbornene and 45 mol % ethylene.

EXAMPLE 29

Preparation of a Homopolymer of Norbornene by the Polymerization of Norbornene Catalyzed by the Cationic Complex of Example 24

2.81 g of norbornene in toluene (79 wt. %) was measured into oven dried 30 mL crimp top vial equipped with Teflon coated magnetic stir bar. Toluene (10 mL) was added to the vial which was then sealed with a septum cap and brought out of the dry box. The vial was placed in a 50° C. temperature regulated water bath. The cationic complex of Example 24 (5 mmol in 1 mL of methylene chloride was added via syringe. After 2 h, the contents of the vial were added to methanol. The polymer was collected by vacuum filtration and dried in a 65° C. vacuum oven overnight (Yield=2.43 g). The polymer was essentially insoluble in chloroform at ambient temperature.

EXAMPLE 30

Preparation of a Polymer of Norbornene by the Polymerization of Norbornene in the Presence of Ethylene Catalyzed by the Cationic Complex of Example 24

2 mL of norbornene in toluene (49 wt. %) and toluene (1 mL) were charged to the glass liner of a steel pressure vessel (8 mL capacity) equipped with a mechanical stirrer. The pressure vessel was sealed and heated to 50° C. Toluene (1 mL) was added using an oven dried gas tight syringe. Ethylene pressure (350 psig) was introduced. The cationic complex (7.2 µmol in 1 mL of methylene chloride) of Example 24 was injected to the pressure vessel via syringe. Toluene (1 mL) was added via syringe to rinse the injection port. The polymerization was allowed to proceed under these reaction conditions for 2 h. After this time, the reactor was vented and the contents of the glass liner were added to methanol. After stirring overnight, the precipitated polymer was collected by vacuum filtration and washed with methanol. The polymer was dried in a vacuum oven heated to 60° C. overnight. The dried polymer (0.81 g) was collected in a 1 oz vial. A small sample of the material was analyzed by Differential Scanning Calorimetry (DSC). A glass transition ($T_g$)=242° C. was measured for this sample. The polymer was entirely soluble in chloroform at ambient temperature. GPC analysis revealed Mn=1300, Mw=7300, Mw/Mn=5.6.

EXAMPLE 31

Preparation of a Catalyst Composition and Use of that Catalyst Composition to a Prepare a Homopolymer of Norbornene and a Copolymer of Norbornene and Methyl Acrylate, According to the Method of the Present Invention Preparation of the first semi-(metal pair) precursor complex: To a clean, dry 40 mL serum vial at −35° C. in a drybox was added: 0.2 g (1.34 mmol) methallylnickelchloride; and 0.375 g (1.34 mmol) $PCy_3$+15 mL tetrahydrofuran (THF). Into a separate vial was weighed 0.46 g (1.34 mmol) $AgSbF_6$+10 mL THF. After adding the methallylnickelchloride solution to the first vial, the contents of the vial were cooled to −35° C. in the dry box freezer. To this vial, with stirring, was slowly added the solution containing $PCy_3$, which was also cooled in the freezer to −35° C. A dark brown solid immediately began to precipitate from solution. The resultant mixture was allowed to stir for 15 minutes, after which time it was transferred to a 100 mL Kjeldahl flask and the THF was removed under vacuum. The flask was then transferred back into the drybox and the solid was extracted with 20 mL $CH_2Cl_2$, filtered over Celite and rinsed with an additional 10 mL $CH_2Cl_2$ The yellow/brown liquid was then transferred into a 100 Kjeldahl flask and was concentrated to about 2 mL using vacuum. Thereupon, 30 mL diethyl ether was added, precipitating an orange/brown solid. This material was isolated by filtration, was washed with excess diethyl ether and was dried under vacuum, and identified as methallylNi—$PCy_3^+SbF_6^-$.

Reaction of a First Semi-(Metal Pair) Precursor Complex with a Second Semi-(Metal Pair) Precursor Complex:

To a clean, dry 5 mL serum vial in the dry box was added 9.1 mg (14.4 µmol) methallylNi-$PCy_3^+SbF_6^-$ and 6.6 mg (14.4 µmol) allylPdCl-$PCy_3$+2.0 mL $CH_2Cl_2$. The vial was allowed to mix (with shaking for about 3 minutes). The resultant solution was orange/brown in color, and was identified as Solution A.

Homopolymerization of Norbornene with Solution A:

To a clean, dry 50 mL serum vial (equipped with a stirring bar) in the drybox was added: 2.8 g (14.6 mmol) norbornene (49 wt % in toluene); and 8.0 mL toluene. The vial was placed in a water bath at 55° C. and allowed to equilibrate. After equilibration, 1.0 mL of Solution A from above (7.2 µmol Ni and Pd) was injected via syringe. The reaction was allowed to proceed for 18 hours whereupon it was terminated by addition of 0.5 mL of acidified methanol (10 wt % HCl). The resultant solution was precipitated in 200 mL of rapidly stirred methanol. After stirring for 60 minutes, the mixture was filtered, washed with excess methanol and dried for 18 hours under vacuum at 60° C. Yield of polymer as a white solid was 1.35 g.

Copolymerization of Norbornene and Methyl Acrylate with Solution A:

To a clean, dry 50 mL serum vial (equipped with a stirring bar) in the drybox was added: 2.3 g (12.0 mmol) norbornene (49 wt % in toluene); 1.03 g (12.0 mmol) methyl acrylate; and 8.0 mL toluene. The vial was placed in a water bath at 55° C. and allowed to equilibrate. After equilibration, 1.0 mL of Solution A from above (7.2 µmol Ni and Pd) was injected via syringe. The reaction was allowed to proceed for 18 hours whereupon it was terminated by addition of 0.5 mL of acidified methanol (10 wt % HCl). The resultant solution was precipitated in 200 mL of rapidly stirred methanol. After stirring for 60 minutes, the mixture was filtered, washed with excess methanol and dried for 18 hours under vacuum at 60° C. Yield of polymer as a white solid was 0.22 g. Methyl acrylate incorporation was determined by $^1H$ NMR to be 63.5 mol %, Mw=36,000, Mn=24,000 Mw/Mn=1.5.

EXAMPLE 32

Utilizing a Catalytic Cationic Metal-pair Complex to Prepare a Terpolymer of Norbornene, 1-octene and Methyl Acrylate, According to the Method of the Present Invention Glass vial A was charged with allylpalladium chloride dimer (38.4 mg, 0.104 mmol). $CH_2Cl_2$ (1 mL) was added to form a clear yellow solution. Glass vial B was charged with lithium tetrakis(pentafluorophenyl)borate etherate (173.6 mg, 0.208 mmol). $CH_2Cl_2$ (2 mL) was added to form a brownish yellow solution. Glass vial C was charged with tris(2,4-di-tert-butylphenyl)phosphite (134.6 mg, 0.208 mmol). CH$_2$Cl$_2$ (2 mL) was added to form a clear colorless solution. The solution in glass vial B was mixed with that in glass vial A to form a brownish yellow solution with white fine particles, which was stored in glass vial A. Glass vial B was rinsed with CH$_2$Cl$_2$ (2 mL) and the solution was added to glass vial A. The mixture was swirled at room temperature for 1 min. The solution in glass vial C was added to glass vial A to form a brownish yellow solution with white fine particles. Glass vial C was rinsed with CH$_2$Cl$_2$ (2 mL) and the solution was added to glass vial A. The mixture was swirled at room temperature, which was labeled Catalyst Solution A. A 50-mL serum bottle was charged with full amount of NB (12 mmol, pre-dissolved in toluene, 79 wt %), MA (12 mmol), 1-octene (30 mmol) and toluene (1 mL) to form a clear colorless solution. The reaction mixtures was sealed with rubber septum and transferred to the fume hood. Catalyst Solution A (0.5 mL) was added to form a clear pale yellow solution. 1 min after the catalyst was added, all reaction mixtures were stirred at 50 deg C. using a water bath in the fume hood. 3 hours later, the reaction mixture appeared clear and yellow, which was quenched with methanol (ca. 150 mL) and the solid was isolated by filtration and dried under vacuum at 65 deg C. overnight to yield a yellow solid (98 mg). $^1$H NMR analysis revealed that the product had a molar ratio of 9 (norbornene): 12 (1-octene): 79 (methyl acrylate). GPC experiment exhibited a unimodal pattern: Mw 68400, Mn 47300, Mw/Mn 1.5.

EXAMPLE 33

Utilizing a Catalytic Cationic Metal-pair Complex to Prepare a Terpolymer of an Acrylate, Norbornene, and a Substituted Norbornene, According to the Method of the Present Invention Glass vial A was charged with allylpalladium chloride dimer (15.0 mg, 41 μmol). CH$_2$Cl$_2$ (1 mL) was added to form a yellow solution. Glass vial B was charged with lithium tetrakis(pentafluorophenyl)borate etherate (34.2 mg, 41 μmol). CH$_2$Cl$_2$ (1 mL) was added to form a brownish yellow solution. Glass vial C was charged with tris(2,4-di-tert-butylphenyl)phosphite (53.1 mg, 82 μmol). CH$_2$Cl$_2$ (1 mL) was added to form a clear colorless solution. The solution in glass vial B was mixed with that in glass vial A to form a clear brownish yellow solution, which was stored in glass vial A. Glass vial B was rinsed with CH$_2$Cl$_2$ (1 mL) and the solution was added to glass vial A. The mixture was swirled at room temperature for 1 min. The solution in glass vial C was added to glass vial A to yield a clear yellow solution. Glass vial C was rinsed with CH$_2$Cl$_2$ (1 mL) and the solution was added to glass vial A. The mixture was swirled at room temperature, which was labeled Catalyst Solution A. A 100-mL serum bottle was charged with hexafluoroisopropanol norbornene (12.5 mmol), tert-butyl acrylate (12.5 mmol) and 1-octene (25 mmol). Catalyst Solution A (5 mL) was added to the reaction mixture to form a clear pale yellow solution, which was sealed with rubber septum and transferred to the fume hood. About 5 minutes after the catalyst was added, the reaction mixture was stirred at 50 deg C. using a water bath in the fume hood. 118 hours later, the reaction mixture was clean and yellow, which was quenched with methanol. Volatiles were removed under vacuum at ambient temperature overnight to yield a pale yellow solid (430 mg). $^{13}$C NMR analysis revealed that the product had a molar ratio of 24 (hexafluoroisopropanol norbornene): 15 (1-octene): 61 (tert-butyl acrylate). GPC experiment exhibited a unimodal pattern: Mw 30000, Mn 23000, Mw/Mn 1.3.

We claim:
1. A catalytic composition comprising at least one cationic metal-pair complex, wherein:
   said cationic metal-pair complex comprises at least one metal atom pair, said pair comprising a first metal atom, M$^1$, and a second metal atom, M$^2$;
   said first metal atom and said second metal atom of said pair have a through-space internuclear distance of at least 1.5 Angstroms and no more than 20 Angstroms; and
   said cationic metal-pair complex is a complex according to formula I,

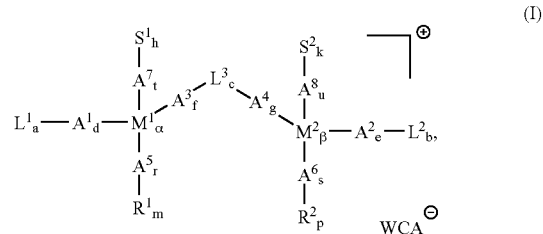

wherein:
   M$^1$ represents a first metal atom selected from the group consisting of: nickel, palladium, platinum, copper, silver, gold, iron, cobalt, rhodium, chromium, and manganese;
   M$^2$ represents a second metal atom selected from the group consisting of: nickel, palladium, platinum, copper, silver, gold, iron, cobalt, rhodium, chromium, and manganese;
   L$^1$ represents a set of first ligands;
   L$^2$ represents a set of second ligands;
   L$^3$ represents a set of third ligands;
   R$^1$ represents a set of first anionic hydrocarbyl containing radicals;
   R$^2$ represents a set of second anionic hydrocarbyl containing radicals;
   S$^1$ represents a set of first labile ligands;
   S$^2$ represents a set of second labile ligands;
   A$^1$–A$^8$ each represent a set of coordination bonds;
   WCA represents a weakly coordinating anion;
   a, b, h, k, m, and p are selected from 0 or 1;
   α, β, and c each equal 1;
   d, e, r, s, t, and u are selected from 0, 1, 2, or 3; and
   f and g are selected from 1, 2, 3, or 4; and
   wherein: $0 \leq d+e \leq 5$; $1 \leq m+p \leq 2$; $1 \leq r+s \leq 5$; $0 \leq t+u \leq 5$; $2 \leq f+g \leq 7$; the sum d+f+r+t=4; and the sum e+g+s+u=4.

2. The catalytic composition of claim 1, wherein said first metal atom and said second metal atom of said pair have a through-space internuclear distance of at least 2 Angstroms and no more than 10 Angstroms.

3. A method for preparing said catalytic composition of claim 1, comprising the steps of:
   (i) providing at least one precursor complex according to formula II

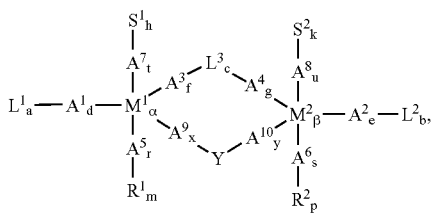

(II)

wherein:
- $M^1$ represents a first metal atom selected from the group consisting of: nickel, palladium, platinum, copper, silver, gold, iron, cobalt, rhodium, chromium, and manganese;
- $M^2$ represents a second metal atom selected from the group consisting of: nickel, palladium, platinum, copper, silver, gold, iron, cobalt, rhodium, chromium, and manganese;
- $L^1$ represents a set of first ligands;
- $L^2$ represents a set of second ligands;
- $L^3$ represents a set of third ligands;
- $R^1$ represents a set of first anionic hydrocarbyl containing radicals;
- $R^2$ represents a set of second anionic hydrocarbyl containing radicals;
- $S^1$ represents a set of first labile ligands;
- $S^2$ represents a set of second labile ligands;
- $A^1$–$A^{10}$ each represent a set of coordinating bonds; and
- Y represents a leaving group;

(ii) combining said precursor complex with at least one activator component;

(iii) removing said leaving group Y from said precursor complex; and (iv) replacing said leaving group Y with at least one replacement moiety, wherein:
a, b, d, h, k, m, p, r, s, t, and u are as defined for Formula 1 in claim 1;
α, β, c, x, and y are selected from 0 or 1;
e is selected from 0, 1, 2, 3, or 4;
f and g are selected from 0, 1, 2, 3, or 4;
$0 \leq d+e \leq 4$;
the sum f+g is selected from 0, 2, 3, 4, 5, or 6;
$1 \leq m+p \leq 2$;
$1 \leq r+s \leq 5$;
$0 \leq t+u \leq 4$;
$1 \leq x+y \leq 2$;
the sum d+f+r+t+x is selected from 0 or 4; and
the sum e+g+s+u+y is selected from 0 or 4.

4. The method of claim 3, wherein:
said precursor complex is a full-(metal pair) precursor complex according to said formula II wherein:
a, b, h, k, x, and y are selected from 0 or 1;
α, β, and c each equal 1;
d, e, r, s, t, and u are selected from 0, 1, 2, or 3;
f and g are selected from 1, 2, 3, or 4; and
wherein: $1 \leq m+p \leq 2$; $0 \leq d+e \leq 4$; $1 \leq r+s \leq 5$; $0 \leq t+u \leq 4$; $1 \leq x+y \leq 2$; $2 \leq f+g \leq 6$; the sum d+f+r+t+x=4, and the sum e+g+s+u+y=4.

5. The method of claim 3, wherein:
said precursor complex is a first semi-(metal pair) precursor complex according to said formula II wherein:
α and x each equal 1; β, b, c, k, p, e, f, g, s, u, and y each equal 0; a, h, and m are selected from 0 or 1; d, r, and t are selected from 0, 1, 2, or 3; and the sum d+f+r+t+x=4; and
said replacement moiety is a second semi-(metal pair) precursor complex according to said formula II wherein:
β equals 1; α, a, c, h, m, d, f, g, r, t, x, and y each equal 0; b, k, and p are selected from 0 or 1; e is selected from 0, 1, 2, 3, or 4; s and u are selected from 0, 1, 2, or 3; and the sum e+g+s+u+y=4; and
the sum of m of said first semi-(metal pair) complex+p of said second semi-(metal pair) complex is selected from 1 or 2.

6. A method for preparing at least one addition polymer comprising:
(a) combining:
(i) at least one catalytic composition according to claim 1; and
(ii) at least one ethylenically unsaturated monomer; and
(b) polymerizing said at least one ethylenically unsaturated monomer in the presence of said at least one catalytic composition to form said addition polymer.

7. The method of claim 6, wherein said addition polymer is a polymer selected from: poly[(polar olefin)-(non-polar olefin)], poly(polar olefin), poly(non-polar olefin), and combinations thereof, wherein said ethylenically unsaturated monomers are selected from at least one polar olefinic monomer and at least one non-polar olefinic monomers.

8. The method of claim 7, wherein the combined molar percentage of said at least one polar olefinic monomer and at least one non-polar olefinic monomer present, as polymerized units, in said poly[(polar olefin)-(non-polar olefin)] is at least 70 mole-% to 100 mole-%, based upon the total moles of all said polar olefinic monomers and said non-polar olefinic monomers present, as polymerized units, in said at least one addition polymer.

9. The method of claim 6, wherein said addition polymer comprises, as polymerized units, at least one (meth)acrylate monomer, wherein the molar ratio of all said (meth)acrylate monomers to all said ethylenically unsaturated monomers monomers, present as polymerized units, is at least 0.05: 99.95 to 100:0.

10. The method of claim 6, wherein said addition polymer comprises, as polymerized units, at least one cyclic olefin monomer, wherein the molar ratio of all said cyclic olefin monomers to all said ethylenically unsaturated monomers, present as polymerized units, is at least 0.05:99.95 to 100:0.

11. The catalytic composition of claim 1, wherein at least one of said first anionic hydrocarbyl radicals and said second anionic hydrocarbyl radicals is an addition polymer.

* * * * *